US008722021B2

(12) United States Patent
Friedman et al.

(10) Patent No.: US 8,722,021 B2
(45) Date of Patent: May 13, 2014

(54) FOAMABLE CARRIERS

(71) Applicant: Foamix Ltd., Rehovot (IL)

(72) Inventors: Doron Friedman, Karmei Yosef (IL); Alex Besonov, Rehovot (IL); Dov Tamarkin, Ness Ziona (IL); Meir Eini, Ness Ziona (IL)

(73) Assignee: Foamix Ltd., Rehovot (IL)

( * ) Notice: Subject to any disclaimer, the term of this patent is extended or adjusted under 35 U.S.C. 154(b) by 0 days.

(21) Appl. No.: 13/786,902

(22) Filed: Mar. 6, 2013

(65) Prior Publication Data

US 2013/0183250 A1 Jul. 18, 2013

Related U.S. Application Data

(63) Continuation of application No. 11/116,761, filed on Apr. 28, 2005, which is a continuation-in-part of application No. PCT/IB03/05527, filed on Oct. 24, 2003, said application No. 11/116,761 is a continuation-in-part of application No. 10/911,367, filed on Aug. 4, 2004.

(60) Provisional application No. 60/429,546, filed on Nov. 29, 2002, provisional application No. 60/492,385, filed on Aug. 4, 2003, provisional application No. 60/566,513, filed on Apr. 28, 2004.

(30) Foreign Application Priority Data

Oct. 25, 2002 (IL) .......................................... 152486

(51) Int. Cl.
*A01N 25/02* (2006.01)

(52) U.S. Cl.
USPC ......................................................... 424/43

(58) Field of Classification Search
None
See application file for complete search history.

(56) References Cited

U.S. PATENT DOCUMENTS

| | | | |
|---|---|---|---|
| 1,159,250 A | 11/1915 | Moulton |
| 1,666,684 A | 4/1928 | Carstens |
| 1,924,972 A | 8/1933 | Beckert |
| 2,085,733 A | 7/1937 | Bird |
| 2,390,921 A | 12/1945 | Clark |
| 2,524,590 A | 10/1950 | Boe |
| 2,586,287 A | 2/1952 | Apperson |
| 2,617,754 A | 11/1952 | Neely |
| 2,767,712 A | 10/1956 | Waterman |
| 2,968,628 A | 1/1961 | Reed |
| 3,004,894 A | 10/1961 | Johnson et al. |
| 3,062,715 A | 11/1962 | Reese et al. |
| 3,067,784 A | 12/1962 | Gorman |
| 3,092,255 A | 6/1963 | Hohman |
| 3,092,555 A | 6/1963 | Horn |
| 3,141,821 A | 7/1964 | Compeau |
| 3,142,420 A | 7/1964 | Gawthrop |
| 3,144,386 A | 8/1964 | Brightenback |
| 3,149,543 A | 9/1964 | Naab |
| 3,154,075 A | 10/1964 | Weckesser |
| 3,178,352 A | 4/1965 | Erickson |
| 3,236,457 A | 2/1966 | Kennedy et al. |
| 3,244,589 A | 4/1966 | Sunnen |
| 3,252,859 A | 5/1966 | Silver |
| 3,261,695 A | 7/1966 | Sienkiewicz |
| 3,263,867 A | 8/1966 | Lehmann |
| 3,263,869 A | 8/1966 | Corsette |
| 3,298,919 A | 1/1967 | Bishop et al. |
| 3,301,444 A | 1/1967 | Wittke |
| 3,303,970 A | 2/1967 | Breslau et al. |
| 3,330,730 A | 7/1967 | Hernandez |
| 3,333,333 A | 8/1967 | Noack |
| 3,346,451 A | 10/1967 | Collins et al. |
| 3,366,494 A | 1/1968 | Bower et al. |
| 3,369,034 A | 2/1968 | Chalmers |
| 3,377,004 A | 4/1968 | Wittke |
| 3,384,541 A | 5/1968 | Clark et al. |
| 3,395,214 A | 7/1968 | Mummert |
| 3,395,215 A | 7/1968 | Schubert |
| 3,401,849 A | 9/1968 | Weber, III |
| 3,419,658 A | 12/1968 | Sanders |
| 3,456,052 A | 7/1969 | Gordon |
| 3,527,559 A | 9/1970 | Sliwinski |
| 3,540,448 A | 11/1970 | Sunnen |
| 3,559,890 A | 2/1971 | Brooks et al. |
| 3,561,262 A | 2/1971 | Borucki |
| 3,563,098 A | 2/1971 | Weber, III |
| 3,574,821 A | 4/1971 | Pfirrmann |

(Continued)

FOREIGN PATENT DOCUMENTS

| | | |
|---|---|---|
| AU | 198780257 | 9/1986 |
| CA | 2422244 | 9/2003 |

(Continued)

OTHER PUBLICATIONS

U.S. Appl. No. 60/789,186, filed Apr. 4, 2006, Tamarkin.
U.S. Appl. No. 60/815,948, filed Jun. 23, 2006, Tamarkin.
U.S. Appl. No. 60/818,634, filed Jul. 5, 2006, Friedman.
U.S. Appl. No. 60/843,140, filed Sep. 8, 2006, Tamarkin.
U.S. Appl. No. 61/248,144, filed Oct. 2, 2009, Tamarkin.
U.S. Appl. No. 61/322,148, filed Apr. 8, 2010, Tamarkin.
U.S. Appl. No. 61/363,577, filed Jul. 12, 2010, Eini.
"Burn patients need vitamin D supplements." *Decision News Media*, Jan. 23, 2004, http://www.nutraingredients.com/Research/Burn-patients-need-vitamin-D-supplements, Accessed: May 5, 2010.
"HLB Systems", http://pharmcal.tripod.com/ch17.htm, Accessed Sep. 17, 2010, pp. 1-3.
"Minocycline" accessed on Oct. 21, 2011 at en.wikipedia.org/wiki/Minocycline, 7 pages.

(Continued)

*Primary Examiner* — Suzanne Ziska
(74) *Attorney, Agent, or Firm* — Fish & Richardson P.C.

(57) ABSTRACT

The invention relates to an alcohol-free cosmetic or therapeutic foam carrier comprising water, a hydrophobic organic carrier, a foam adjuvant agent, a surface-active agent and a gelling agent. The cosmetic or therapeutic foam carrier does not contain aliphatic alcohols, making it non-irritating and non-drying. The alcohol-free foam carrier is suitable for inclusion of both water-soluble and oil soluble therapeutic and cosmetic agents.

27 Claims, No Drawings

(56) References Cited

U.S. PATENT DOCUMENTS

| | | |
|---|---|---|
| 3,577,518 A | 5/1971 | Shepherd |
| 3,667,461 A | 6/1972 | Zamarra |
| 3,751,562 A | 8/1973 | Nichols |
| 3,770,648 A | 11/1973 | Mackles |
| 3,787,566 A | 1/1974 | Gauvreau |
| 3,819,524 A | 6/1974 | Schubert et al. |
| 3,841,525 A | 10/1974 | Siegel |
| 3,849,580 A | 11/1974 | Weinstein et al. |
| 3,865,275 A | 2/1975 | De Nunzio |
| 3,866,800 A | 2/1975 | Schmitt |
| 3,882,228 A | 5/1975 | Boncey et al. |
| 3,886,084 A | 5/1975 | Vassiliades |
| 3,890,305 A | 6/1975 | Weber et al. |
| 3,912,665 A | 10/1975 | Spitzer et al. |
| 3,923,970 A | 12/1975 | Breuer |
| 3,929,985 A * | 12/1975 | Webb, Jr. .................. 424/45 |
| 3,952,916 A | 4/1976 | Phillips |
| 3,959,160 A | 5/1976 | Horsler et al. |
| 3,962,150 A | 6/1976 | Viola |
| 3,963,833 A | 6/1976 | DeSalva et al. |
| 3,966,090 A | 6/1976 | Prussin et al. |
| 3,966,632 A | 6/1976 | Colliopoulos et al. |
| 3,970,219 A | 7/1976 | Spitzer et al. |
| 3,970,584 A | 7/1976 | Hart et al. |
| 3,993,224 A | 11/1976 | Harrison |
| 3,997,467 A | 12/1976 | Jederstrom |
| 4,001,391 A | 1/1977 | Feinstone et al. |
| 4,001,442 A | 1/1977 | Stahlberger et al. |
| 4,018,396 A | 4/1977 | Shoemaker et al. |
| 4,019,657 A | 4/1977 | Spitzer et al. |
| 4,083,974 A | 4/1978 | Turi |
| 4,102,995 A | 7/1978 | Hebborn |
| 4,110,426 A | 8/1978 | Barnhurst et al. |
| 4,124,149 A | 11/1978 | Spitzer et al. |
| 4,145,411 A | 3/1979 | Mende |
| 4,151,272 A | 4/1979 | Geary et al. |
| 4,160,827 A | 7/1979 | Cho et al. |
| 4,213,979 A | 7/1980 | Levine |
| 4,214,000 A | 7/1980 | Papa |
| 4,226,344 A | 10/1980 | Booth et al. |
| 4,229,432 A | 10/1980 | Geria |
| 4,230,701 A | 10/1980 | Holick et al. |
| 4,241,048 A | 12/1980 | Durbak et al. |
| 4,241,149 A | 12/1980 | Labes et al. |
| 4,252,787 A | 2/1981 | Sherman et al. |
| 4,254,104 A | 3/1981 | Suzuki et al. |
| 4,268,499 A | 5/1981 | Keil |
| 4,271,149 A | 6/1981 | Winicov et al. |
| 4,292,250 A | 9/1981 | DeLuca et al. |
| 4,292,326 A | 9/1981 | Nazzaro-Porro et al. |
| 4,299,826 A | 11/1981 | Luedders |
| 4,305,936 A | 12/1981 | Klein |
| 4,309,995 A | 1/1982 | Sacco |
| 4,310,510 A * | 1/1982 | Sherman et al. ............. 424/45 |
| 4,323,582 A | 4/1982 | Siegel et al. |
| 4,323,694 A | 4/1982 | Scala, Jr. |
| 4,325,939 A | 4/1982 | Shah |
| 4,329,990 A | 5/1982 | Sneider |
| 4,335,120 A | 6/1982 | Holick et al. |
| 4,352,808 A | 10/1982 | Rane et al. |
| 4,385,161 A | 5/1983 | Caunt et al. |
| 4,386,104 A | 5/1983 | Nazzaro-Porro |
| 4,393,066 A | 7/1983 | Garrett et al. |
| 4,427,670 A | 1/1984 | Ofuchi et al. |
| 4,439,416 A | 3/1984 | Cordon et al. |
| 4,439,441 A | 3/1984 | Hallesy et al. |
| 4,440,320 A | 4/1984 | Wernicke |
| 4,447,486 A | 5/1984 | Hoppe et al. |
| 4,469,674 A | 9/1984 | Shah et al. |
| 4,508,705 A | 4/1985 | Chaudhuri et al. |
| 4,522,948 A | 6/1985 | Walker |
| 4,529,601 A | 7/1985 | Broberg et al. |
| 4,552,872 A | 11/1985 | Cooper et al. |
| 4,574,052 A | 3/1986 | Gupte et al. |
| 4,576,961 A | 3/1986 | Lorck et al. |
| 4,595,526 A | 6/1986 | Lai |
| 4,603,812 A | 8/1986 | Stoesser et al. |
| 4,627,973 A | 12/1986 | Moran et al. |
| 4,628,063 A | 12/1986 | Haines et al. |
| 4,661,524 A | 4/1987 | Thomson et al. |
| 4,672,078 A | 6/1987 | Sakai et al. |
| 4,673,569 A | 6/1987 | Shernov et al. |
| 4,678,463 A | 7/1987 | Millar |
| 4,701,320 A | 10/1987 | Hasegawa et al. |
| 4,725,609 A | 2/1988 | Kull, Jr. et al. |
| 4,738,396 A | 4/1988 | Doi et al. |
| 4,741,855 A | 5/1988 | Grote et al. |
| 4,752,465 A | 6/1988 | Mackles |
| 4,770,634 A | 9/1988 | Pellico |
| 4,780,309 A | 10/1988 | Geria et al. |
| 4,784,842 A | 11/1988 | London et al. |
| 4,792,062 A | 12/1988 | Goncalves |
| 4,798,682 A | 1/1989 | Ansmann |
| 4,804,674 A | 2/1989 | Curtis-Prior et al. |
| 4,806,262 A | 2/1989 | Snyder |
| 4,808,388 A | 2/1989 | Beutler et al. |
| 4,822,613 A | 4/1989 | Rodero |
| 4,822,614 A | 4/1989 | Rodero |
| 4,826,048 A | 5/1989 | Skorka et al. |
| 4,827,378 A | 5/1989 | Gillan et al. |
| 4,828,837 A | 5/1989 | Uster et al. |
| 4,836,217 A | 6/1989 | Fischer et al. |
| 4,837,019 A | 6/1989 | Georgalas et al. |
| 4,837,378 A | 6/1989 | Borgman |
| 4,844,902 A | 7/1989 | Grohe |
| 4,847,068 A | 7/1989 | Dole et al. |
| 4,849,117 A | 7/1989 | Bronner et al. |
| 4,855,294 A | 8/1989 | Patel et al. |
| 4,863,900 A | 9/1989 | Pollock et al. |
| 4,867,967 A | 9/1989 | Crutcher |
| 4,873,078 A | 10/1989 | Edmundson et al. |
| 4,874,794 A | 10/1989 | Katz |
| 4,877,805 A | 10/1989 | Kligman |
| 4,885,282 A | 12/1989 | Thornfeldt |
| 4,897,262 A | 1/1990 | Nandagiri et al. |
| 4,902,281 A | 2/1990 | Avoy |
| 4,906,453 A | 3/1990 | Tsoucalas |
| 4,913,893 A | 4/1990 | Varco et al. |
| 4,919,934 A | 4/1990 | Deckner et al. |
| 4,954,487 A | 9/1990 | Cooper et al. |
| 4,956,049 A | 9/1990 | Bernheim et al. |
| 4,957,732 A | 9/1990 | Grollier et al. |
| 4,963,351 A | 10/1990 | Weston |
| 4,966,779 A | 10/1990 | Kirk |
| 4,970,067 A | 11/1990 | Panandiker et al. |
| 4,975,466 A | 12/1990 | Bottcher et al. |
| 4,981,367 A | 1/1991 | Brazelton |
| 4,981,677 A | 1/1991 | Thau |
| 4,981,679 A | 1/1991 | Briggs et al. |
| 4,981,845 A | 1/1991 | Pereira et al. |
| 4,985,459 A | 1/1991 | Sunshine et al. |
| 4,992,478 A | 2/1991 | Geria |
| 4,993,496 A | 2/1991 | Riedle et al. |
| 5,002,540 A | 3/1991 | Brodman et al. |
| 5,002,680 A | 3/1991 | Schmidt et al. |
| 5,007,556 A | 4/1991 | Lover |
| 5,013,297 A | 5/1991 | Cattanach |
| 5,015,471 A | 5/1991 | Birtwistle et al. |
| 5,019,375 A | 5/1991 | Tanner et al. |
| 5,034,220 A | 7/1991 | Helioff et al. |
| 5,035,895 A | 7/1991 | Shibusawa et al. |
| 5,053,228 A | 10/1991 | Mori et al. |
| 5,071,648 A | 12/1991 | Rosenblatt |
| 5,071,881 A | 12/1991 | Parfondry et al. |
| 5,073,371 A | 12/1991 | Turner et al. |
| 5,082,651 A | 1/1992 | Healey et al. |
| 5,087,618 A | 2/1992 | Bodor |
| 5,089,252 A | 2/1992 | Grollier et al. |
| 5,091,111 A | 2/1992 | Neumiller |
| 5,094,853 A | 3/1992 | Hagarty |
| 5,100,917 A | 3/1992 | Flynn et al. |
| 5,104,645 A | 4/1992 | Cardin et al. |
| 5,112,359 A | 5/1992 | Murphy et al. |
| 5,114,718 A | 5/1992 | Damani |

(56) References Cited

U.S. PATENT DOCUMENTS

| | | |
|---|---|---|
| 5,122,519 A | 6/1992 | Ritter |
| 5,130,121 A | 7/1992 | Kopolow et al. |
| 5,133,972 A | 7/1992 | Ferrini et al. |
| 5,135,915 A | 8/1992 | Czarniecki et al. |
| 5,137,714 A | 8/1992 | Scott |
| 5,143,717 A | 9/1992 | Davis |
| 5,156,765 A | 10/1992 | Smrt |
| 5,164,357 A | 11/1992 | Bartman et al. |
| 5,164,367 A | 11/1992 | Pickart |
| 5,167,950 A | 12/1992 | Lins |
| 5,171,577 A | 12/1992 | Griat et al. |
| 5,196,405 A | 3/1993 | Packman |
| 5,204,093 A | 4/1993 | Victor |
| 5,208,031 A | 5/1993 | Kelly |
| 5,217,707 A | 6/1993 | Szabo et al. |
| 5,219,877 A | 6/1993 | Shah et al. |
| 5,221,696 A | 6/1993 | Ke et al. |
| 5,230,897 A | 7/1993 | Griffin et al. |
| 5,236,707 A | 8/1993 | Stewart, II |
| 5,252,246 A | 10/1993 | Ding et al. |
| 5,254,334 A | 10/1993 | Ramirez et al. |
| 5,262,407 A | 11/1993 | Leveque et al. |
| 5,266,592 A | 11/1993 | Grub et al. |
| 5,279,819 A | 1/1994 | Hayes |
| 5,286,475 A | 2/1994 | Louvet et al. |
| 5,300,286 A | 4/1994 | Gee |
| 5,301,841 A | 4/1994 | Fuchs |
| 5,308,643 A | 5/1994 | Osipow et al. |
| 5,314,904 A | 5/1994 | Egidio et al. |
| 5,322,683 A | 6/1994 | Mackles et al. |
| 5,326,557 A | 7/1994 | Glover et al. |
| 5,344,051 A | 9/1994 | Brown |
| 5,346,135 A | 9/1994 | Vincent |
| 5,352,437 A | 10/1994 | Nakagawa et al. |
| 5,369,131 A | 11/1994 | Poli et al. |
| 5,378,451 A | 1/1995 | Gorman et al. |
| 5,378,730 A | 1/1995 | Lee et al. |
| 5,380,761 A | 1/1995 | Szabo et al. |
| 5,384,308 A | 1/1995 | Henkin |
| 5,385,943 A | 1/1995 | Nazzaro-Porro |
| 5,389,676 A | 2/1995 | Michaels |
| 5,397,312 A | 3/1995 | Rademaker et al. |
| 5,398,846 A | 3/1995 | Corba et al. |
| 5,399,205 A | 3/1995 | Shinohara et al. |
| 5,411,992 A | 5/1995 | Eini et al. |
| 5,422,361 A | 6/1995 | Munayyer et al. |
| 5,429,815 A | 7/1995 | Faryniarz et al. |
| 5,435,996 A | 7/1995 | Glover et al. |
| 5,447,725 A | 9/1995 | Damani et al. |
| 5,449,520 A | 9/1995 | Frigerio et al. |
| 5,451,404 A | 9/1995 | Furman |
| 5,482,965 A | 1/1996 | Rajadhyaksha |
| 5,491,245 A | 2/1996 | Gruning et al. |
| 5,500,211 A | 3/1996 | George et al. |
| 5,508,033 A | 4/1996 | Briand et al. |
| 5,512,555 A | 4/1996 | Waldstreicher |
| 5,514,367 A | 5/1996 | Lentini et al. |
| 5,514,369 A | 5/1996 | Salka et al. |
| 5,520,918 A | 5/1996 | Smith |
| 5,523,078 A | 6/1996 | Baylin |
| 5,527,534 A | 6/1996 | Myhling |
| 5,527,822 A | 6/1996 | Scheiner |
| 5,529,770 A | 6/1996 | McKinzie et al. |
| 5,531,703 A | 7/1996 | Skwarek et al. |
| 5,534,261 A | 7/1996 | Rodgers et al. |
| 5,536,743 A * | 7/1996 | Borgman .................. 514/398 |
| 5,540,853 A | 7/1996 | Trinh et al. |
| 5,545,401 A | 8/1996 | Shanbrom |
| 5,567,420 A | 10/1996 | McEleney et al. |
| 5,576,016 A | 11/1996 | Amselem et al. |
| 5,578,315 A | 11/1996 | Chien et al. |
| 5,585,104 A | 12/1996 | Ha et al. |
| 5,589,157 A | 12/1996 | Hatfield |
| 5,589,515 A | 12/1996 | Suzuki et al. |
| 5,597,560 A | 1/1997 | Bergamini et al. |
| 5,603,940 A | 2/1997 | Candau et al. |
| 5,605,679 A | 2/1997 | Hansenne et al. |
| 5,608,119 A | 3/1997 | Amano et al. |
| 5,611,463 A | 3/1997 | Favre |
| 5,612,056 A | 3/1997 | Jenner et al. |
| 5,613,583 A | 3/1997 | Kono et al. |
| 5,613,623 A | 3/1997 | Hildebrandt |
| 5,614,171 A | 3/1997 | Clavenna et al. |
| 5,614,178 A | 3/1997 | Bloom et al. |
| 5,635,469 A | 6/1997 | Fowler et al. |
| 5,641,480 A | 6/1997 | Vermeer |
| 5,643,600 A | 7/1997 | Mathur |
| 5,645,842 A | 7/1997 | Gruning et al. |
| 5,650,554 A | 7/1997 | Moloney |
| 5,658,575 A | 8/1997 | Ribier et al. |
| 5,658,749 A | 8/1997 | Thornton |
| 5,658,956 A | 8/1997 | Martin et al. |
| 5,663,208 A | 9/1997 | Martin |
| 5,672,634 A | 9/1997 | Tseng et al. |
| 5,679,324 A | 10/1997 | Lisboa et al. |
| 5,683,710 A | 11/1997 | Akemi et al. |
| 5,686,088 A | 11/1997 | Mitra et al. |
| 5,693,258 A | 12/1997 | Tonomura et al. |
| 5,695,551 A | 12/1997 | Buckingham et al. |
| 5,700,396 A | 12/1997 | Suzuki et al. |
| 5,716,611 A | 2/1998 | Oshlack et al. |
| 5,716,621 A | 2/1998 | Bello |
| 5,719,122 A | 2/1998 | Chiodini et al. |
| 5,719,197 A | 2/1998 | Kanios et al. |
| 5,725,872 A | 3/1998 | Stamm et al. |
| 5,725,874 A | 3/1998 | Oda |
| 5,730,964 A | 3/1998 | Waldstreicher |
| 5,733,558 A | 3/1998 | Breton et al. |
| 5,733,572 A | 3/1998 | Unger et al. |
| 5,747,049 A | 5/1998 | Tominaga |
| 5,753,241 A | 5/1998 | Ribier et al. |
| 5,753,245 A | 5/1998 | Fowler et al. |
| 5,759,520 A | 6/1998 | Sachetto |
| 5,759,579 A | 6/1998 | Singh et al. |
| 5,767,104 A | 6/1998 | Bar-Shalom et al. |
| 5,773,410 A | 6/1998 | Yamamoto |
| 5,783,202 A | 7/1998 | Tomlinson et al. |
| 5,788,664 A | 8/1998 | Scalise |
| 5,792,448 A | 8/1998 | Dubief et al. |
| 5,792,922 A | 8/1998 | Moloney et al. |
| 5,797,955 A | 8/1998 | Walters |
| 5,804,546 A | 9/1998 | Hall et al. |
| 5,817,322 A | 10/1998 | Xu et al. |
| 5,824,650 A | 10/1998 | De Lacharriere et al. |
| 5,833,960 A | 11/1998 | Gers-Barlag et al. |
| 5,833,961 A | 11/1998 | Siegfried et al. |
| 5,837,270 A | 11/1998 | Burgess |
| 5,840,744 A | 11/1998 | Borgman |
| 5,840,771 A | 11/1998 | Oldham et al. |
| 5,843,411 A | 12/1998 | Hernandez et al. |
| 5,846,983 A | 12/1998 | Sandborn et al. |
| 5,849,042 A | 12/1998 | Lim et al. |
| 5,856,452 A | 1/1999 | Moloney et al. |
| 5,858,371 A | 1/1999 | Singh et al. |
| 5,865,347 A | 2/1999 | Welschoff |
| 5,866,040 A | 2/1999 | Nakama et al. |
| 5,869,529 A | 2/1999 | Sintov et al. |
| 5,871,720 A | 2/1999 | Gutierrez et al. |
| 5,877,216 A | 3/1999 | Place et al. |
| 5,879,469 A | 3/1999 | Avram et al. |
| 5,881,493 A | 3/1999 | Restive |
| 5,885,581 A | 3/1999 | Massand |
| 5,889,028 A | 3/1999 | Sandborn et al. |
| 5,889,054 A | 3/1999 | Yu et al. |
| 5,891,458 A | 4/1999 | Britton et al. |
| 5,902,574 A | 5/1999 | Stoner et al. |
| 5,902,789 A | 5/1999 | Stoltz |
| 5,905,092 A | 5/1999 | Osborne et al. |
| 5,910,382 A | 6/1999 | Goodenough et al. |
| 5,911,981 A | 6/1999 | Dahms et al. |
| 5,912,007 A | 6/1999 | Pan et al. |
| 5,914,122 A | 6/1999 | Otterbeck et al. |
| 5,914,310 A | 6/1999 | Li et al. |
| 5,922,331 A | 7/1999 | Mausner |

(56) References Cited

U.S. PATENT DOCUMENTS

| | | |
|---|---|---|
| 5,925,669 A | 7/1999 | Katz et al. |
| 5,948,682 A | 9/1999 | Moloney |
| 5,951,544 A | 9/1999 | Konwitz |
| 5,951,989 A | 9/1999 | Heymann |
| 5,951,993 A | 9/1999 | Scholz et al. |
| 5,952,373 A | 9/1999 | Lanzendorfer et al. |
| 5,952,392 A | 9/1999 | Katz et al. |
| 5,955,414 A | 9/1999 | Brown et al. |
| 5,959,161 A | 9/1999 | Kenmochi et al. |
| 5,961,957 A | 10/1999 | McAnalley |
| 5,961,998 A | 10/1999 | Arnaud et al. |
| 5,972,310 A | 10/1999 | Sachetto |
| 5,976,555 A | 11/1999 | Liu et al. |
| 5,980,904 A | 11/1999 | Leverett et al. |
| 5,990,100 A | 11/1999 | Rosenberg et al. |
| 5,993,846 A | 11/1999 | Friedman et al. |
| 6,001,341 A | 12/1999 | Genova et al. |
| 6,006,948 A | 12/1999 | Auer |
| 6,019,967 A | 2/2000 | Breton et al. |
| 6,024,942 A | 2/2000 | Tanner et al. |
| 6,030,630 A | 2/2000 | Fleury et al. |
| 6,033,647 A | 3/2000 | Touzan et al. |
| 6,039,936 A | 3/2000 | Restle et al. |
| 6,042,848 A | 3/2000 | Lawyer et al. |
| 6,045,779 A | 4/2000 | Mueller et al. |
| 6,071,536 A | 6/2000 | Suzuki et al. |
| 6,075,056 A | 6/2000 | Quigley, Jr. et al. |
| 6,080,394 A | 6/2000 | Lin et al. |
| 6,087,317 A | 7/2000 | Gee |
| 6,090,772 A | 7/2000 | Kaiser et al. |
| 6,093,408 A | 7/2000 | Hasenoehrl et al. |
| 6,096,756 A | 8/2000 | Crain et al. |
| 6,110,477 A | 8/2000 | Hernandez et al. |
| 6,110,966 A | 8/2000 | Pollock |
| 6,113,888 A | 9/2000 | Castro et al. |
| 6,116,466 A | 9/2000 | Gueret |
| 6,121,210 A | 9/2000 | Taylor |
| 6,126,920 A | 10/2000 | Jones et al. |
| 6,140,355 A | 10/2000 | Egidio et al. |
| 6,146,645 A | 11/2000 | Deckers et al. |
| 6,146,664 A | 11/2000 | Siddiqui |
| 6,162,834 A | 12/2000 | Sebillotte-Arnaud et al. |
| 6,165,455 A | 12/2000 | Torgerson et al. |
| 6,168,576 B1 | 1/2001 | Reynolds |
| 6,171,347 B1 | 1/2001 | Kunz et al. |
| 6,180,669 B1 | 1/2001 | Tamarkin |
| 6,183,762 B1 | 2/2001 | Deckers et al. |
| 6,186,367 B1 | 2/2001 | Harrold |
| 6,187,290 B1 | 2/2001 | Gilchrist et al. |
| 6,189,810 B1 | 2/2001 | Nerushai et al. |
| 6,190,365 B1 | 2/2001 | Abbott et al. |
| 6,204,285 B1 | 3/2001 | Fabiano et al. |
| 6,210,656 B1 | 4/2001 | Touzan et al. |
| 6,210,742 B1 | 4/2001 | Deckers et al. |
| 6,214,318 B1 | 4/2001 | Osipow et al. |
| 6,214,788 B1 | 4/2001 | Velazco et al. |
| 6,221,381 B1 | 4/2001 | Shelford et al. |
| 6,221,823 B1 | 4/2001 | Crisanti et al. |
| 6,224,888 B1 | 5/2001 | Vatter et al. |
| 6,231,837 B1 | 5/2001 | Stroud et al. |
| 6,232,315 B1 | 5/2001 | Shafer et al. |
| 6,251,369 B1 | 6/2001 | Stoltz |
| 6,258,374 B1 | 7/2001 | Friess et al. |
| 6,270,781 B1 * | 8/2001 | Gehlsen ............... 424/401 |
| 6,271,295 B1 | 8/2001 | Powell et al. |
| 6,274,150 B1 | 8/2001 | Simonnet et al. |
| 6,287,546 B1 | 9/2001 | Reich et al. |
| 6,294,550 B1 | 9/2001 | Place et al. |
| 6,299,023 B1 | 10/2001 | Arnone |
| 6,299,032 B1 | 10/2001 | Hamilton |
| 6,299,900 B1 | 10/2001 | Reed et al. |
| 6,305,578 B1 | 10/2001 | Hildebrandt et al. |
| 6,306,841 B1 | 10/2001 | Place et al. |
| 6,308,863 B1 | 10/2001 | Harman |
| 6,319,913 B1 | 11/2001 | Mak et al. |
| 6,328,950 B1 | 12/2001 | Franzke et al. |
| 6,328,982 B1 | 12/2001 | Shiroyama et al. |
| 6,333,362 B1 | 12/2001 | Lorant |
| 6,335,022 B1 | 1/2002 | Simonnet et al. |
| 6,341,717 B2 | 1/2002 | Auer |
| 6,344,218 B1 | 2/2002 | Dodd et al. |
| 6,348,229 B1 | 2/2002 | Eini et al. |
| 6,358,541 B1 | 3/2002 | Goodman |
| 6,364,854 B1 | 4/2002 | Ferrer et al. |
| 6,372,234 B1 | 4/2002 | Deckers et al. |
| 6,375,960 B1 | 4/2002 | Simonnet et al. |
| 6,383,471 B1 | 5/2002 | Chen et al. |
| 6,395,258 B1 | 5/2002 | Steer |
| 6,395,300 B1 | 5/2002 | Straub et al. |
| 6,403,061 B1 | 6/2002 | Candau et al. |
| 6,403,069 B1 | 6/2002 | Chopra et al. |
| 6,410,036 B1 | 6/2002 | De Rosa et al. |
| 6,423,323 B2 | 7/2002 | Neubourg |
| 6,428,772 B1 | 8/2002 | Singh et al. |
| 6,433,003 B1 | 8/2002 | Bobrove et al. |
| 6,433,024 B1 | 8/2002 | Popp et al. |
| 6,433,033 B1 | 8/2002 | Isobe et al. |
| 6,437,006 B1 | 8/2002 | Yoon et al. |
| 6,440,429 B1 | 8/2002 | Torizuka et al. |
| 6,447,801 B1 | 9/2002 | Salafsky et al. |
| 6,455,076 B1 | 9/2002 | Hahn et al. |
| 6,468,989 B1 | 10/2002 | Chang et al. |
| 6,479,058 B1 | 11/2002 | McCadden |
| 6,486,168 B1 | 11/2002 | Skwierczynski et al. |
| 6,488,947 B1 | 12/2002 | Bekele |
| 6,511,655 B1 | 1/2003 | Muller et al. |
| 6,514,487 B1 | 2/2003 | Barr |
| 6,524,594 B1 | 2/2003 | Santora et al. |
| 6,531,118 B1 | 3/2003 | Gonzalez et al. |
| 6,534,455 B1 | 3/2003 | Maurin et al. |
| 6,536,629 B2 | 3/2003 | van der Heijden |
| 6,544,530 B1 | 4/2003 | Friedman |
| 6,544,562 B2 | 4/2003 | Singh et al. |
| 6,547,063 B1 | 4/2003 | Zaveri et al. |
| 6,548,074 B1 | 4/2003 | Mohammadi |
| 6,562,355 B1 | 5/2003 | Renault |
| 6,566,350 B2 | 5/2003 | Ono et al. |
| 6,582,679 B2 | 6/2003 | Stein et al. |
| 6,582,710 B2 | 6/2003 | Deckers et al. |
| 6,589,509 B2 | 7/2003 | Keller et al. |
| 6,596,287 B2 | 7/2003 | Deckers et al. |
| 6,599,513 B2 | 7/2003 | Deckers et al. |
| 6,620,773 B1 | 9/2003 | Stork et al. |
| 6,638,981 B2 | 10/2003 | Williams et al. |
| 6,649,571 B1 | 11/2003 | Morgan |
| 6,649,574 B2 | 11/2003 | Cardis et al. |
| 6,672,483 B1 | 1/2004 | Roy |
| 6,682,726 B2 | 1/2004 | Marchesi et al. |
| 6,691,898 B2 | 2/2004 | Hurray et al. |
| 6,709,663 B2 | 3/2004 | Espinoza |
| 6,723,309 B1 | 4/2004 | Deane |
| 6,730,288 B1 | 5/2004 | Abram |
| 6,753,000 B2 | 6/2004 | Breton et al. |
| 6,753,167 B2 | 6/2004 | Moloney et al. |
| 6,762,158 B2 | 7/2004 | Lukenbach et al. |
| 6,765,001 B2 | 7/2004 | Gans et al. |
| 6,774,114 B2 | 8/2004 | Castiel et al. |
| 6,777,591 B1 | 8/2004 | Chaudhary et al. |
| 6,790,435 B1 | 9/2004 | Ma et al. |
| 6,796,973 B1 | 9/2004 | Contente et al. |
| RE38,623 E | 10/2004 | Hernandez et al. |
| 6,811,767 B1 | 11/2004 | Bosch et al. |
| 6,834,778 B2 | 12/2004 | Jinbo et al. |
| 6,843,390 B1 | 1/2005 | Bristor |
| 6,875,438 B2 | 4/2005 | Kraemer et al. |
| 6,881,271 B2 | 4/2005 | Ochiai |
| 6,890,567 B2 | 5/2005 | Nakatsu et al. |
| 6,902,737 B2 | 6/2005 | Quemin et al. |
| 6,911,211 B2 | 6/2005 | Eini et al. |
| 6,946,120 B2 | 9/2005 | Wai-Chiu So et al. |
| 6,946,139 B2 | 9/2005 | Henning |
| 6,951,654 B2 | 10/2005 | Malcolm et al. |
| 6,955,816 B2 | 10/2005 | Klysz |
| 6,956,062 B2 | 10/2005 | Beilfuss et al. |

(56) References Cited

U.S. PATENT DOCUMENTS

| | | |
|---|---|---|
| 6,958,154 B2 | 10/2005 | Andolino Brandt et al. |
| 6,967,023 B1 | 11/2005 | Eini et al. |
| 6,968,982 B1 | 11/2005 | Burns |
| 6,969,521 B1 | 11/2005 | Gonzalez et al. |
| RE38,964 E | 1/2006 | Shillington |
| 6,994,863 B2 | 2/2006 | Eini et al. |
| 7,002,486 B2 | 2/2006 | Lawrence |
| 7,014,844 B2 | 3/2006 | Mahalingam et al. |
| 7,021,499 B2 | 4/2006 | Hansen et al. |
| 7,029,659 B2 | 4/2006 | Abram |
| 7,060,253 B1 | 6/2006 | Mundschenk |
| 7,078,058 B2 | 7/2006 | Jones et al. |
| 7,083,799 B1 | 8/2006 | Giacomoni |
| 7,137,536 B2 | 11/2006 | Walters et al. |
| 7,195,135 B1 | 3/2007 | Garcia |
| 7,222,802 B2 | 5/2007 | Sweeton |
| 7,225,518 B2 | 6/2007 | Eidenschink et al. |
| 7,226,230 B2 | 6/2007 | Liberatore |
| 7,235,251 B2 | 6/2007 | Hamer et al. |
| 7,270,828 B2 | 9/2007 | Masuda et al. |
| 7,455,195 B2 | 11/2008 | Mekata |
| 7,497,354 B2 | 3/2009 | Decottignies et al. |
| 7,575,739 B2 | 8/2009 | Tamarkin et al. |
| 7,645,803 B2 | 1/2010 | Tamarkin et al. |
| 7,654,415 B2 | 2/2010 | van der Heijden |
| 7,682,623 B2 | 3/2010 | Eini et al. |
| 7,700,076 B2 | 4/2010 | Tamarkin et al. |
| 7,704,518 B2 | 4/2010 | Tamarkin et al. |
| 7,793,807 B2 | 9/2010 | Goujon et al. |
| 7,820,145 B2 | 10/2010 | Tamarkin et al. |
| 7,960,416 B2 | 6/2011 | Sato et al. |
| 2001/0006654 A1 | 7/2001 | Cannell et al. |
| 2001/0027218 A1 | 10/2001 | Stern et al. |
| 2001/0027981 A1 | 10/2001 | Yquel |
| 2001/0036450 A1 | 11/2001 | Verite et al. |
| 2001/0054574 A1 | 12/2001 | Navarro |
| 2002/0002151 A1 | 1/2002 | Ono et al. |
| 2002/0004063 A1 | 1/2002 | Zhang |
| 2002/0013481 A1 | 1/2002 | Schonrock et al. |
| 2002/0015721 A1 | 2/2002 | Simonnet et al. |
| 2002/0032171 A1 | 3/2002 | Chen et al. |
| 2002/0035046 A1 | 3/2002 | Lukenbach et al. |
| 2002/0035070 A1 | 3/2002 | Gardlik et al. |
| 2002/0035087 A1 | 3/2002 | Barclay |
| 2002/0035182 A1 | 3/2002 | L'Alloret et al. |
| 2002/0039591 A1 | 4/2002 | Dahle |
| 2002/0044659 A1 | 4/2002 | Ohta |
| 2002/0045659 A1 | 4/2002 | Michelet et al. |
| 2002/0048798 A1 | 4/2002 | Avery et al. |
| 2002/0058010 A1 | 5/2002 | Picard-Lesboueyries et al. |
| 2002/0072544 A1 | 6/2002 | Miller et al. |
| 2002/0090386 A1 | 7/2002 | Haslwanter et al. |
| 2002/0098215 A1 | 7/2002 | Douin et al. |
| 2002/0111281 A1 | 8/2002 | Vishnupad |
| 2002/0117516 A1 | 8/2002 | Lasserre et al. |
| 2002/0134376 A1 | 9/2002 | Castro et al. |
| 2002/0136755 A1 | 9/2002 | Tyrrell et al. |
| 2002/0143188 A1 | 10/2002 | Garvey et al. |
| 2002/0153390 A1 | 10/2002 | Vlodek |
| 2002/0165170 A1 | 11/2002 | Wilson et al. |
| 2002/0182162 A1 | 12/2002 | Shahinpoor et al. |
| 2002/0187181 A1 | 12/2002 | Godbey et al. |
| 2002/0198136 A1 | 12/2002 | Mak et al. |
| 2003/0006193 A1 | 1/2003 | Ikeda et al. |
| 2003/0031693 A1 | 2/2003 | Breton et al. |
| 2003/0053961 A1 | 3/2003 | Eccard |
| 2003/0077297 A1 | 4/2003 | Chen et al. |
| 2003/0078172 A1 | 4/2003 | Guiramand et al. |
| 2003/0114520 A1 | 6/2003 | Pereira et al. |
| 2003/0118515 A1 | 6/2003 | Jew et al. |
| 2003/0130247 A1 | 7/2003 | Gans et al. |
| 2003/0175232 A1 | 9/2003 | Elliott et al. |
| 2003/0175315 A1 | 9/2003 | Yoo et al. |
| 2003/0180347 A1 | 9/2003 | Young et al. |
| 2003/0185839 A1 | 10/2003 | Podolsky |
| 2003/0194379 A1 | 10/2003 | Brugger et al. |
| 2003/0195128 A1 | 10/2003 | Deckman et al. |
| 2003/0206955 A1 | 11/2003 | Sonneville-Aubrun et al. |
| 2003/0215472 A1 | 11/2003 | Bonda et al. |
| 2004/0018228 A1 | 1/2004 | Fischell et al. |
| 2004/0028752 A1 | 2/2004 | Kamm et al. |
| 2004/0038912 A1 | 2/2004 | Michelet et al. |
| 2004/0053797 A1 | 3/2004 | Chen et al. |
| 2004/0058878 A1 | 3/2004 | Walker |
| 2004/0063787 A1 | 4/2004 | Villanueva |
| 2004/0067970 A1 | 4/2004 | Foster et al. |
| 2004/0072638 A1 | 4/2004 | Enos et al. |
| 2004/0076651 A1 | 4/2004 | Brocks et al. |
| 2004/0078896 A1 | 4/2004 | Hellyer et al. |
| 2004/0105825 A1 | 6/2004 | Henning |
| 2004/0120917 A1 | 6/2004 | Perrier et al. |
| 2004/0127554 A1 | 7/2004 | Ghisalberti |
| 2004/0138179 A1 | 7/2004 | Goldstein et al. |
| 2004/0151671 A1 | 8/2004 | Abram et al. |
| 2004/0151756 A1 | 8/2004 | Richards et al. |
| 2004/0161447 A1 | 8/2004 | Paul |
| 2004/0184992 A1 | 9/2004 | Abram |
| 2004/0185123 A1 | 9/2004 | Mazzio et al. |
| 2004/0191196 A1 | 9/2004 | Tamarkin |
| 2004/0192754 A1 | 9/2004 | Shapira et al. |
| 2004/0195276 A1 | 10/2004 | Fuchs |
| 2004/0197276 A1 | 10/2004 | Takase et al. |
| 2004/0197295 A1 | 10/2004 | Riedel et al. |
| 2004/0219122 A1 | 11/2004 | Masuda et al. |
| 2004/0219176 A1 | 11/2004 | Dominguez |
| 2004/0220187 A1 | 11/2004 | Stephenson et al. |
| 2004/0229813 A1 | 11/2004 | DiPiano et al. |
| 2004/0234475 A1 | 11/2004 | Lannibois-Drean et al. |
| 2004/0241099 A1 | 12/2004 | Popp et al. |
| 2004/0247531 A1 | 12/2004 | Riedel et al. |
| 2004/0253275 A1 | 12/2004 | Eini et al. |
| 2004/0258627 A1 | 12/2004 | Riedel et al. |
| 2004/0265240 A1 | 12/2004 | Tamarkin et al. |
| 2005/0002976 A1 | 1/2005 | Wu |
| 2005/0013853 A1 | 1/2005 | Gil-Ad et al. |
| 2005/0031547 A1 | 2/2005 | Tamarkin et al. |
| 2005/0042182 A1 | 2/2005 | Arkin et al. |
| 2005/0054991 A1 | 3/2005 | Tobyn et al. |
| 2005/0069566 A1 | 3/2005 | Tamarkin et al. |
| 2005/0074414 A1 | 4/2005 | Tamarkin et al. |
| 2005/0075407 A1 | 4/2005 | Tamarkin et al. |
| 2005/0079139 A1 | 4/2005 | Jacques et al. |
| 2005/0084551 A1 | 4/2005 | Jensen et al. |
| 2005/0085843 A1 | 4/2005 | Opolski et al. |
| 2005/0101936 A1 | 5/2005 | Gonzales et al. |
| 2005/0106197 A1 | 5/2005 | Blin et al. |
| 2005/0123494 A1 | 6/2005 | Swaile et al. |
| 2005/0123496 A1 | 6/2005 | Shah et al. |
| 2005/0186142 A1 | 8/2005 | Tamarkin et al. |
| 2005/0186147 A1 | 8/2005 | Tamarkin et al. |
| 2005/0189377 A1 | 9/2005 | Lanzendorfer et al. |
| 2005/0196414 A1 | 9/2005 | Dake et al. |
| 2005/0205086 A1 | 9/2005 | Tamarkin et al. |
| 2005/0207837 A1 | 9/2005 | Kosh et al. |
| 2005/0222090 A1 | 10/2005 | Cheng et al. |
| 2005/0232869 A1 | 10/2005 | Tamarkin et al. |
| 2005/0244342 A1 | 11/2005 | Friedman et al. |
| 2005/0244354 A1 | 11/2005 | Speron |
| 2005/0245902 A1 | 11/2005 | Cornish et al. |
| 2005/0252995 A1 | 11/2005 | Westphal et al. |
| 2005/0255048 A1 | 11/2005 | Hirsh et al. |
| 2005/0258189 A1 | 11/2005 | Peterson et al. |
| 2005/0266035 A1 | 12/2005 | Healy et al. |
| 2005/0268416 A1 | 12/2005 | Sommers |
| 2005/0271596 A1 | 12/2005 | Friedman et al. |
| 2005/0271598 A1 | 12/2005 | Friedman et al. |
| 2005/0276836 A1 | 12/2005 | Wilson et al. |
| 2005/0281755 A1 | 12/2005 | Zarif et al. |
| 2005/0281766 A1 | 12/2005 | Martin et al. |
| 2005/0285912 A1 | 12/2005 | Delametter et al. |
| 2005/0287081 A1 | 12/2005 | Aust et al. |
| 2006/0008432 A1 | 1/2006 | Scarampi et al. |
| 2006/0018937 A1 | 1/2006 | Friedman et al. |
| 2006/0018938 A1 | 1/2006 | Neubourg |

(56) References Cited

U.S. PATENT DOCUMENTS

| | | |
|---|---|---|
| 2006/0029565 A1 | 2/2006 | Xu et al. |
| 2006/0051301 A1 | 3/2006 | Galopin et al. |
| 2006/0054634 A1 | 3/2006 | Mekata |
| 2006/0057168 A1 | 3/2006 | Larm et al. |
| 2006/0088561 A1 | 4/2006 | Eini et al. |
| 2006/0099151 A1 | 5/2006 | Neubourg |
| 2006/0108377 A1 | 5/2006 | Glynn et al. |
| 2006/0110418 A1 | 5/2006 | Johnson |
| 2006/0114745 A1 | 6/2006 | Ollmann et al. |
| 2006/0121073 A1 | 6/2006 | Goyal et al. |
| 2006/0140984 A1 | 6/2006 | Tamarkin et al. |
| 2006/0140990 A1 | 6/2006 | Bortz et al. |
| 2006/0160713 A1 | 7/2006 | Sekine et al. |
| 2006/0165616 A1 | 7/2006 | Brock et al. |
| 2006/0177392 A1 | 8/2006 | Walden |
| 2006/0193789 A1 | 8/2006 | Tamarkin et al. |
| 2006/0193813 A1 | 8/2006 | Simonnet |
| 2006/0204446 A1 | 9/2006 | Lulla et al. |
| 2006/0222675 A1 | 10/2006 | Sabnis et al. |
| 2006/0233721 A1 | 10/2006 | Tamarkin et al. |
| 2006/0239937 A2 | 10/2006 | Neubourg |
| 2006/0251684 A1 | 11/2006 | Annis et al. |
| 2006/0254597 A1 | 11/2006 | Thompson |
| 2006/0263323 A1 | 11/2006 | Hoang et al. |
| 2006/0269485 A1 | 11/2006 | Friedman et al. |
| 2006/0272199 A1 | 12/2006 | Licciardello et al. |
| 2006/0275218 A1 | 12/2006 | Tamarkin et al. |
| 2006/0275221 A1 | 12/2006 | Tamarkin et al. |
| 2006/0285912 A1 | 12/2006 | Eini et al. |
| 2006/0292080 A1 | 12/2006 | Abram et al. |
| 2007/0009607 A1 | 1/2007 | Jones |
| 2007/0020213 A1 | 1/2007 | Tamarkin et al. |
| 2007/0020304 A1 | 1/2007 | Tamarkin et al. |
| 2007/0027055 A1 | 2/2007 | Koivisto et al. |
| 2007/0036831 A1 | 2/2007 | Baker |
| 2007/0059253 A1 | 3/2007 | Popp et al. |
| 2007/0069046 A1 | 3/2007 | Eini et al. |
| 2007/0071688 A1 | 3/2007 | Illel et al. |
| 2007/0098647 A1 | 5/2007 | Neubourg |
| 2007/0134174 A1 | 6/2007 | Irwin et al. |
| 2007/0140999 A1 | 6/2007 | Puglia et al. |
| 2007/0142263 A1 | 6/2007 | Stahl et al. |
| 2007/0148112 A1 | 6/2007 | Dingley et al. |
| 2007/0148194 A1 | 6/2007 | Amiji et al. |
| 2007/0154402 A1 | 7/2007 | Trumbore et al. |
| 2007/0160548 A1 | 7/2007 | Riccardi et al. |
| 2007/0224143 A1 | 9/2007 | Konis |
| 2007/0237724 A1 | 10/2007 | Abram et al. |
| 2007/0253911 A1 | 11/2007 | Tamarkin et al. |
| 2007/0264317 A1 | 11/2007 | Yosha et al. |
| 2007/0271235 A1 | 11/2007 | Frank et al. |
| 2007/0280891 A1 | 12/2007 | Tamarkin et al. |
| 2007/0281999 A1 | 12/2007 | Fox et al. |
| 2007/0292355 A1 | 12/2007 | Tamarkin et al. |
| 2007/0292359 A1 | 12/2007 | Friedman et al. |
| 2007/0292461 A1 | 12/2007 | Tamarkin et al. |
| 2008/0008397 A1 | 1/2008 | Kisilev |
| 2008/0015263 A1 | 1/2008 | Bolotin et al. |
| 2008/0015271 A1 | 1/2008 | Abram et al. |
| 2008/0031907 A1 | 2/2008 | Tamarkin et al. |
| 2008/0031908 A1 | 2/2008 | Aubrun-Sonneville et al. |
| 2008/0035155 A1 | 2/2008 | Dahl |
| 2008/0044444 A1 | 2/2008 | Tamarkin et al. |
| 2008/0058055 A1 | 3/2008 | LeMay et al. |
| 2008/0063682 A1 | 3/2008 | Cashman et al. |
| 2008/0069779 A1 | 3/2008 | Tamarkin et al. |
| 2008/0131378 A1 | 6/2008 | Keller et al. |
| 2008/0138293 A1 | 6/2008 | Tamarkin et al. |
| 2008/0138296 A1 | 6/2008 | Tamarkin et al. |
| 2008/0152596 A1 | 6/2008 | Friedman et al. |
| 2008/0153789 A1 | 6/2008 | Dmowski et al. |
| 2008/0166303 A1 | 7/2008 | Tamarkin et al. |
| 2008/0167376 A1 | 7/2008 | Bar-Or et al. |
| 2008/0181854 A1 | 7/2008 | Eini et al. |
| 2008/0188445 A1 | 8/2008 | Muldoon et al. |
| 2008/0188446 A1 | 8/2008 | Muldoon et al. |
| 2008/0193762 A1 | 8/2008 | Dubertret et al. |
| 2008/0206155 A1 | 8/2008 | Tamarkin et al. |
| 2008/0206159 A1 | 8/2008 | Tamarkin et al. |
| 2008/0206161 A1 | 8/2008 | Tamarkin et al. |
| 2008/0241079 A1 | 10/2008 | Neubourg |
| 2008/0253973 A1 | 10/2008 | Tamarkin et al. |
| 2008/0255498 A1 | 10/2008 | Houle |
| 2008/0260655 A1 | 10/2008 | Tamarkin et al. |
| 2008/0292560 A1 | 11/2008 | Tamarkin et al. |
| 2008/0299220 A1 | 12/2008 | Tamarkin et al. |
| 2008/0311167 A1 | 12/2008 | Oronsky et al. |
| 2008/0317679 A1 | 12/2008 | Tamarkin et al. |
| 2009/0041680 A1 | 2/2009 | Tamarkin et al. |
| 2009/0068118 A1 | 3/2009 | Eini et al. |
| 2009/0093514 A1 | 4/2009 | Statham et al. |
| 2009/0130029 A1 | 5/2009 | Tamarkin et al. |
| 2009/0131488 A1 | 5/2009 | Harel et al. |
| 2009/0175799 A1 | 7/2009 | Tamarkin et al. |
| 2009/0180970 A1 | 7/2009 | Tamarkin et al. |
| 2009/0291917 A1 | 11/2009 | Akama et al. |
| 2009/0317338 A1 | 12/2009 | Tamarkin et al. |
| 2010/0111879 A1 | 5/2010 | Tamarkin et al. |
| 2010/0221194 A1 | 9/2010 | Loupenok |
| 2011/0002857 A1 | 1/2011 | Tamarkin et al. |
| 2011/0002969 A1 | 1/2011 | Serraima et al. |
| 2011/0212033 A1 | 9/2011 | Tamarkin et al. |
| 2011/0268665 A1 | 11/2011 | Tamarkin et al. |
| 2012/0128598 A1 | 5/2012 | Trumbore et al. |

FOREIGN PATENT DOCUMENTS

| | | |
|---|---|---|
| CH | 639913 | 12/1983 |
| DE | 1 882 100 | 11/1963 |
| DE | 1926796 | 11/1965 |
| DE | 4140474 | 6/1993 |
| DE | 10009233 | 8/2000 |
| DE | 10138495 | 2/2003 |
| DE | 102004016710 | 10/2005 |
| DE | 2 608 226 | 9/2007 |
| EP | 0 156 507 | 10/1985 |
| EP | 0 186 453 | 7/1986 |
| EP | 0 211 550 | 2/1987 |
| EP | 0 214 865 | 3/1987 |
| EP | 0 216 856 | 4/1987 |
| EP | 0 270 316 | 6/1988 |
| EP | 0 297 436 | 1/1989 |
| EP | 0 326 196 | 8/1989 |
| EP | 0 336 812 | 10/1989 |
| EP | 0 391 124 | 10/1990 |
| EP | 0 404 376 | 12/1990 |
| EP | 0 414 920 | 3/1991 |
| EP | 0 484 530 | 5/1992 |
| EP | 0 485 299 | 5/1992 |
| EP | 0 488 089 | 6/1992 |
| EP | 0 504 301 | 9/1992 |
| EP | 0 528 190 | 2/1993 |
| EP | 0 535 327 | 4/1993 |
| EP | 0 552 612 | 7/1993 |
| EP | 0 569 773 | 11/1993 |
| EP | 0 598 412 | 5/1994 |
| EP | 0 662 431 | 7/1995 |
| EP | 0 676 198 | 10/1995 |
| EP | 0 738 516 | 10/1996 |
| EP | 0 757 959 | 2/1997 |
| EP | 0 824 911 | 2/1998 |
| EP | 0 829 259 | 3/1998 |
| EP | 0 928 608 | 7/1999 |
| EP | 0 979 654 | 2/2000 |
| EP | 0 993 827 | 4/2000 |
| EP | 1 025 836 | 8/2000 |
| EP | 1 055 425 | 11/2000 |
| EP | 0 506 197 | 7/2001 |
| EP | 1 215 258 | 6/2002 |
| EP | 1 287 813 | 3/2003 |
| EP | 1 308 169 | 5/2003 |
| EP | 1 375 386 | 1/2004 |
| EP | 1 428 521 | 6/2004 |
| EP | 1 438 946 | 7/2004 |

(56) References Cited

FOREIGN PATENT DOCUMENTS

| | | |
|---|---|---|
| EP | 1 189 579 | 9/2004 |
| EP | 1 475 381 | 11/2004 |
| EP | 1 483 001 | 12/2004 |
| EP | 1 500 385 | 1/2005 |
| EP | 1 537 916 | 6/2005 |
| EP | 1 600 185 | 11/2005 |
| EP | 1 734 927 | 12/2006 |
| EP | 1 758 547 | 3/2007 |
| EP | 1 584 324 | 11/2007 |
| EP | 1 889 609 | 2/2008 |
| FR | 2 591 331 | 6/1987 |
| FR | 2 640 942 | 6/1990 |
| FR | 2 736 824 | 1/1997 |
| FR | 2 774 595 | 8/1999 |
| FR | 2 789 371 | 8/2000 |
| FR | 2 793 479 | 11/2000 |
| FR | 2 814 959 | 4/2002 |
| FR | 2 833 246 | 6/2003 |
| FR | 2 840 903 | 12/2003 |
| FR | 2 843 373 | 2/2004 |
| FR | 2 845 672 | 4/2004 |
| FR | 2 848 998 | 6/2004 |
| FR | 2 860 976 | 4/2005 |
| FR | 2 915 891 | 11/2008 |
| GB | 808 104 | 1/1959 |
| GB | 808 105 | 1/1959 |
| GB | 922 930 | 4/1963 |
| GB | 933 486 | 8/1963 |
| GB | 998 490 | 7/1965 |
| GB | 1 026 831 | 4/1966 |
| GB | 1 033 299 | 6/1966 |
| GB | 1 081 949 | 9/1967 |
| GB | 1 121 358 | 7/1968 |
| GB | 1 162 684 | 8/1969 |
| GB | 1 170 152 | 11/1969 |
| GB | 1 201 918 | 8/1970 |
| GB | 1 347 950 | 2/1974 |
| GB | 1 351 761 | 5/1974 |
| GB | 1 351 762 | 5/1974 |
| GB | 1 353 381 | 5/1974 |
| GB | 1 376 649 | 12/1974 |
| GB | 1 397 285 | 6/1975 |
| GB | 1 408 036 | 10/1975 |
| GB | 1 457 671 | 12/1976 |
| GB | 1 489 672 | 10/1977 |
| GB | 2 004 746 | 4/1979 |
| GB | 1 561 423 | 2/1980 |
| GB | 2 114 580 | 8/1983 |
| GB | 2 153 686 | 8/1985 |
| GB | 2 172 298 | 9/1986 |
| GB | 2 206 099 | 12/1988 |
| GB | 2 166 651 | 5/1996 |
| GB | 2 337 461 | 11/1999 |
| GB | 2 367 809 | 4/2002 |
| GB | 2 406 330 | 3/2005 |
| GB | 2 406 791 | 4/2005 |
| IL | 49491 | 9/1979 |
| IL | 152 486 | 5/2003 |
| JP | 60001113 | 4/1978 |
| JP | 55069682 | 5/1980 |
| JP | 57044429 | 3/1982 |
| JP | 56039815 | 4/1984 |
| JP | 61275395 | 12/1986 |
| JP | 62241701 | 10/1987 |
| JP | 63119420 | 5/1988 |
| JP | 1100111 | 4/1989 |
| JP | 1156906 | 6/1989 |
| JP | 2184614 | 7/1990 |
| JP | 2255890 | 10/1990 |
| JP | 4282311 | 10/1992 |
| JP | 4312521 | 11/1992 |
| JP | 5070340 | 3/1993 |
| JP | 5213734 | 8/1993 |
| JP | 6100414 | 4/1994 |
| JP | H06-263630 | 6/1994 |
| JP | 6329532 | 11/1994 |
| JP | 2007/155667 | 6/1995 |
| JP | 7215835 | 8/1995 |
| JP | 2008/040899 | 2/1996 |
| JP | 8501529 | 2/1996 |
| JP | 8119831 | 5/1996 |
| JP | 8165218 | 6/1996 |
| JP | 8277209 | 10/1996 |
| JP | 09 084855 | 3/1997 |
| JP | 9099553 | 4/1997 |
| JP | 9110636 | 4/1997 |
| JP | 10114619 | 5/1998 |
| JP | 3050289 | 9/1998 |
| JP | 2010/332456 | 12/1998 |
| JP | 11501045 | 1/1999 |
| JP | 11250543 | 9/1999 |
| JP | 2000/017174 | 1/2000 |
| JP | 2000/080017 | 3/2000 |
| JP | 2000/128734 | 5/2000 |
| JP | 2000/191429 | 7/2000 |
| JP | 2000/239140 | 9/2000 |
| JP | 2000/351726 | 12/2000 |
| JP | 2000/354623 | 12/2000 |
| JP | 2001/002526 | 1/2001 |
| JP | 2001/019606 | 1/2001 |
| JP | 2001/072963 | 3/2001 |
| JP | 2002/012513 | 1/2002 |
| JP | 2002/047136 | 2/2002 |
| JP | 2002/524490 | 8/2002 |
| JP | 2002/302419 | 10/2002 |
| JP | 2003/012511 | 1/2003 |
| JP | 2003/055146 | 2/2003 |
| JP | 2004/047136 | 2/2004 |
| JP | 2004/250435 | 9/2004 |
| JP | 2004/348277 | 12/2004 |
| JP | 2005/314323 | 11/2005 |
| JP | 2005/350378 | 12/2005 |
| JP | 2006/008574 | 1/2006 |
| JP | 2006/036317 | 2/2006 |
| JP | 2006/103799 | 4/2006 |
| JP | 2006525145 | 11/2006 |
| JP | 2007/131539 | 5/2007 |
| JP | 2007326996 | 12/2007 |
| KR | 143232 | 7/1998 |
| KR | 2001/003063 | 1/2001 |
| RU | 2277501 | 6/2006 |
| UA | 66796 | 6/2004 |
| WO | 82/01821 | 6/1982 |
| WO | 86/05389 | 9/1986 |
| WO | 88/01502 | 3/1988 |
| WO | 88/01863 | 3/1988 |
| WO | 88/08316 | 11/1988 |
| WO | 89/06537 | 7/1989 |
| WO | 90/05774 | 5/1990 |
| WO | 91/11991 | 8/1991 |
| WO | 92/00077 | 1/1992 |
| WO | 92/05142 | 4/1992 |
| WO | 92/05763 | 4/1992 |
| WO | 92/11839 | 7/1992 |
| WO | 93/25189 | 12/1993 |
| WO | 94/06440 | 3/1994 |
| WO | 96/03115 | 2/1996 |
| WO | 96/19921 | 7/1996 |
| WO | 96/24325 | 8/1996 |
| WO | 96/26711 | 9/1996 |
| WO | 96/27376 | 9/1996 |
| WO | 96/39119 | 12/1996 |
| WO | 97/03638 | 2/1997 |
| WO | 97/39745 | 10/1997 |
| WO | 98/17282 | 4/1998 |
| WO | 98/18472 | 5/1998 |
| WO | 98/19654 | 5/1998 |
| WO | 98/21955 | 5/1998 |
| WO | 98/23291 | 6/1998 |
| WO | 98/36733 | 8/1998 |
| WO | 98/52536 | 11/1998 |
| WO | 99/08649 | 2/1999 |
| WO | 99/20250 | 4/1999 |
| WO | 99/37282 | 7/1999 |

(56) References Cited

FOREIGN PATENT DOCUMENTS

| | | |
|---|---|---|
| WO | 99/53923 | 10/1999 |
| WO | 00/09082 | 2/2000 |
| WO | 00/15193 | 3/2000 |
| WO | 00/23051 | 4/2000 |
| WO | 00/33825 | 6/2000 |
| WO | 00/38731 | 7/2000 |
| WO | 00/61076 | 10/2000 |
| WO | 00/76461 | 12/2000 |
| WO | 01/05366 | 1/2001 |
| WO | 01/08681 | 2/2001 |
| WO | 01/10961 | 2/2001 |
| WO | 01/53198 | 7/2001 |
| WO | 01/54212 | 7/2001 |
| WO | 01/54679 | 8/2001 |
| WO | 01/62209 | 8/2001 |
| WO | 01/70242 | 9/2001 |
| WO | 01/82880 | 11/2001 |
| WO | 01/82890 | 11/2001 |
| WO | 01/85102 | 11/2001 |
| WO | 01/85128 | 11/2001 |
| WO | 01/95728 | 12/2001 |
| WO | 02/00820 | 1/2002 |
| WO | 02/15860 | 2/2002 |
| WO | 02/15873 | 2/2002 |
| WO | 02/28435 | 4/2002 |
| WO | 02/41847 | 5/2002 |
| WO | 02/43490 | 6/2002 |
| WO | 02/062324 | 8/2002 |
| WO | 02/078667 | 10/2002 |
| WO | 02/087519 | 11/2002 |
| WO | 03/000223 | 1/2003 |
| WO | 03/002082 | 1/2003 |
| WO | 03/013984 | 2/2003 |
| WO | 03/051294 | 6/2003 |
| WO | 03/053292 | 7/2003 |
| WO | 03/055445 | 7/2003 |
| WO | 03/055454 | 7/2003 |
| WO | 03/070301 | 8/2003 |
| WO | 03/071995 | 9/2003 |
| WO | 03/075851 | 9/2003 |
| WO | 03/092641 | 11/2003 |
| WO | 03/097002 | 11/2003 |
| WO | 2004/017962 | 3/2004 |
| WO | 2004/037197 | 5/2004 |
| WO | 2004/037225 | 5/2004 |
| WO | 2004/003284 | 8/2004 |
| WO | 2004/064769 | 8/2004 |
| WO | 2004/064833 | 8/2004 |
| WO | 2004/071479 | 8/2004 |
| WO | 2004/078158 | 9/2004 |
| WO | 2004/078896 | 9/2004 |
| WO | 2004/093895 | 11/2004 |
| WO | 2004/112780 | 12/2004 |
| WO | 2005/011567 | 2/2005 |
| WO | 2005/018530 | 3/2005 |
| WO | 2005/032522 | 4/2005 |
| WO | 2005/044219 | 5/2005 |
| WO | 2005/063224 | 7/2005 |
| WO | 2005/065652 | 7/2005 |
| WO | 2005/076697 | 8/2005 |
| WO | 2005/097068 | 10/2005 |
| WO | 2005/102282 | 11/2005 |
| WO | 2005/102539 | 11/2005 |
| WO | 2005/117813 | 12/2005 |
| WO | 2006/003481 | 1/2006 |
| WO | 2006/010589 | 2/2006 |
| WO | 2006/011046 | 2/2006 |
| WO | 2006/020682 | 2/2006 |
| WO | 2006/028339 | 3/2006 |
| WO | 2006/031271 | 3/2006 |
| WO | 2006/045170 | 5/2006 |
| WO | 2006/079632 | 8/2006 |
| WO | 2006/081327 | 8/2006 |
| WO | 2006/091229 | 8/2006 |
| WO | 2006/100485 | 9/2006 |
| WO | 2006/120682 | 11/2006 |
| WO | 2006/121610 | 11/2006 |
| WO | 2006/122158 | 11/2006 |
| WO | 2006/129161 | 12/2006 |
| WO | 2006/131784 | 12/2006 |
| WO | 2007/007208 | 1/2007 |
| WO | 2007/012977 | 2/2007 |
| WO | 2007/023396 | 3/2007 |
| WO | 2007/031621 | 3/2007 |
| WO | 2007/039825 | 4/2007 |
| WO | 2007/050543 | 5/2007 |
| WO | 2007/054818 | 5/2007 |
| WO | 2007/072216 | 6/2007 |
| WO | 2007/085899 | 8/2007 |
| WO | 2007/085902 | 8/2007 |
| WO | 2007/099396 | 9/2007 |
| WO | 2007/111962 | 10/2007 |
| WO | 2008/008397 | 1/2008 |
| WO | 2008/010963 | 1/2008 |
| WO | 2008/038147 | 4/2008 |
| WO | 2008/041045 | 4/2008 |
| WO | 2008/075207 | 6/2008 |
| WO | 2008/087148 | 7/2008 |
| WO | 2008/110872 | 9/2008 |
| WO | 2008/152444 | 12/2008 |
| WO | 2009/007785 | 1/2009 |
| WO | 2009/069006 | 6/2009 |
| WO | 2009/072007 | 6/2009 |
| WO | 2009/087578 | 7/2009 |
| WO | 2009/090495 | 7/2009 |
| WO | 2009/090558 | 7/2009 |
| WO | 2009/098595 | 8/2009 |
| WO | 2011/039637 | 4/2011 |
| WO | 2011/039638 | 4/2011 |

OTHER PUBLICATIONS

"Reaction Rate" Accessed at en.wikipedia.org/wiki/Reaction_rate on Dec. 18, 2011, 6 pages.
'Niram Chemicals' [online]. Niram Chemicals, [retrieved on Jul. 17, 2012]. Retrieved from the Internet: <URL: http://www.indiamart.com/niramchemicals/chemicals.html>, 7 pages.
'Surfactant' [online]. Wikipedia, 2010, [retrieved on Oct. 24, 2010]. Retrieved from the Internet: <URL: http://en.wikipedia.org/wiki/Surfactant>, 7 pages.
Adachi, Shuji. "Storage and Oxidative Stability of O/W/ Nano-emulsions." Foods Food Ingredients. J. Jpn. vol. 209, No. 11. 2004. 1 page.
Alcohol SDA 40B.http://www.pharmco-prod.com/pages/MSDS/SDA.sub.--40B.sub.--200.pdf Accessed Dec. 9, 2008, 2 pages.
Ambrose, Ursula et al., "In Vitro Studies of Water Activity and Bacterial Growth Inhibition of Sucrose-Polyethylene Glycol 400-Hydrogen Peroxide and Xylose-Polyethylene Glycol 400-Hydrogen Peroxide Pastes Used to Treat Infected Wounds,"Antimicrobial Agents and Chemotherapy, vol. 35, No. 9, pp. 1799-1803, 1991.
Anton, N. et al. "Water-in-Oil Nano-Emulsion Formation by the phase inversion Temperature Method: A Novel and General Concept, a New Template for Nanoencapsulation," *Proceedings of the 33rd Annual Meeting and Exposition of the Controlled Release Society*, Jul. 2006, Vienna, Austria, 2 pages.
Arct et al., "Common Cosmetic Hydrophilic Ingredients as Penetration Modifiers of Flavonoids", International Journal of Cosmetic Science, 24(6):357-366 (2002)—Abstract, 1 page.
Arisan, http://www.arisankimya.com/kozmetik.htm Accessed Dec. 10, 2008, 8 pages.
Augsburger, Larry L. et al. "Bubble Size Analysis of High Consistency Aerosol Foams and Its Relationship to Foam Rheology. Effects of Container Emptying, Propellant Type, and Time." Journal of Pharmaceutical Sciences. vol. 57, No. 4. Apr. 1968. pp. 624-631.
Austria, et al., "Stability of Vitamin C Derivatives in Solution and Topical Formulations", Journal of Pharmaceutical and Biomedical Analysis, 15:795-801 (1997).
Barry and Badal, "Stability of minocycline, doxycycline, and tetracycline stored in agar plates and microdilution trays," *Current Microbiology*, 1978, 1:33-36.
Barry, B.W. et al, Comparative bio-availability and activity of proprietary topical corticosteroid preparations: vasoconstrictor assays on thirty-one ointments, British Journal of Dermatology, 93, 563-571, 1975.

(56) References Cited

OTHER PUBLICATIONS

Benet, et al., Application of NMR for the Determination of HLB Values of Nonionic Surfactants, Journal of the American Oil Chemists Society, vol. 49, 1972, 499-500.

Bernstein, et al., Effects of the Immunomodulating Agent R837 on Acute and Latent Herpes Simplex Virus Type 2 Invections, Antimicrobial Agents and Chemotherapy, 33(9):1511-1515 (1989).

Blute, "Phase behavior of alkyl glycerol ether surfacants", Physical Chemistry Tenside Sur. Det., 35(3):207-212 (1998).

Brenes, et al., "Stability of Copigmented Anthocyanins and Asorbics Acid in a Grape Juice Model System", J. Agric Food Chem, 53(1):49-56 (2005)—Abstrace, 1 page.

Bronopol. Revtrieved online on Jun. 4, 2011. <URL:http://chemicalland21.com/specialtychem/perchem/BRONOPOL.html>. Jul. 17, 2006. 4 pages.

Buck, et al., "Treatment of Vaginal Intraephithelial Neoplasia (Primarily Low Grade) with Imiquimod 5% Cream", Journal of Lower Genetial Tract Disease, 7(3):290-293 (2003).

Bucks, Daniel A.W., et al., "Bioavailability of Topically Administered Steroids: A 'Mass Balance' Technique," Journal of Investigative Dermatology, vol. 91, No. 1, Jul. 1988, pp. 29-33.

Bunker,et al., "Alterations in Scalp Blood Flow after the Epicutaneous Application of 3% Minoxidil and 0.1% Hexyl Nicotinate in Alopecia", Presented as a poster at the meeting of the British Society for Investigavie Dermatology, York, Sep. 1986 (2 pages).

Burton, et al., "Hypertrichosis Due to Minoxidil", British Journal of Dermatology, 101:593-595 (1979).

Campos, et al., "Ascorbic Acid and Its Derivatives in Cosmetic Formulations", Cosmetics and Toiletries, 115(6):59-62 (2000)—Abstract, 1 page.

Carbowax 1000MSDS; http://www.sciencelab.com/xMSDS-Polyethylene.sub.--glycol.sub.--1000-9926- 622. Accessed Dec. 13, 2008, 6 pages.

Carelli, et al., "Effect of Vehicles on Yohimbine Permeation Across Excised Hairless Mouse Skin", Pharm Acta Helv, 73(3):127-134 (1998)—Abstract, 1 page.

Chebil, et al., "Soulbility of Flavonoids in Organic Solvents", J. Chem. Eng. Data, 52(5):1552-1556 (2007)—Abstract, 1 page.

Cheshire, et al., Disorders of Sweating, www.medscape.com, Semin Neurol 23(4):399-406, 2003.

Chevrant-Breton, et al., "Etude du Traitement Capillaire <<Bioscalin>> dans les Alopecies Diffuses de la Femme", Gazette Medicale, 93(17):75-79 (1986) [English abstract].

Chiang, et al., "Bioavailability Assessment of Topical Delivery Systems: In Vitro Delivery of Minoxidil from Prototypical Semi-Solid Formulations", Int. J. Pharm, 49(2):109-114 (1989)—Abstract, 1 page.

Chinnian, et al., "Photostability Profiles of Minoxidil Solutions", PDA J. Pharm Sci Technol., 50(2):94-98 (1996)—Abstract, 1 page.

Chollet, et al., "Development of a Topically Active Imiquimod Formulation", Pharmaceutical Development and Technology, 4(1):35-43 (1999).

Chollet, et al., "The Effect of Temperatures on the Solubility of Immiquimod in Isostearic Acid", Abstract 3031, Pharmaceutical Research, vol. 14, No. 11 Supplemental (November), p. S475 (1997), 2 pages.

Coetzee, "Acceptability and Feasibility of Micralax applicators and of methyl cellulose gel placebo for large-scale clinical trials of vaginal microbicides," Nicol.AIDS 2001, vol. 15, No. 14, pp. 1837-1842.

Colloidal Silica. Retrieved online on Jun. 4, 2011. <URL:http://www.grace.com/engineeredmaterials/materialsciences/colloidalsilica/default.aspx>. Copyright 2011. 4 pages.

Croda 2. Croda Cetomacrogol 1000 Product Information Sheet. 2011 (no month given). 1 page.

Croda. Aracel 165 Product Summary. 2011 (no month given). 1 page.

D.W.A. Sharp Dictionary of Chemistry, Penguin Books, 1983, 3 pages.

Dalby, "Determination of Drug Solubility in Aerosol Propellants," Pharmaceutical Research, vol. 8, No. 9, 1991, pp. 1206-1209.

Dawber, et al., "Hypertrichosis in Females Applying Minoxidil Topical Solution and in Normal Controls", JEADV, 17:271-275 (2003).

Denatonium Benzoate http://www.newdruginfo.com/pharmaceopeia/usp28/v28230/usp28nf23s0.sub.--m- 22790.htm Accessed Dec. 9, 2008, 2 pages.

Dentinger, et al., "Stability of Nifedipine in an Extemporaneously Compounded Oral Solution", American Journal of Health-System Pharmacy, 60(10):1019-1022 (2003)—Abstract, 1 page.

Disorder. (2007). In the American Heritage Dictionary of the English Language. Retrieved from http://www.credoreference.com/entry/hmdictenglang/disorder. 1 page.

Draelos, Z. D. "Antiperspirants and the Hyperhidrosis Patients." Dermatologic Therapy. 2001. vol. 14. pp. 220-224.

Edens, et al., "Storage Stability and Safey of Active Vitamin C in a New Dual-Chamber Dispenser", Journal of Applied Cosmetology, 17(4):136-143 (1999)—Abstract, 1 page.

Edirisinghe, et al., "Effect of fatty acids on endothelium-dependent relaxation in the rabbit aorta", Clin Sci (Lond). Aug. 2006; 111(2): 145-51.

Edwards, "Imiquimod in Clinical Practice", J. Am Acad Dermatol., 43(1, Pt 2):S12-S17 (2000)—Abstract, 1 page.

Emulsifiers with HLB values. http://www.theherbarie.com/files/resources-center/formulating/Emulsifiers- .sub.--HLB.sub.--Values.pdf accessed Aug. 5, 2009 (3 pps).

Encyclopedia of Pharmaceutical Technology, Second Edition, vol. 3, Copyright 2002, 4 pages.

Esposito, E. et al. "Nanosystems for Skin Hydration: A Comparative Study." International Journal of Cosmetic Science. 29. 2007. pp. 39-47.

Ethanol, Accessed http://www.sigmaaldrich.com/catalog/ProductDetail.do?N4=E7023SIAL&N5=SEAR- CH.sub.--CONCAT.sub.--PNOBRAND.sub.--KEY&F=SPEC Dec. 9, 2008, 2 pages.

Ethylene Oxide Derivatives: An Essence of Every Industry. A definition of Emulsifier. Http://www.emulsifiers.in/ethylene_oxide_derivatives2.htm. Accessed Jul. 12, 2011. 3 pages.

Farahmand, et al., "Formulation and Evaluation of a Vitamin C Multiple Emulsion", Pharmaceutical Development and Technology, 11(2):255-261 (2006)—Abstract, 1 page.

Final Office Action for U.S. Appl. No. 11/430,437, Tamarkin et al., Dec. 16, 2008, 24 pages.

Flick, Cosmetic and Toiletry Formulations, vol. 5, 2nd Edition, Copyright 1996, 63 pages. Relevant pp. 251-309.

Fontana, Anthony J., "Water Activity: Why It is Important for Food Safety," International Conference on Food Safety, Nov. 16-18, 1998, pp. 177-185.

Gallarate, et al., "On the Stability of Ascorbic Acid in Emulsified Systems for Topical and Cosmetic Use", International Journal of Pharmaceutics, 188:233-241 (1999).

Galligan, John et al., "Adhesive Polyurethane Liners for Anterior Restorations," J. Dent. Res., Jul.-Aug. 1968, pp. 629-632.

Gelbard et al. "Primary Pediatric Hyperhidrosis: A Review of Current Treatment Options." Pediatric Dermatology. 2008. 25 (6). pp. 591-598.

Gill, A.M, et al., "Adverse Drug Reactions in a Paediatric Intensive Care Unit," Acta Paediatr 84:438-441, 1995.

Gladkikh, "Ascorbic Acid and Methods of Increasing its Stability in Drugs", Translated from Khimiko-Farmatsevticheskii Zhurnal, 4(12):37-42 (1970)—1 page.

Glaser, et al., Hyperhidrosis: A Comprehensive and Practical Approach to Patient Management, Expert Rev. Dermatol. 1(6), 773-775 (2006).

Graves, S. et al. "Structure of Concentrated Nanoemulsions." The Journal of Chemical Physics.. 122 America Institute of Physics. Published Apr. 1, 2005. 6 pages.

Groveman, et al., "Lack of Efficacy of Polysorbate 60 in the Treatment of Male Pattern Baldness", Arch Intern Med, 145:1454-1458 (1985).

Gschnait, F., et al., "Topical Indomethacin Protects from UVB and UVA Irriadiation," Arch. Dermatol. Res. 276:131-132, 1984.

Hakan, et al., "The protective effect of fish oil enema in acetic acid and ethanol induced colitis," The Turkish Journal of Gasroenterology, 2000, vol. 11, No. 2, pp. 155-161.

(56) References Cited

OTHER PUBLICATIONS

Hall, Karla, "Diaper Area Hemangiomas: A Unique Set of Concerns," http://members.tripod.com/.about.Michelle.sub.--G/diaper.html, Dec. 1, 2008, 8 pages.

Hallstar. Retrieved online on Jun. 4, 2011. <URL:http://www.hallstar.com/pis.php?product=1H022>. 1 page.

Hargreaves, "Chemical Formulation, An Overview of Surfactant-Based Preparations Used in Everyday Life", *The Royal Society of Chemistry*, pp. 114-115 (2003).

Harrison, et al., "Effects of cytokines and R-837, a cytokine inducer, on UV-irradiation augmented recurrent genital herpes in guinea pigs", Antivial Res., 15(4):315-322 (1991).

Harrison, et al., "Modification of Immunological Responses and Clinical Disease During Topical R-837 Treatment of Genital HSV-2 Infection", Antiviral Research, 10:209-224 (1988).

Harrison, et al., "Pharmacokinetics and Safety of Iminquimod 5% Cream in the Treatment of Actinic Keratoses of the Face, Scalp, or Hands and Arms", Arch. Dermatol. Res., 296(1):6-11 (2004)—Abstract, 1 page.

Harrison, et al., "Posttherapy Suppression of Genital Herpes Simplex Virus (HSV) Recurrences and Enhancement of HSV-Specific T-Cell Memory by Imiquimod in Guinea Pigs", Antimicrobial Agents and Chemotherapy, 38(9):2059-2064 (1994).

Hashim, et al. "Tinea versicolor and visceral leishmaniasis," Int J Dermatol., Apr. 1994; 33(4), pp. 258-259 (abstract only).

Heart Failure, The Merck Manual, 2008 <<http://www.merck.com/mmhe/sec03/ch025/ch025a.html>> 12 pages.

Hepburn, NC., "Cutaneous leishmaniasis," Clin Exp Dermatol, Jul. 2000; 25(5), pp. 363-370 (abstract only).

Hill, Randall M. (Ed.) Silicone Surfactants, Table of Contents and Chapter 7, "Silicone Surfactants: Applicants in the Personal Care Industry," by David T. Floyd, 1999 (30 Pages).

Hormones. Http://www.greenwillowtree.com/Page.bok?file=libido.html. Jan. 2001.

http://ibabydoc.com/online/diseaseeczema.asp., Atopic Dermatitis, Copyright 2000, 6 pages.

http://web.archive.org/web/20000106225413/http://pharmacy.wilkes.edu/kibbeweb/lab7.html, Characteristics of Surfactants and Emulsions, Jan. 29, 2010, 5 pages.

http://www.agworkshop.com/p3.asp, AG&Co. Essential oil workshop. 1 page. Accessed Jan. 31, 2010.

Hubbe, Martin. Mini-Encyclopedia of Papermaking Wet-End Chemistry: Additives and Ingredients, their Composition, Functions, Strategies for Use. Retrieved online on Jun. 4, 2011. <URL://http://www4.ncsu.edu/~hubbe/CSIL.htm>. Feb. 1, 2001. 2 pages.

hydroxyethylcellulose. Http: //terpconnect.umd.edu/-choi/MSDS/Sigma-Aldrich/HYDROXYETHYL%20CELLULOSE, 5 pages, Jan. 14, 2004.

ICI Americas Inc. "The HLB System: A Time-Saving Guide to Emulsifier Selection." Mar. 1980. pp. 1-22.

Ikuta, et al., "Scanning Electron Microscopic Observation of Oil/Wax/Water/Surfacant System", Journal of SCCJ, 34(4):280-291 (2004)—Abstract, 1 page.

Indomethacin. Retrieved online on Jun. 3, 2011. <URL:http://it03.net/com/oxymatrine/down/1249534834.pdf>. Aug. 15, 2009. 3 pages.

Innocenzi, Daniele et al., "An Open-Label Tolerability and Effacy Study of an Aluminum Sesquichlorhydrate Topical Foam in Axillary and Palmar Primary Hyperhidrosis," Dermatologic Therapy, vol. 21, S27-S30, 2008.

Izquierdo, P. et al. "Formation and Stability of Nano-Emulsions Prepared Using the Phase Inversion Temperature Method." University of Barcelona. Sep. 17, 2001. 1 page.

Jan. "Troubled Times: Detergent Foam." http://zetatalk.com/health/theall7c.htm. Accessed Feb. 9, 2012. 2 pages.

Joseph, "Understanding foams & foaming," University of Minnesota (1997), at http://www.aem.umn.edu/people/faculty/joseph/archive/docs/understandingfoams.pdf, pp. 1-8.

Kalkan, et al., The Measurement of Sweat Intensity Using a New Technique, Tr. J. of Medical Sciences 28, 515-517 (1998).

Kanamoto, et al., "Pharmacokinetics of two rectal dosage forms of ketoprofen in patients after anal surgery," J Pharmacobiodyn., Mar. 1988; 11(3):141-5.

Kang,et al., "Enhancement of the Stability and Skin Penetration of Vitamin C by Polyphenol", Immune Netw., 4(4):250-254 (2004)—Abstract, 1 page.

Karasu, T.B. et al., "Treatment of Patients with Major Depressive Disorder, Second Edition," pp. 1-78, 2000.

Kathon.TM. CG (product information sheet by Rohm and Haas, Jun. 2006).

Kim, "Stability of Minoxidil in Aqueous Solution", Yakhak Hoechi, 30(5):228-231 (1986)—Abstract, 1 page.

Kinnunen, "Skin reactions to hexylene glycol," Contact Dermatitis Sep. 1989; 21(3): 154-8.

Kleber, M.D., H.D. et al., "Treatment of Patients with Substance Use Disorders, Second Edition," pp. 1-276, 2006.

Koerber, S., "Humectants and Water Activity," Water Activity News, 2000, ISSN No. 1083-3943.

Kreuter, J. "Nanoparticles and microparticles for drug and vaccine delivery," J. Anat. (1996) 189, pp. 503-505.

Kumar, J. et ak., "Application of Broad Spectrum Antiseptic Povidone Iodine as Powerful Action: A Review," Journal of Pharmaceutical Science and Technology vol. 1(2), 2009, 48-58.

Kwak et al. "Study of Complete Transparent Nano-Emulsions which Contain Oils." IFSCC Conference 2003, Seoul, Korea, Sep. 22-24, 2003. 3 pages.

Lautenschlager, Dr. Hans. "A Closer Look on Natural Agents: Facts and Future Aspects." Kosmetic Konzept. Kosmetische Praxis. 2006 (no month given). (5), 8-10. 3 pages.

Lebwohl et al. "Treatment of Psoriasis. Part 1. Topical Therapy and Phototherapy." *J Am. Acad. Dermatol.* 45:487-498. Oct. 2001.

Lebwohl et al., "A randomized, double-blind, placebo-controlled study of clobestasol propionate 0.05% foam in the treatment of nonscalp psoriasis," *International Journal of Dermatology*, 2002, 41(5): 269-274.

Lee, et al., "The Stabilization of L-Ascorbic Acid in Aqueous Solution and Water-in-Oil-in-Water Double Emulsion by Controlling pH and Electrolyte Concentration", J. Cosmet. Sci., 55:1-12 (Jan./Feb. 2004).

Leung, et al., "Bioadhesive Drug Delivery in Water-Soluble Polymers," American Chemical Society, Chapter 23, 1991, pp. 350-366.

Li, et al., "Solubility Behavior of Imiquimod in Alkanoic Acids", Abstract 3029, Pharmaceutical Research, vol. 14, No. 11 Supplemental (November), p. S475 (1997), 2 pages.

Licking Vaginal Dryness without a Prescription. Accessed http://www.estronaut.com/a/vag.sub.--dryness.htm on Dec. 14, 2008, 3 pages.

Lippacher, A. et al. "Liquid and Semisolid SLN Dispersions for Topical Application Rheological Characterization." European Journal of Pharmaceutics and Biopharmaceutics. 58. 2004. pp. 561-567.

Lupo, "Antioxidants and Vitamins in Cosmetics", Clinics in Dermatology, 19:467-473 (2001).

Martindale, The extra pharmacopoeia [28th] edition, Eds.: Reynolds, J.E.F. and Prasad, A.B., The Pharmaceutical Press, London, pp. 862-864, 1982.

Martindale. 33 ed. London, Bath Press, 2002. pp. 1073 and 1473.

Material Safety Data Sheet, Progesterone, Apr. 26, 2006, 5 pages.

Material Safety Data Sheet, Science Lab.com, Polyethylene Glycol 1000, MSDS, Nov. 6, 2008, 6 pages.

Merck index, 10th edition, Merck & Co., Inc.: Rahway, NJ, 1983, pp. 39 (entry 242 for allantoin).

Merck index, 14th edition, O'Neill, ed., 2006, entry for p-amino benzoic acid.

Merck index, 14th edition, O'Neill, ed., 2006, entry for zinc oxide.

Merck Index, An Encyclopedia of Chemicals, Drugs, and Biologicals. 13$^{th}$ Edition. O'Neil et al eds. Entries 1058, 2350, 6143, and 8803. 2001. 7 pages.

Merck Manual Home Edition. "Excessive Sweating: Sweating Disorders." Accessed Apr. 14, 2011 at www.merckmanuals.com/home/print/sec18/ch206/ch206c.html. 2 pages.

Merriam Webster Online Dictionary [online] retrieved from http://www.merriam-webster.com/cgi-bin/dictionary?book=dictionary&va=derivative on Jul. 5, 2008; 1 page.

(56) References Cited

OTHER PUBLICATIONS

Merriam-Webster Online Dictionaary, 2008, "Mousse," Merriam-Webster Online, Dec. 8, 2008 http://www.merriam-webster.com/dictionary/mousse, 2 pages.
Messenger, et al., "Minoxidil: Mechanisms of Action on Hair Growth", British Journal of Dermatology, 150:186-194 (2004).
Metronidazole. www.usp.org/pdf/EN/veterinary/metronidazole.pdf. accessed Sep. 10, 2009, 4 pages.
Metz, et al., "A Phase I Study of Topical Tempol for the Prevention of Alopecia Induced by Whole Brain Radiotherapy", Clinical Cancer Research, 10:6411-6417 (2004).
Meucci, et al., "Ascorbic Acid Stability in Aqueous Solutions", Acta Vitaminol Enzymol, 7(3-4):147-153 (1985)—Abstract, 1 page.
MMP Inc. International Development and Manufacturing, "Formulating specialities," http://mmpinc.com, 3 pages. Feb. 2, 2010.
Molan, Peter Clark, "World Wide Wounds," Dec. 2001, 13 pages.
Morgan, Timothy M., et al., "Enhanced Skin Permeation of Sex Hormones with Novel Topical Spray Vehicles," Journal of Pharmaceutical Sciences, vol. 87, No. 10, Oct. 1998, pp. 1213-1218.
Neutrogena. Http://www.cosmetoscope.com/2010/04/neutrogea-clinical-with-johnson-johnsons-cytomimic-techology/. Published Apr. 28, 2010. Accessed Sep. 11, 2010, 5 pages.
Nietz, "Molecular orientation at surfaces of solids," *J. Phys. Chem.*, 1928, 32(2): 255-269.
No Author Listed. "Opitmization of Nano-Emulsions Production by Microfluidization." European Food Research and Technology. vol. 225, No. 5-6. Sep. 2007. Abstract. 1 page.
Office Action for U.S. Appl. No. 11/430,437, Tamarkin et al., May 9, 2008, 27 pages.
Office Action received from the U.S. Patent Office, U.S. Appl. No. 11/430,599, Jul. 28, 2008 (59 pages).
Oil. Dictionary of Chemistry. Editor: DWA Sharp. Copyright 1990.
Olsen, et al., "A Multicenter, Randomized, Placebo-Controlled, Double-Blind Clinical Trial of a Novel Formulation of 5% Minoxidil Topical Foam Versus Placebo in the Treatment of Androgenetic Alopecia in Men", J. Am. Acad Dermatol, 57:767-774 (2007).
OM Cinnamate. http://www.makingcosmetics.com/sunscreens/OM-Cinnamate-p102.html accessed Sep. 26, 2009, 1 page.
Padhi et al., "Phospho-olicines as positive-electrode materials for rechargeable lithium batteries," *J. Electrochemical Soc.*, 1997, 144(4): 1188-1194.
Pakpayat, et al., "Formulation of Ascorbic Acid Microemulstions with Alkyl Polyglycosides", European Journal of Pharmaceutics and Biopharmaceutics, 72:444-452 (2009).
Paula. http://ww.cosmeticscop.com/cosmetic-ingredient-dictionary/definition/259/c12-15-alkyl-benzoate.aspx. Printed Oct. 24, 2010. 1 page.
Pendergrass, "The shape and dimension of the human vagina as seen in three-dimensional vinyl polysiloxane casts," Gynecol Obstet. Invest. 1996:42(3):178-82.
Prescription Information for Aldara, Mar. 2007 (29 pages).
Prevent. (2007). In the American Heritage Dictionary of the English Language. Retrieved from http://www.credoreference.com/entry/hmdictenglang/prevent. 1 page.
Psoriasis, http://www.quickcare.org/skin/causes-of0psoriasis.html. Accessed Sep. 9, 2010—3 pages.
Purcell, Hal C. "Natural *Jojoba* Oil Versus Dryness and Free Radicals." Cosmetics and Toiletries Manufacture Worldwide. 1988. 4 pages.
Raschke, et al., "Topical Activity of Ascorbic Acid: From In Vitro Optimization to In Vivo Efficacy", Skin Pharmacology and Physiology, 17(4):200-206 (2004)—Abstract, 1 page.
Ravet et al., "Electroactivity of natural 503-507 and synthetic triphylite," *J. of Power Sources*, 2001, 97-98:503-507.
Raymond, Iodine as an Aerial Disinfectant, Journal of Hygiene, vol. 44, No. 5 (May 1946), pp. 359-361.
Receptacle. Merriam Webster. Http://www.merriam-webster.com/dictionary/receptacle. Accessed Jul. 12, 2011. 1 page.
Richwald, "Imiquimod", Drugs Today, 35(7):497 (1999)—Abstract, 1 page.

Rieger and Rhein. "Emulsifier Selection/HLB." Surfactants in Cosmetics. 1997 (no month given). 1 page.
Rosacea, http://clinuvel.com/skin-conditions/common-skin-conditions/rosacea#h0-6-prevention. Accessed Sep. 9, 2010, 5 pages.
Savin, et al., "Tinea versicolor treated with terbinafine 1% solution," Int J. Dermatol, Nov. 1999; 38(11), pp. 863-865.
Schmidt A., "*Malassezia furfur*: a fungus belonging to the physiological skin flora and its relevance in skin disorders," Curtis., Jan. 1997; 59(1), pp. 21-24 (abstract).
Schulze, M.D., Harry "Iodine and Sodium Hypochlorite as Wound Disinfectants," The British Medical Journal, pp. 921-922, 1915.
Scientific Discussion for the approval of Aldara, EMEA 2005 (10 pages).
Scott as Published in Pharmaceutical Dosage Forms; Disperse Systems, vol. 3, Copyright 1998, 120 pages.
Seborrheic Dermatitis, http://www.cumc.columbia.edu/student/health/pdf/R-S/Seborrhea%20Dermatitis.pdf. Access Sep. 9, 2010, 2 pages.
Shear, et al., "Pharmacoeconomic analysis of topical treatments for tinea infections," Pharmacoeconomics. Mar. 1995; 7(3); pp. 251-267 (abstract only).
Sheu, et al., "Effect of Tocopheryl Polyethylene Glycol Succinate on the Percutaneous Penetration of Minoxidil from Water/Ethanol/Polyethylene Glycol 400 Solutions", Drug Dev. Ind. Pharm., 32(5):595-607 (2006)—Abstract, 1 page.
Shim, et al., "Transdermal Delivery of Mixnoxidil with Block Copolymer Nanoparticles", J. Control Release, 97(3):477-484 (2004)—Abstract, 1 page.
Shrestha et al., Forming properties of monoglycerol fatty acid esters in nonpolar oil systems, *Langmuir*, 2006, 22: 8337-8345.
Sigma Aldrich, "HLB-Numbers In Lithography Nanopatterning," http://www.sigmaaldrich.com/materials-science/micro-and-nanoelectronics/1- ithography-nanopatterning/hlb-numbers.html, accessed: Feb. 2, 2009, pp. 1-3.
Sigma-Aldrich, Material Safety Data Sheet, Hydroxyethyl Cellulose, Mar. 3, 2004, 5 pages.
Silicone. Definition. Retrieved Apr. 19, 2011 from http://www.oxforddictionaries.com/definition/silicone?view=uk. 1 page.
Simovic, S. et al., "The influence of Processing Variables on Performance of O/W Emulsion Gels Based on Polymeric Emulsifier (Pemulen OTR-2NF)," International Journal of Cosmetic Science, vol. 2(2): abstract only. Dec. 24, 2001, 1 page.
Skin Biology, CP Serum—Copper-Peptide Serum for Skin Regeneration and Reducing Wrinkles, Skin Biology, http://web.archive.org/web/20030810230608/http://www.skinbio.com/cpserum.-html, Dec. 1, 2008, 21 pages.
Skin Deep Cosmetics. PPG-40-PEG-60 Lanolin Oil http://www.cosmeticsdatabase.com/ingredient/722972/PPG-40-PEG-60_Lanolin_Oil/?ingred06=722972. 2010, 3 pages.
Smith, Anne. "Sore Nipples." Breastfeeding Mom's Sore Nipples: Breastfeeding Basics. http://breastfeedingbasics.com/articles/sore-nipples. Accessed Feb. 8, 2012. 9 pages.
Sonneville-Aubrun, O. et al. "Nanoemulsions: A New Vehicle for Skincare Products." Advances in Colloid and Interface Science. 108-109.. 2004. pp. 145-149.
Squire. J, "A randomised, single-blind, single-centre clinical trial to evaluate comparative clinical efficacy of shampoos containing ciclopirox olamine (1.5%) and salicylic acid (3%), or ketoconazole (2%, Nizoral) for the treatment of dandruff/seborrhoeic dermatitis," Dermatolog Treat. Jun. 2002;13(2):51-60 (abstract only).
Sreenivasa, et al., "Preparation and Evaluation of Minoxidil Gels for Topical Application in Alopecia", Indian Journal of Pharmaceutical Sciences, 68(4):432-436 (2006), 11 pages.
Stehle et al., Uptake of minoxidil from a new foam formulation devoid of propylene glycol to hamster ear hair follicles, *J. Invest. Dermatol.*, 2005, 124(4), A101.
Sugisaka, et al., "The Physiochemical Properties of Imiquimod, The First Imidazoquinoline Immune Response Modifier", Abstract 3030, Pharmaceutical Research, vol. 14, No. 11 Supplemental (November), p. S475 (1997), 2 pages.
Surfactant. Chemistry Glossary. Http://chemistry.about.com/od/chemistryglossary/g/surfactant.htm, 2012, 1 page.

(56) References Cited

OTHER PUBLICATIONS

Sweetman, Sean C. Martindale: The Complete Drug Reference. 33rd Edition. London. Pharmaceutical Press. Jun. 21, 2002. pp. 1073 and 1473. 5 pages.
Tadros, Tharwat F. "Surfactants in Nano-Emulsions." Applied Surfactants: Principles and Applications. Wiley-VCH Verlag GmbH & Co. Weinheim. ISBN: 3-527-30629-3. 2005. pp. 285-308.
Tan et al., "Effect of Carbopol and Polyvinlpyrrolidone on the Mechanical Rheological and Release Properties of Bioadhesive Polyethylene Glycol Gels," AAPS PharmSciTech, 2000; 1(3) Article 24, 2000, 10 pages.
Tanhehco, "Potassium Channel Modulators as Anti-Inflammatory Agents", Expert Opinion on Therapeutic Patents, 11(7):1137-1145 (2001)—Abstract, 3 pages.
Tarumoto, et al., Studies on toxicity of hydrocortisone 17-butyrate 21-propionate -1. Acute toxicity of hydrocortisone 17-butyrate 21-propionate and its analogues in mice, rats and dogs (author's trans), J Toxicol Sci., Jul. 1981; 6 Suppl: 1-16 (Abstract only).
Tata, et al., "Penetration of Minoxidil from Ethanol Propylene Glycol Solutions: Effect of Application Volume on Occlusion", Journal of Pharmaceutical Sciences, 84(6):688-691 (1995).
Tata, et al., "Relative Influence of Ethanol and Propylene Glycol Cosolvents on Deposition of Minoxidil into the Skin", Journal of Pharmaceutical Sciences, 83(10):1508-1510 (1994).
Third Party Submission for U.S. Appl. No. 12/014,088, Feb. 4, 2009, 4 pages.
Torres-Rodriguez, JM., "New topical antifungal drugs," Arch Med Res. 1993 Winter; 24(4), pp. 371-375 (abstract).
Toxicology and Carcinogenesis Studies of t-Butyl Alcohol (Cas No. 75-65-0) in F344/N Rats and B6C3F1 Mice (Drinking Water Studies), http://ntp.niehs.nih.gob/?objectid-=0709F73D-A849-80CA-5FB784E866B576D1. Accessed Dec. 9, 2008, 4 pages.
Trofatter, "imiquimod in clinical Practice", European Journal of Dermatology, 8(7 Supp.):17-19 (1998)—Abstract, 1 page.
Tsai, et al., "Drug and Vehicle Deposition from Topical Applications: Use of In Vitro Mass Balance Technique with Minosidil Solutions", J. Pharm. Sci., 81(8):736-743 (1992)—Abstract, 1 page.
Tsai, et al., "Effect of Minoxidil Concentration on the Deposition of Drug and Vehicle into the Skin", International Journal of Pharmaceutics, 96(1-3):111-117 (1993)—Abstract, 1 page.
Tsai, et al., "Influence of Application Time and Formulation Reapplication on the Delivery of Minoxidil through Hairless Mouse Skin as Measured in Franz Diffusion Cells", Skin Pharmacol., 7:270-277 (1994).
Tyring, "Immune-Response Modifiers: A New Paradigm in the Treatment of Human Papillomavirus", Current Therapeutic Research, 61(9):584-596 (2000)—Abstract, 1 page.
Tzen, Jason T.C. et al. "Surface Structure and Properties of Plant Seed Oil Bodies." Department of Botany and Plant Sciences, University of California, Riverside, California 92521. Apr. 15, 1992. 9 pages.
Uner, M. et al. "Skin Moisturizing Effect and Skin Penetration of Ascorbyl Palmitate Entrapped in Solid Lipid Nanoparticles (SLN) and Nanostructured Lipid Carriers (NLC) Incorporated into Hydrogel." Pharmazie. 60. 2005. 5 pages.
Veron, et al., "Stability of Minoxidil Topical Formulations", Ciencia Pharmaceutica, 2(6):411-414 (1992), Abstract, 1 page.
Wermuth, C.G. "Similarity in drugs: reflections on analogue design," Drug Discovery Today, vol. 11, Nos. 7/8, Apr. 2006, pp. 348-354.
Williams, "Scale up of an olive/water cream containing 40% diethylene glycol momoethyl ether", Dev. Ind. Pharm., 26(1):71-77 (2000).
Wormser et al., Protective effect of povidone-iodine ointment against skin lesions induced by sulphur and nitrogen mustards and by non-mustard vesicants, Arch. Toxicol., 1997, 71, 165-170.
Wormser, Early topical treatment with providone-iodine ointment reduces, and sometimes prevents, skin damage following heat stimulus, Letter to the Editor, Burns 24, pp. 383, 1998.

Yamada and Chung, "Crystal Chemistry of the Olivine-Type Li$(Mn_yFe_{1-y})PO_4$ and $(Mn_yFe_{1-y})PO_4$ as Possible 4 V Cathode Materials for Lithium Batteries," J. Electrochemical Soc., 2001, 148(8): A960-967.
"Coal tars and coal-tar pitches," Report on Carcinogens, Twelfth Edition, 2011, 3 pages.
Adisen et al. "Topical tetracycline in the 7:953-5 treatment of acne vulgaris," J Drugs Dermatol., 2008,.
Baskaran et al., "Poloxamer-188 improves capillary blood flow and tissue viability in a cutaneous burn wound," J. Surg. Res., 2001, 101(1):56-61.
Bell-Syer et al. "A systematic review of oral treatments for fungal infections of the skin of the feet," J. Dermatolog. Treat., 2001, 12:69-74.
Boehm et al. 1994, "Synthesis of high specific activity [.sup.3 H]-9-cis-retinoic acid and its application for identifying retinoids with unusual binding properties," J. Med. Chem., 37:408-414.
Carapeti et al., "Topical diltiazem and bethanechol decrease anal sphincter pressure and heal anal fissures without side effects," Dis Colon Rectum, 2000, 43(10):1359-62.
Cook and Mortensen, "Nifedipine for treatment of anal fissures," Dis Colon Rectum, 2000, 43(3):430-1.
Dumortier et al., "A review of poloxamer 407 pharmaceutical and pharmacological characteristics," Pharmaceutical Res., 2006, 23(12):2709-2728.
Ebadi et al., "Healing effect of topical nifedipine on skin wounds of diabetic rats," DARU, 2003, 11(1):19-22.
Effendy and Maibach. "Surfactants and Experimental Irritant Contact Dermatitis." Contact Dermatol., 1995, 33:217-225
Elias and Ghadially, "The aged epidermal permeability barrier," Clinical Geriatric Medicine, Feb. 2002, pp. 103-120.
Fantin et al., "Critical influence of resistance to streptogramin B-type antibiotics on activity of RP 59500 (Quinupristin-dalfopristin) in experimental endocarditis due to Staphylococcus aureus," Antimicrob Agents and Chemothery, 1999, 39:400-405.
Fluhr et al., "Glycerol accelerates recovery of barrier function in vivo," Acta Derm. Venereol,. 1999, 79:418-21.
Garti et al. "Sucrose Esters microemulsions," J. Molec. Liquids, 1999, 80:253-296.
Hammer et al. "Anti-Microbial Activity of Essential Oils and other Plant extracts," J. Applied. Microbiology, 1999, 86:985-990.
Hwang et al. "Isolation and identification of mosquito repellents in Artemisia vulgaris," J. Chem. Ecol.. 11: 1297-1306, 1985.
Knight et al., "Topical diltiazem ointment in the treatment of chronic anal fissure," Br. J. Surg., 2001, 88(4):553-6.
Kucharekova et al., "Effect of a lipid-rich emollient containing ceramide 3 in experimentally induced skin barrier dysfunction," Contact Dermatitis, Jun. 2002, pp. 331-338.
Leive et al, "Tetracyclines of various hydrophobicities as a probe for permeability of Escherichia coli outer membrane," Antimicrobial Agents and Chemotherapy, 1984, 25:539-544.
Luepke and Kemper, "The HET-CAM Test: An Alternative to the Draize Eye Test," FD Chem. Toxic., 1986, 24:495-196.
Osborne and Henke, "Skin Penetration Enhancers Cited in the Technical Literature," Pharm. Technology, Nov. 1997, pp. 58-86.
Padi. "Minocycline prevents the development of neuropathic pain, but not acute pain: possible anti-inflammatory and antioxidant mechanisms," Eur J. Pharmacol, 2008, 601:79-87.
Palamaras and Kyriakis, "Calcium antagonists in dermatology: a review of the evidence and research-based studies," Derm. Online Journal, 2005, 11(2):8.
Passi et al., Lipophilic antioxidants in human sebum and aging, Free Radical Research, 2002, pp. 471-477.
Perrotti et al., "Topical Nifedipine With Lidocaine Ointment vs. Active Control for Treatment of Chronic Anal Fissure," Dis Colon Rectum, 2002, 45(11):1468-1475.
Repa et al. "All-trans-retinol is a ligand for the retinoic acid receptors,", Proc. Natl. Acad Sci, USA, 90: 7293-7297, 1993.
Ruledge, "Some corrections to the record on insect repellents and attractants," J. Am. Mosquito. Control Assoc, 1988, 4(4): 414-425.
Sakai et al., "Characterization of the physical properties of the stratum corneum by a new tactile sensor," Skin Research and Technology, Aug. 2000, pp. 128-134.

(56) References Cited

OTHER PUBLICATIONS

Schaefer, "Silicone Surfactants," *Tenside, Surfactants, Deterg.*, 1990, 27(3): 154-158.

Simoni et al., "Retinoic acid and analogs as potent inducers of differentiation and apoptosis. New promising chemopreventive and chemotherapeutic agents in oncology," *Pure Appl Chem.*, 2001, 73(9):1437-1444.

Smith, "Hydroxy acids and skin again," *Soap Cosmetics Chemical Specialties*, 1993, pp. 54-59.

Solans et al. "Overview of basic aspects of microemulsions," Industrial Applications of Microemulsions, Solans et al Eds, New York, 1997, 66:1-17.

Squillante et al., "Codiffusion of propylene glycol and dimethyl isosorbide in hairless mouse skin," *European J. Pharm. Biopharm.*, 1998, 46(3):265-71.

Todd et al. "Volatile Silicone Fluids for Cosmetics," *91 Cosmetics and Toiletries*, 1976, 27-32.

Torma et al., "Biologic activities of retinoic acid and 3, 4-dehydroretinoic acid in human keratinoacytes are similar and correlate with receptor affinities and transactivation properties," *J. Invest. Dermatology*, 1994, 102: 49-54.

USP23/NF 18 The United States Pharmacopeia: The National Formulary, US Pharmacopoeia, 1995, p. 10-14.

Van Slyke, "On the measurement of buffer values and on the relationship of buffer value to the dissociation constant of the buffer and the concentration and reaction of the buffer solution," *J. Biol. Chem.*, 1922, 52:525-570.

Van Cutsem et al., "The antiinflammatory efects of ketoconazole," *J. AM. ACAD. Dermatol.*, 1991, 25(2 pt 1):257-261.

Wang and Chen, "Preparation and surface active properties of biodegradable dextrin derivative surfactants," *Colloids and Surfaces A: Physicochemical and Engineering Aspects*, 2006, 281(1-3): 190-193.

Weindl et al., "Hyaluronic acid in the treatment and prevention of skin diseases: molecular biological, pharmaceutical and clinical aspects," *Skin Pharmacology and Physiology*, 2004, 17: 207-213.

Xynos et al., "Effect of nifedipine on rectoanal motility," *Dis Colon Rectum*, 1996, 39(2):212-216.

Yamada et al., "Candesartan, an angiotensin II receptor antagonist, suppresses pancreatic inflammation and fibrosis in rats," *J. Pharmacol. Exp. Ther.*, 2003, 307(1)17-23.

Paragraph E.3.1 of regulation (EC) No. 2003 (See Directive 67/548/EEC OJ 196, 16.8, 1967, p. 1.

Tzen et al., Lipids, proteins and structure of seed oil bodies from diverse species; *Plant Physiol.*, 1993, 101:267-276.

Brown et al. "Structural dependence of flavonoid interactions with Cu2+ inos: implications for their antioxidant properties," *Biochem. J.*, 1998, 330:1173-1178.

Cloez-Tayarani. et al., "Differential effect of serotonin on cytokine production in lipopolysaccharide-stimulated human peripheral blood mononuclear cells: involvement of 5-hydroxytryptamine2A receptors," *Int. Immunol.*, 2003, 15:233-40.

"Mineral oil USP," Chemical Abstracts Service Registry No. 8012-95-1, 2011, 7 pages.

"Tea tree oil," Chemical Abstract No. 68647-73-4, 2012, 2 pages.

Lin et al., "Ferulic acid stabilizes a solution of vitamins c and e and doubles its photoprotection of skin," *J Invest Dermatol*, 2005, 125:826-32.

* cited by examiner

FOAMABLE CARRIERS

CROSS REFERENCE TO RELATED APPLICATIONS

This application is a continuation of and claims benefit of priority under 35 U.S.C. §120 to U.S. application Ser. No. 11/116,761, filed Apr. 28, 2005, which 1) is a continuation-in-part application of co-pending International Patent Application No. IB03/005527, filed Oct. 24, 2003, which claims the benefit of priority under 35 U.S.C. §119(e) to U.S. Provisional Application Ser. No. 60/429,546, filed Nov. 29, 2002, and claims the benefit of priority under 35 USC§119(a) to Israeli Patent Application No. 152486, filed Oct. 25, 2002; 2) is a continuation-in-part application of co-pending U.S. patent application Ser. No. 10/911,367, filed Aug. 4, 2004, which claims the benefit of priority under 35 U.S.C. §119(e) to U.S. patent application Ser. No. 60/429,385, filed Aug. 4, 2003; and 3) claims the benefit of priority under 35 U.S.C. §119(e) to U.S. Patent Application Ser. No. 60/566,513, filed Apr. 28, 2004; all of which are incorporated by reference in their entirety herein.

FIELD OF THE INVENTION

The invention relates to an alcohol-free, foam carrier for delivery of an active agent to a mucosal body cavity. More specifically, the invention relates to foam carriers suitable for inclusion of poorly soluble, water soluble and oil soluble therapeutic agents for delivery and sustained release to the vaginal cavity.

BACKGROUND OF THE INVENTION

The vaginal cavity, including the vagina and cervix, provides a unique site for delivery of therapeutic agents, both for systemic and local action.

There are multiple anatomical structures which comprise the internal and external female genital tract including the clitoris, labia minora and corpus spongiosum (vestibular) erectile tissue, vagina, peri-urethral glans, urethra, Halban's fascia, anterior fornix erogenous zone, pubococcygeus muscle and cervix.

The vagina consists of a tube of autonomically-innervated smooth muscle (longitudinal outer, inner circular layer) lined by stratified squamous epithelium and a sub-dermal layer rich in capillaries. The vaginal wall consists of an inner glandular mucous type stratified squamous cell epithelium supported by a thick lamina propia. This epithelium undergoes hormone-related cyclical changes including slight keratinization of the superficial cells during the menstrual cycle. Deep in the epithelium lies the smooth muscles of the muscularis. There is a deeper surrounding fibrous layer above the muscularis which provides structural support to the vagina and is rich is collagen and elastin to allow for expansion of the. Three sets of skeletal muscles surround the vagina including the ischiocavernosum, bulbocavernosus, transverse perinei and levator ani and pubococcygeus muscles.

Women are vulnerable to diseases of the genital tract as the lining of the vagina is a permeable mucous membrane. Intercourse, lack of lubrication during intercourse, changes in the cervix during the menstrual cycle, and asymptomatic infections facilitate the transmission of infection to women. Prepubertal girls and adolescents are particularly vulnerable because their vaginal and cervical tissues may be less mature and are more readily penetrated by organisms (e.g., chlamydia and gonococcus). Postmenopausal women are more likely than younger women to get small abrasions in the vagina during sexual activity as a result of thinning of the tissue and dryness. Women who already have an infection (particularly one that causes genital lesions) are more likely to acquire or transmit another STD, including HIV. Other biological risks include the use of vaginal douches, which increase the risk of pelvic inflammatory disease (PID), and the influence of hormonal contraceptives on acquiring or transmitting an STD (e.g., increased risk of chlamydial infection with use of oral contraceptives).

In particular, the cervix is prone to several diseases, such as cervicitis (an inflammation of the uterine cervix, usually caused by infection), cancer, inflammation, erosion, intraepithelial neoplasia (CIN), polyps, dysplasia, human papillomavirus (HPV) infections causing some tumors, condylomas or warts and abnormal pregnancy.

Several factors must be taken into consideration when developing therapeutic delivery systems for the female genital system. These factors include the vaginal anatomy, the mucosal surface, the presence and composition of vaginal fluids and secretions, cervical fluids (mucus), cyclic changes and endogenous microflora. Drug stability to enzyme activity, which is quite high in vaginal environment, and is again a function of menstrual cycle and lifecycle, should also be taken into account. Topical drug delivery through the cervix, as needed to treat disorders of the cervix and uterus also presents a challenge.

Vaginal topical formulation should be compatible with daily activities, be easy to administer and provide accurate dosing. Several types of formulations are known for delivery to the vaginal cavity. While semi-solid formulations, such as creams, lotions, gels and ointments are commonly used, they are often reported to be messy, require frequent application and can be difficult to remove after use. Furthermore, application of topical gels and creams require several steps of operation. Solid formulations such as tablets, suppositories and pessaries also require frequent application, show a poor retention in vagina, and exhibit insufficient spreadability.

Rectal drug administration can be directed to both local and systemic drug delivery. It has been effectively used to treat local diseases of the anorectal area as well as an alternative to oral administration in the systemic administration of drugs. Solid suppositories are the most common dosage form used for rectal drug administration and represent the majority of rectal dosage forms; however, creams ointments and foams are also being used.

Current formulations for rectal administration still have significant disadvantages. They are difficult to insert through the anal orifice; they are difficult to spread throughout the target cavity; and if spreadable, they tend to leak, causing major discomfort to the patient. Such negative attributes lead to their very limited use.

Thus, new forms are desirable in order to achieve better control and ease of application, while maintaining the beneficial properties of such products. A product for intravaginal and anorectal application would ideally exhibit the following properties: (1) easy insertion, thus leading to high patient compliance; (2) accurate dosing, to ensure effective treatment; (3) expandability, for increased coverage of the target cavity surface and cervix; and (4) drip free formulation with good adhesive properties, for prolonged drug residence. The duration of the drug inside the vagina or rectum is also important for ensuring extended activity.

Use of emulsions in foam compositions is known. Emulsion systems provide a two-phase system including water in one phase and oily components in the second phase. Emulsifiers for reducing surface tension and for improving foam stability are included in the foam composition. Foams and, in particular, foam emulsions are complicated systems which do not form under all circumstances. Slight shifts in foam emulsion composition, such as by the addition of active ingredients, may destabilize the foam. In the case of oil-containing foams, high surfactant concentrations are required to attain foams of low density and acceptable texture.

Typical vaginal foam products are aqueous formulations and do not include significant levels of an oil-based solvent. For example. a nonoxynol-9-containing foam marketed under the trademane Delfen® foam (Advanced care, 12.5% nonoxynol-9), Emko® foam (Schering-Plough Healthcare, 12% nonoxynol-9) does not contain any oily solvent and has an ingredient list reciting "nonoxynol-9 12.5%, benzoic acid, cetyl alcohol, glacial acetic acid, methylparaben, perfume, phosphoric acid, polyvinyl alcohol, propellant a-31, propylene glycol, purified water, sodium carboxymethylcellulose, sorbic acid, stearamidoethyl diethylamine, stearic acid".

PCT Publication No. WO 03/053292 discloses drug delivery compositions, which are suitable for vaginal administration for the treatment of diseases and disorders in the urogenital tract. The compositions may be in the form of a tablet, liquid suspension or dispersion; dried powder; topical ointment; cream; foam; suppository; or aerosol. The drug delivery compositions are administered directly to the vagina and do not require the use of a pressurized canister or other foaming device. The reference does not disclose use of hydrophobic or oily solvents.

U.S. Pat. No. 5,759,520 discloses an aqueous foamable composition having a delayed foaming action on expulsion from a pressurized container. The composition includes (a) a major amount by weight of water; (b) 0.5 to 7.0 weight percent of a foaming agent in the form of a water-immiscible liquefied gas; (c) at least one foam-stabilizing and emulsifying surfactant; and (d) a water-soluble polymer. A foaming agent such as propellant gas forms a foam upon discharge from the container. Water is used as the foam vehicle and hydrophobic organic carriers such as oil or emollients are not disclosed.

PCT Publication No. WO 02/00820 discloses a propellant-free foamable aqueous composition for use as vaginal or hemorrhoidal wipe. The aqueous stable foam includes water, at least one surfactant and at least one foam-stabilizing agent. Such compounds are storage stable and readily dispensed by a propellantless mechanical pump.

U.S. Pat. No. 5,679,324 pertains to an aerosol foamable fragrance composition, translucent in its pre-dispensed state, which forms a fast-breaking foam. The composition contains a surfactant selected from the group consisting of ethoxylated lanolin oil derivatives, propoxylated lanolin oil derivatives, and mixtures thereof, a propellant, a fragrance, a thickener, and a cosmetic vehicle (preferably water) wherein the ratio of the surfactant to propellant is from about 1:1 to about 1:10. Emollients may be included, however, being translucent, the composition cannot comprise significant oil concentrations (which would make it opaque). Apparently the foam breaks spontaneously upon discharging from an aerosol container (with no need of any rubbing or sheer force application), thus making it impractical for intravaginal application.

Additionally, U.S. Pat. Nos. 5,536,743 and 5,840,744 relate to a non-flowing composition and method for intravaginal treatment of bacterial vaginosis. The composition contains metronidazole with a buffer system providing an acidic buffered pH value in the range of 3.75 to about 4.25. Certain of the compositions disclosed are based on mineral oil or petrolatum. The foam compositions disclosed include up to 3% mineral oil as the hydrophobic component of the emulsion.

U.S. Pat. No. 6,544,530 provides a stable oil-in-glycerin composition comprising a continuous glycerin phase, at least one vegetable oil, at least one biodegradable emulsifier and at least one bioactive essential oil component for topical, external use on skin and mucosal. The essential oil is a volatile mixture of esters, aldehydes, alcohols, ketones, and terpenes that possess bioactivity such as topical anti-fungal activity, topical anti-bacterial activity, topical anti-parasitic activity, and topical anti-viral activity.

U.S. Pat. No. 5,993,846 discloses a method for making an oil-in-water emulsion having mucoadhesive properties which includes forming a mixture of a mucoadhesive macromolecule and an aqueous phase; emulsifying the mixture with a hydrophobic phase and a surfactant to form an oil-in-water emulsion comprising a plurality of submicron particles having a hydrophobic core surrounded by the surfactant and the mucoadhesive macromolecule; and providing the emulsion with a final pH of between 3 and 8.

U.S. Pat. No. 6,423,323 describes an aqueous foam emulsion. The composition includes a hydrophobic phase including fatty acids, emulsifiers and co-emulsifiers, and an aqueous phase containing hydrophilic moisturizers and emulsifiers. An optional ingredient is one or more refatting substances.

U.S. Pat. No. 6,730,288 teaches a pharmaceutical foam composition including (a) an active ingredient; (b) an occlusive agent; (c) an aqueous solvent; and (d) an organic cosolvent; wherein the active ingredient is insoluble in water and insoluble in both water and the occlusive agent; and wherein there is enough occlusive agent to form an occlusive layer on the skin.

SUMMARY OF THE INVENTION

In some aspects, the present invention provides an easy to use vaginal delivery system that will be simple to operate with minimal preparation, will be very tolerable without having a feeling of foreign matter, will provide accurate dose administration, will evenly spread throughout the vaginal cavity surface, will effectively reach the cervix, will not leak and will retain intravaginally an active agent for a significant period of time. In other aspects, the present invention provides a lubricating vaginal drug vehicle for moisture replenishing or moisturizing vaginal vehicles. In other aspects, the invention provides an improved delivery system for active agents to other body cavities, such as the rectum, penile urethra, nasal cavity and ear cavity and to mucosal surfaces.

The present invention relates to foam compositions for intra-vaginal and body cavity application of a wide range of active ingredients. The compositions contain at least one active agent in a biocompatible alcohol-free foamable carrier, including oleaginous foams, oil-in-water foams, water-in-oil foams, liposome-based foams and nanoparticle-based foams. These compositions provide long lasting, drip-free, expandable formulations for drug delivery into body cavities.

According to one aspect of the present invention, an alcohol-free foamable therapeutic composition for application to a body cavity or a mucosal surface includes:

at least one organic carrier selected from a hydrophobic organic carrier, a polar solvent, an emollient and mixtures thereof hydrophobic organic carrier and mixtures thereof, at a concentration of about 2% to about 75% by weight;

about 0.2% to about 5% by weight at least one surface-active agent;

about 0.01% to about 5% by weight at least one polymeric agent, selected from a bioadhesive agent, a gelling agent, a film forming agent and a phase change agent;

at least one active agent at a therapeutically effective concentration; and a liquefied or compressed gas propellant at a concentration of about 3% to about 25% by weight of the total composition, which upon release from an aerosol container provides an expanded foam suitable for topical administration.

According to one embodiment, the composition further includes a foam adjuvant at a concentration less than about 5% by weight. Water and optional ingredients added to complete the total mass to 100%. The content of the foam compositions is presented herein as concentration (percent by weight, % w/w).

According to one or more embodiments of the present invention, the solvent level varies and can be at a level of about 2 to about 5, about 5% to about 20% by weight, or at a concentration of about 20% to about 75% by weight.

In another aspect of the present invention, an alcohol free oleaginous therapeutic foam composition for administration to a body cavity or mucosal surface includes:

at least one organic carrier selected from a hydrophobic organic carrier, an emollient, a polar solvent, and mixtures thereof, at a concentration of about 70% to about 99% by weight;

at least one surface-active agent at a concentration of about 0.2 to about 15%;

at least one polymeric agent, selected from a bioadhesive agent, a gelling agent, a film forming agent and a phase change agent at a concentration of about 0.1% to about 5% by weight;

at least one active agent at a therapeutically effective concentration; and a liquefied or compressed gas propellant at a concentration of about 3% to about 25% by weight of the total composition, which upon release from an aerosol container provides an expanded foam suitable for topical administration.

Water and optional ingredients are added to complete the total mass to 100%. As used herein "oleaginous foam composition" means a stable foam composition, or a composition capable of forming a stable foam composition that contains a high level of oil or emollient as the hydrophobic organic carrier. The hydrophobic organic carrier is included in the oleaginous foam composition at levels at or above 70%, and up to about 99% by weight.

According to one embodiment, at least one of the composition components, selected from the group consisting of organic carrier, surface active agent, foam adjuvant or polymeric agent can also function as an active agent.

In another aspect of the present invention, a method of making a foamable composition includes selecting at least one active agent; selecting a solvent that solubilizes the active agent substantially better than a hydrocarbon solvent such as mineral oil or petrolatum, for example, 5 fold better than mineral oil or petrolatum, or even 10-fold better than mineral oil or petrolatum; and adjusting the type and concentration of surfactant and gelling agent, to provide a foamable composition.

According to another aspect of the present invention, a method of treating a syndrome, disease or disorder of a body cavity or mucosal surface includes administering an alcohol-free foamable therapeutic composition. The foamable composition can be an oleaginous foam, an oil-in-water foam, a water-in-oil foam, a liposome based foam and a nanoparticle based foam.

In one or more embodiments of the present invention, the syndrome, disorder or disease of the body cavity is a syndrome, disorder or disease of the vaginal cavity. In one or more embodiments, the disorder is a microbial disorder including bacterial vaginosis, candidiasis, candidal vaginitis and trichomonas vaginitis. In another embodiment the microbial disorder is a sexually transmitted disease (STD) such as chlamydia, herpes simplex, human immunodeficiency virus (HIV). In another embodiment the syndrome, disorder or disease of the vaginal cavity is related to hormonal or post-menopausal vaginal dryness. In yet another embodiment the syndrome, disorder or disease is related to the cervix and includes malignant and benign tumors, dysplasias, human papillomavirus (HPV) or to the vulva and includes lichen sclerosus, vulvodynia and other pathologies.

DETAILED DESCRIPTION OF THE INVENTION

The present invention provides a foamable therapeutic compositions useful for delivery of an active agent to a mucosal body cavity. The composition is dispensed as a foam providing a stable product that is pleasant and easy to use for high patient compliance.

The foamable therapeutic composition of the present invention is suitable for facile administration into the rectum, bladder, the cavity between the uterus and the fallopian tubes, the ovaries and other body areas, which may accept topically-applied products.

In one or more embodiments of the present invention, a foamable composition includes water in one phase and at least one solvent selected from a hydrophobic organic carrier, a polar solvent, an emollient and mixtures thereof in the second phase. The compositions may be water-in-oil or oil-in-water emulsions.

Despite the commonly accepted understanding that hydrophobic organic carriers, polar solvents and emollients are difficult to formulate into a foam-producing product and that addition of such solvents interferes with the foam forming ability of a surfactant, the present invention has surprisingly identified a series of foam compositions, which, upon admixing with a liquefied gas propellant in an aerosol container, produce a stable foam composition that is suitable for topical and mucosal administration to body cavities, such as the vagina, rectum, penile, urethra, nasal cavity and ear cavity. Upon discharge from an aerosol container, the composition forms an expanded foam, which does not break down immediately upon discharge, and remains in the body cavity for an extended time.

Such compositions, when placed in an aerosol container and combined with a liquefied gas propellant, create an emulsion, which, upon release from the aerosol container, provides a therapeutically beneficial foam product.

According to one or more embodiments of the present invention, the therapeutic foam composition for administration to a body cavity or mucosal surface includes at least one solvent selected from a hydrophobic organic carrier, a polar solvent, an emollient and mixtures thereof, at a level of about 2% to about 5%, or about 5% to about 10%; or about 10% to about 20%; or about 20% to about 75%; or about 70% to about 99% by weight. The composition also contains about 0.2% to about 5% by weight of a surface-active agent; about 0.01% to about 5% by weight of a polymeric additive selected from a bioadhesive agent, a gelling agent, a film forming agent and a phase change agent; at least one active agent at a therapeutically effective concentration; and a liquefied gas propellant at a concentration of about 3% to about 25% by weight of the total composition, which upon release from an aerosol container provides an expanded foam suitable for topical administration.

According to one embodiment, the composition further comprises a foam adjuvant at a concentration less than about 5%.

Water (to make an emulsion) and optional ingredients are added to complete the total mass to 100%. Upon release from an aerosol container, the foamable composition forms an expanded foam suitable for topical administration.

In one or more embodiments, the foam composition is formulated as an emulsion and can be an oil-in-water emulsion or a water-in-oil emulsion. The choice of the type of emulsion (oil-in-water or water-in-oil) is made in light of the nature of the active agent, so that it is suitable for inclusion of either or both water-soluble and oil-soluble active agents. The choice of the type of emulsion is also influenced by the type of interaction which is desirable between the composition, the active agent and the target tissue.

In one or more embodiments, the emulsion is a microemulsion. Microemulsions are dispersions of either oil-in-water or water-in-oil, which are typically clear, as the droplet diameter is approximately 100 nanometers (nm) or less.

In one or more embodiments, the foam composition of the present invention comprises liposomes.

In one or more embodiments, the foam composition of the present invention comprises nanoparticles, and, for example, the diameter is about 200 nm to about 400 nm. Nanoparticles are typically introduced as an active agent.

The foam composition may include a propellant substance in an amount of about 3% to about 25% by weight, housed in an aerosol container.

When released, the composition produces a foam, suitable for facile administration into body orifices and mucosal cavities, including, but not limited to the the vagina, the rectum and penile cavities, the urinary tract, bladder, the cavity between the uterus and the fallopian tubes, the ovaries and other body areas, which may accept topically-applied products.

It has been surprisingly discovered that the propellant helps provide a stable emulsion. The propellant makes up part of the "oil phase" component of the emulsion, providing a product with long shelf-life. Thus, admixing the liquid and solid foam components with a short chain hydrocarbon propellant, results in a stable emulsion, that does not undergo phase separation after stress test, including either exposure to at least two freeze and though cycles.

The terms "therapy" and "treatment" as used herein interchangeably, cover any treatment of a disease or disorder, and includes, for example, curing the disease or disorder, preventing the disease or disorder from occurring in a subject which may be predisposed to the disease but has not yet been diagnosed with the disease or disorder, inhibiting the disease or disorder, relieving the disease or disorder, providing a prophylactic effect, evolving a beneficial immunological effect; and improving the quality of life of a subject afflicted by a disease or disorder.

In one or more embodiments of the present invention, a therapeutic product is provided that includes an active agent in a therapeutically effective concentration. Active agents are included in each of the compositions described herein; however, in some instances the solvent, which is part of the composition, provides therapeutic benefit and thus, can be defined as the at least one active agent. Therapeutic products are intended for topical treatment of human and animal disorders of body cavities, or any other disorder, that requires topical application of a drug into a body cavity.

The foamable composition of the present invention can be an emulsion, or microemulsion, including an aqueous phase and an organic carrier phase. The organic carrier is selected from a hydrophobic organic carrier (also termed herein "hydrophobic solvent"), an emollient, a polar solvent, and a mixture thereof.

A "hydrophobic organic carrier" as used herein refers to a material having solubility in distilled water at ambient temperature of less than about 1 gm per 100 mL, more preferable less than about 0.5 gm per 100 mL, and most preferably less than about 0.1 gm per 100 mL. It is liquid at ambient temperature. The identification of a hydrophobic organic carrier or "hydrophobic solvent", as used herein, is not intended to characterize the solubilization capabilities of the solvent for any specific active agent or any other component of the foamable composition. Rather, such information is provided to aid in the identification of materials suitable for use as a hydrophobic carrier in the foamable compositions described herein.

In one or more embodiments, the hydrophobic organic carrier is an oil, such as mineral oil. Mineral oil (Chemical Abstracts Service Registry number 8012-95-1) is a mixture of aliphatic, naphthalenic, and aromatic liquid hydrocarbons that derive from petroleum. It is typically liquid; its viscosity is in the range of between about 35 CST and about 100 CST (at 40° C.), and its pour point (the lowest temperature at which an oil can be handled without excessive amounts of wax crystals forming so preventing flow) is below 0° C. Term hydrophobic organic carrier does not include thick or semi-solid materials, such as white petrolatum, also termed "Vaseline", which, in certain compositions is disadvantageous due to its waxy nature and semi-solid texture.

According to one or more embodiments, hydrophobic solvents are liquid oils originating from vegetable, marine or animal sources. Suitable liquid oil includes saturated, unsaturated or polyunsaturated oils. By way of example, the unsaturated oil may be olive oil, corn oil, soybean oil, canola oil, cottonseed oil, coconut oil, sesame oil, sunflower oil, borage seed oil, syzigium aromaticum oil, hempseed oil, herring oil, cod-liver oil, salmon oil, flaxseed oil, wheat germ oil, evening primrose oils or mixtures thereof, in any proportion.

Suitable hydrophobic solvents also include polyunsaturated oils containing poly-unsaturated fatty acids. In one or more embodiments, the unsaturated fatty acids are selected from the group of omega-3 and omega-6 fatty acids. Examples of such polyunsaturated fatty acids are linoleic and linolenic acid, gamma-linoleic acid (GLA), eicosapentaenoic acid (EPA) and docosahexaenoic acid (DHA). Such unsaturated fatty acids are known for their skin-conditioning effect, which contribute to the therapeutic benefit of the present foamable composition. Thus, the hydrophobic solvent can include at least 6% of an oil selected from omega-3 oil, omega-6 oil, and mixtures thereof. In the context of the present invention, oils that possess therapeutically-beneficial properties are termed "therapeutically active oil".

Another class of hydrophobic solvents is the essential oils, which are also considered therapeutically active oil, which contain active biologically occurring molecules and, upon topical application, exert a therapeutic effect, which is conceivably synergistic to the beneficial effect of the steroid in the composition.

Another class of therapeutically active oils includes liquid hydrophobic plant-derived oils, which are known to possess therapeutic benefits when applied topically.

Silicone oils also may be used and are desirable due to their known skin protective and occlusive properties. Suitable silicone oils include non-volatile silicones, such as polyalkyl siloxanes, polyaryl siloxanes, polyalkylaryl siloxanes and polyether siloxane copolymers, polydimethylsiloxanes (dimethicones) and poly(dimethylsiloxane)-(diphenyl-siloxane) copolymers. These are chosen from cyclic or linear polydimethylsiloxanes containing from about 3 to about 9, preferably from about 4 to about 5, silicon atoms. Volatile silicones such as cyclomethicones can also be used. Silicone oils are also considered therapeutically active oil, due to their barrier retaining and protective properties.

In one or more embodiments, the hydrophobic carrier includes at least 2% by weight silicone oil or at least 5% by weight.

The solvent may be a mixture of two or more of the above hydrophobic solvents in any proportion.

A further class of solvents includes "emollients" that have a softening or soothing effect, especially when applied to body areas, such as the skin and mucosal surfaces. Emollients are not necessarily hydrophobic. Examples of suitable emollients include hexyleneglycol, propylene glycol, isostearic acid derivatives, isopropyl palmitate, isopropyl isostearate, diisopropyl adipate, diisopropyl dimerate, maleated soybean oil, octyl palmitate, cetyl lactate, cetyl ricinoleate, tocopheryl acetate, acetylated lanolin alcohol, cetyl acetate, phenyl trimethicone, glyceryl oleate, tocopheryl linoleate, wheat germ glycerides, arachidyl propionate, myristyl lactate, decyl oleate, propylene glycol ricinoleate, isopropyl lanolate, pentaerythrityl tetrastearate, neopentylglycol dicaprylate/dicaprate, isononyl isononanoate, isotridecyl isononanoate, myristyl myristate, triisocetyl citrate, octyl dodecanol, sucrose esters of fatty acids, octyl hydroxystearate and mixtures thereof.

According to one or more embodiments of the present invention, the hydrophobic organic carrier includes a mixture of a hydrophobic solvent and an emollient. According to one or more embodiments, the foamable composition is a mixture of mineral oil and an emollient in a ratio between 2:8 and 8:2 on a weight basis.

A "polar solvent" is an organic solvent, typically soluble in both water and oil. Examples of polar solvents include polyols, such as glycerol (glycerin), propylene glycol, hexylene glycol, diethylene glycol, propylene glycol n-alkanols, terpenes, di-terpenes, tri-terpenes, terpen-ols, limonene, terpeneol, 1-menthol, dioxolane, ethylene glycol, other glycols, sulfoxides, such as dimethylsulfoxide (DMSO), dimethylformanide, methyl dodecyl sulfoxide, dimethylacetamide, monooleate of ethoxylated glycerides (with 8 to 10 ethylene oxide units), azone (1-dodecylazacycloheptan-2-one), 2-(n-nonyl)-1,3-dioxolane, esters, such as isopropyl myristate/palmitate, ethyl acetate, butyl acetate, methyl proprionate, capric/caprylic triglycerides, octylmyristate, dodecyl-myristate; myristyl alcohol, lauryl alcohol, lauric acid, lauryl lactate ketones; amides, such as acetamide oleates such as triolein; various alkanoic acids such as caprylic acid; lactam compounds, such as azone; alkanols, such as dialkylamino acetates, and admixtures thereof.

According to one or more embodiments, the polar solvent is a polyethylene glycol (PEG) or PEG derivative that is liquid at ambient temperature, including PEG200 (MW (molecular weight) about 190-210 kD), PEG300 (MW about 285-315 kD), PEG400 (MW about 380-420 kD), PEG600 (MW about 570-630 kD) and higher MW PEGs such as PEG 4000, PEG 6000 and PEG 10000 and mixtures thereof.

In one or more embodiments, the solvent is a mixture (emulsion) of a hydrophobic organic carrier and glycerin, as described, for example, in U.S. Pat. No. 6,544,530. The ratio of hydrophobic organic carrier to glycerin can range from about 1:4 to about 4:1, and more preferably from about 1:2 to about 2:1.

In certain cases, a given solvent can be defined as both emollient and polar solvent.

Certain hydrophobic organic carriers, emollients and polar solvents possess high solubilization capacity for pharmaceutical active agents, and are identified herein as "potent solvents". A potent solvent as that term is used herein, is one that solubilizes a specific active agent substantially better than mineral oil or petrolatum, preferably 5 fold better than mineral oil or petrolatum, and even 10-fold better than mineral oil or petrolatum, and even 100-fold better than mineral oil or petrolatum.

Thus, in one or more embodiments, a foam composition includes at least one active agent in a therapeutically effective concentration and a potent solvent. In one or more embodiments, the composition includes at least one active agent in a therapeutically effective concentration and at least one potent solvent in a sufficient amount to substantially solubilize the active agent in the composition. In the context of the present invention the term "substantially soluble" means that at least 95% of the active agent has been solubilized, i.e., less than about 5% is present in the composition in a solid state. In one or more embodiments, the potent solvent is more than about 40% or more than about 60% by weight of the total solvent of the composition.

Examples of active agent/potent solvent combinations include, in a non-limiting manner:

Betamethasone valerate: Practically insoluble in mineral oil (<0.01%); soluble more than 1% (w/w) in Glycofurol.

Hydrocortisone butyrate: Practically insoluble in mineral oil (<0.01%); soluble more than 1% in Glycofurol.

Metronidazole: Practically insoluble in mineral oil (<0.01%); soluble more than 1% in dimethyl isosorbide.

Ketoconazole: Practically insoluble in mineral oil (<0.01%); soluble more than 1% in glycofurol, propylene glycol and dimethyl isosorbide.

Mupirocin: Practically insoluble in mineral oil (<0.01%); soluble more than 1% in glycofurol, hexylene glycol, dimethyl isosorbide, propylene glycol and polyethylene glycol 400 (PEG 400).

Meloxicam, a nonsteroidal anti-inflammatory agent: Practically insoluble in mineral oil (<0.001%); soluble in propylene glycol: 0.3 mg/mL and in PEG 400: 3.7 mg/mL.

Progesterone: Practically insoluble in mineral oil (<0.001%); soluble in PEG 400: 15.3 mg/mL.

A non-limiting exemplary list of solvents that can be considered as potent solvents includes polyethylene glycol, propylene glycol, hexylene glycol, butanediols and isomers thereof, glycerol, benzyl alcohol, DMSO, ethyl oleate, ethyl caprylate, dimethylacetamide, N-methylpyrrolidone, N-hydroxyethylpyrrolidone, polyvinylpyrrolidone, isosorbide derivatives, such as dimethyl isosorbide, glycofurol and ethoxydiglycol (transcutol).

The present invention also provides a method of designing a foamable composition by selecting at least one active agent, selecting a solvent that solubilizes the active agent substantially better than mineral oil or petrolatum, and adjusting the type and concentration of surfactant and gelling agent to provide a foamable composition. This is particularly useful in fomulating foams incorporating poorly soluble active agents.

The use of a potent solvent in a foam composition provides an improved way to deliver poorly soluble active agents to a target area. It is known that low drug solubility results in poor bioavailability, leading to decreased effectiveness of treatment. Foam compositions according to one or more embodiments of the present invention for which the solvent is a potent solvent are unique because the majority of the active agent is in solution, rather than in particulate form, resulting in high delivery and improved therapy.

Potent solvents are typically in liquid form. Liquid drug formulations are generally disadvantageous, since their usage causes unwanted dripping, resulting in inconvenience and inadequate dosing. Unexpectedly, the foams of the present invention are drip-free and thereby provide a superior vehicle for such drugs and enable convenient usage and accurate effective dosing.

Surface-active agents (surfactants) include any agent linking oil and water in the composition in the form of emulsion. A surfactant's hydrophilic/lipophilic balance (HLB) describes the emulsifier's affinity toward water or oil. The HLB scale ranges from 1 (totally lipophilic) to 20 (totally hydrophilic), with 10 representing an equal balance of both characteristics. Lipophilic emulsifiers form water-in-oil (w/o) emulsions, whereas hydrophilic surfactants form oil-in-water (o/w) emulsions. The HLB of a blend of two emulsifiers equals the weight fraction of emulsifier A times its HLB value plus the weight fraction of emulsifier B times its HLB value (weighted average).

Any surface-active agent or combinations thereof may be used as surface-active agent. According to one or more embodiments of the present invention, the surface-active agent has a hydrophilic lipophilic balance (HLB) between about 9 and about 14, which is the required HLB (the HLB required to stabilize an O/W emulsion of a given oil) of most oils and hydrophobic organic carriers. Thus, in one or more embodiments, the composition is a single surface active agent having an HLB value between about 9 and 14, and in one or more embodiments, the composition is more than one surface active agent and the weighted average of their HLB values is between about 9 and about 14.

According to one or more embodiments, the surface-active agent in an oleaginous composition (hydrophobic organic carriers of 70% or greater) has a surface-active agent with an HLB in the range of about 3 to about 9.

The surface-active agent is selected from anionic, cationic, nonionic, zwitterionic, amphoteric and ampholytic surfactants, as well as mixtures of these surfactants. Such surfactants are well known to those skilled in the therapeutic and cosmetic formulation art. Nonlimiting examples of possible surfactants include polysorbates, such as polyoxyethylene (20) sorbitan monostearate (Tween 60) and poly(oxyethylene) (20) sorbitan monooleate (Tween 80); poly(oxyethylene) (POE) fatty acid esters, such as Myrj 45, Myrj 49, Myrj 52 and Myrj 59; poly(oxyethylene) alkylyl ethers, such as poly(oxyethylene) cetyl ether, poly(oxyethylene) palmityl ether, polyethylene oxide hexadecyl ether, polyethylene glycol cetyl ether, brij 38, brij 52, brij 56 and brij W1; sucrose esters, partial esters of sorbitol and its anhydrides, such as sorbitan monolaurate and sorbitan monolaurate; mono or diglycerides, isoceteth-20, sodium methyl cocoyl taurate, sodium methyl oleoyl taurate, sodium lauryl sulfate, triethanolamine lauryl sulfate and betaines.

In one or more embodiments of the present invention, the surface-active agent includes at least a non-ionic surfactant. Ionic surfactants are known to be irritants. Therefore, non-ionic surfactants are preferred in applications including sensitive tissue such as found in most mucosal tissues, especially when they are infected or inflamed. We have surprisingly found that non-ionic surfactants alone provide foams of excellent quality, i.e. a score of "E" according to the grading scale discussed herein below.

In one or more embodiments, the surface active agent includes a mixture of at least one non-ionic surfactant and at least one ionic surfactant in a ratio in the range of about 100:1 to 6:1. In one or more embodiments, the non-ionic to ionic surfactant ratio is greater than about 6:1, or greater than about 8:1; or greater than about 14:1, or greater than about 16:1, or greater than about 20:1.

In one or more embodiments of the present invention, a combination of a non-ionic surfactant and an ionic surfactant (such as sodium lauryl sulphate and cocamidopropylbetaiine) is employed, at a ratio of between 1:1 and 20:1, or at a ratio of 4:1 to 10:1. The resultant foam has a low specific gravity, e.g., less than 0.1 g/ml.

In one or more embodiments of the present invention, the surface-active agent includes mono-, di- and tri-esters of sucrose with food fatty acids (sucrose esters), prepared from sucrose and esters of fatty acids or by extraction from sucroglycerides. Suitable sucrose esters include those having high monoester content, which have higher HLB values.

Unlike prior art foamable compositions, the total surface active agent required to obtain a foam that is stable, of low specific gravity and has a fine bubble structure is low. This is desirable because lower surface active agent levels, particularly of ionic surfactants, reduce skin irritations. Total surface active agent is in the range of about 0.1 to about 5% of the foamable composition, and is typically less than about 2%, preferably less than about 1%.

It has been unexpectedly found that it is possible to prepare stable foams with stabilizing surfactants even in very low concentration of less than about 1% which enable low irritating and low itching vaginal foams. "Stable foam" denotes shelf life stability of the emulsion and also a sustainable foam that does not break upon extrusion of the package to enable delivery, spreading and expansion of the foam throughout the entire vaginal cavity before collapse.

The foamable composition includes a polymeric agent to increase the duration/residence time of the composition in the body cavity. The polymeric agent serves to stabilize the foam composition and to control drug duration in the target organ.

Exemplary polymeric agents, which provide means of controlling duration are classified below in a non-limiting manner. In certain cases, a given polymer can belong to more than one of the classes provided below.

Bioadhesion has been defined as the attachment of synthetic or biological macromolecules to a biological tissue. The term mucoadhesion refers to the special case of bioadhesion where the biological tissue is an epithelium covered by mucous, for example such as found in the vagina, gastrointestinal tract and the nasal cavity. Mucoadhesive agents are a class of polymeric biomaterials that exhibit the basic characteristic of a hydrogel, i.e. swell by absorbing water and interacting by means of adhesion with the mucous that covers epithelia.

Compositions of the present invention may contain a mucoadhesive macromolecule or polymer in an amount sufficient to confer bioadhesive properties. The bioadhesive macromolecule enhances the delivery of biologically active agents on or through the target surface. The mucoadhesive macromolecule may be selected from acidic synthetic polymers, preferably having at least one acidic group per four repeating or monomeric subunit moieties, such as poly (acrylic)- and/or poly(methacrylic) acid (e.g., Carbopol®, Carbomer®), poly(methylvinyl ether/maleic anhydride) copolymer, and their mixtures and copolymers; acidic synthetically modified natural polymers, such as carboxymethylcellulose (CMC); neutral synthetically modified natural polymers, such as (hydroxypropyl)methylcellulose; basic amine-bearing polymers such as chitosan; acidic polymers obtainable from natural sources, such as alginic acid, hyaluronic acid, pectin, gum tragacanth, and karaya gum; and neutral synthetic polymers, such as polyvinyl alcohol or their mixtures. An additional group of mucoadhesive polymers includes natural and chemically modified cyclodextrin, especially hydroxypropyl-β-cyclodextrin (HPβCD). Such polymers may be present as free acids, bases, or salts, usually in a final concentration of about 0.01% to about 0.5% by weight.

A suitable bioadhesive macromolecule is the family of acrylic acid polymers and copolymers, (e.g., Carbopol®). These polymers contain the general structure —[$CH_2$—CH(COOH)—]$_n$. Hyaluronic acid and other biologically-derived polymers may be used.

Exemplary bioadhesive or mucoadhesive macromolecules have a molecular weight of at least 50 kDa, or at least 300 kDa, or at least 1,000 kDa. Favored polymeric ionizable macromolecules have not less than 2 mole percent acidic groups (e.g., COOH, $SO_3H$) or basic groups ($NH_2$, NRH, $NR_2$), relative to the number of monomeric units. The acidic or basic groups can constitute at least 5 mole percent, or at least 10 mole percent, or at least 25, at least 50 more percent, or even up to 100 mole percent relative to the number of monomeric units of the macromolecule.

Yet, another group of mucoadhesive agent includes inorganic gelling agents such as silicon dioxide (fumed silica), including but not limited to, AEROSIL 200 (DEGUSSA).

Many mucoadhesive agents are known in the art to also possess gelling properties.

A gelling agent controls the residence of a therapeutic composition in the target site of treatment by increasing the viscosity of the composition, thereby limiting the rate of its clearance from the site. Many gelling agents are known in the art to possess mucoadhesive properties.

The gelling agent can be a natural gelling agent, a synthetic gelling agent and an inorganic gelling agent. Exemplary gelling agents that can be used in accordance with one or more embodiments of the present invention include, for example, naturally-occurring polymeric materials, such as locust bean gum, sodium alginate, sodium caseinate, egg albumin, gelatin agar, carrageenin gum, sodium alginate, xanthan gum, quince seed extract, tragacanth gum, guar gum, starch, chemically modified starches and the like, semi-synthetic polymeric materials such as cellulose ethers (e.g. hydroxyethyl cellulose, methyl cellulose, carboxymethyl cellulose, hydroxy propylmethyl cellulose), guar gum, hydroxypropyl guar gum, soluble starch, cationic celluloses, cationic guars, and the like, and synthetic polymeric materials, such as carboxyvinyl polymers, polyvinylpyrrolidone, polyvinyl alcohol, polyacrylic acid polymers, polymethacrylic acid polymers, polyvinyl acetate polymers, polyvinyl chloride polymers, polyvinylidene chloride polymers and the like. Mixtures of the above compounds are contemplated.

Further exemplary gelling agents include the acrylic acid/ethyl acrylate copolymers and the carboxyvinyl polymers sold, for example, by the B.F. Goodrich Company under the trademark of Carbopol® resins. These resins consist essentially of a colloidal water-soluble polyalkenyl polyether crosslinked polymer of acrylic acid crosslinked with from 0.75% to 2% of a crosslinking agent such as polyallyl sucrose or polyallyl pentaerythritol. Examples include Carbopol® 934, Carbopol® 940, Carbopol® 950, Carbopol® 980, Carbopol® 951 and Carbopol® 981. Carbopol® 934 is a water-soluble polymer of acrylic acid crosslinked with about 1% of a polyallyl ether of sucrose having an average of about 5.8 allyl groups for each sucrose molecule.

Yet, another group of gelling agents includes inorganic gelling agents, such as silicone dioxide (fumed silica).

According to one or more embodiments, the foam composition contains at least one film forming component. The film forming component may include at least one water-insoluble alkyl cellulose or hydroxyalkyl cellulose. Exemplary alkyl cellulose or hydroxyalkyl cellulose polymers include ethyl cellulose, propyl cellulose, butyl cellulose, cellulose acetate, hydroxypropyl cellulose, hydroxybutyl cellulose, and ethylhydroxyethyl cellulose, alone or in combination. In addition, a plasticizer or a cross linking agent may be used to modify the polymer's characteristics. For example, esters such as dibutyl or diethyl phthalate, amides such as diethyldiphenyl urea, vegetable oils, fatty acids and alcohols such as oleic and myristyl acid may be used in combination with the cellulose derivative.

In one or more embodiments, the composition of the present invention includes a phase change polymer, which alters the composition behavior from fluid-like prior to administration to solid-like upon contact with the target mucosal surface. Such phase change results from external stimuli, such as changes in temperature or pH and exposure to specific ions (e.g., Ca++).

Non-limiting examples of phase change polymers include poly(N-isopropylamide), Poloxamer 407® and Smart-Gel® (Poloxamer+PAA).

The polymeric agent is present in an amount in the range of about 0.01% to about 5.0% by weight of the foam composition. In one or more embodiments, it is typically less than about 1 wt % of the foamable composition.

A foam adjuvant is optionally included in the foamable compositions of the present invention to increase the foaming capacity of surfactants and/or to stabilize the foam. In one or more embodiments of the present invention, the foam adjuvant agent includes fatty alcohols having 15 or more carbons in their carbon chain, such as cetyl alcohol and stearyl alcohol (or mixtures thereof). Other examples of fatty alcohols are arachidyl alcohol (C20), behenyl alcohol (C22), 1-triacontanol (C30), as well as alcohols with longer carbon chains (up to C50). Fatty alcohols, derived from beeswax and including a mixture of alcohols, a majority of which has at least 20 carbon atoms in their carbon chain, are especially well suited as foam adjuvant agents. The amount of the fatty alcohol required to support the foam system is inversely related to the length of its carbon chains.

In one or more embodiments of the present invention, the foam adjuvant agent includes fatty acids having 16 or more carbons in their carbon chain, such as hexadecanoic acid (C16) stearic acid (C18), arachidic acid (C20), behenic acid (C22), octacosanoic acid (C28), as well as fatty acids with longer carbon chains (up to C50), or mixtures thereof. As for fatty alcohols, the amount of fatty acids required to support the foam system is inversely related to the length of its carbon chain.

Optionally, the carbon atom chain of the fatty alcohol or the fatty acid may have at least one double bond. A further class of foam adjuvant agent includes a branched fatty alcohol or fatty acid. The carbon chain of the fatty acid or fatty alcohol also can be substituted with a hydroxyl group, such as 12-hydroxy stearic acid.

The foam adjuvant according to one or more embodiments of the present invention includes a mixture of fatty alcohols, fatty acids and hydroxy fatty acids and derivatives thereof in any proportion, providing that the total amount is 0.1% to 5%

(w/w) of the carrier mass. More preferably, the total amount is 0.4%-2.5% (w/w) of the carrier mass.

While fatty alcohols and fatty acids serve to stabilize the resultant foam composition, they often provide additional therapeutic properties. Long chain saturated and mono unsaturated fatty alcohols, e.g., stearyl alcohol, erycyl alcohol, arachidyl alcohol and docosanol have been reported to possess antiviral, anti infective, anti-proliferative and anti-inflammatory properties (U.S. Pat. No. 4,874,794). Longer chain fatty alcohols, e.g., tetracosanol, hexacosanol, heptacosanol, octacosanol, triacontanol, etc. are also known for their metabolism modifying properties and tissue energizing properties. Long chain fatty acids have also been reported to possess anti-infective characteristics. Thus, the therapeutic or cosmetic carrier, containing the foam adjuvant agent of the present invention provides an extra therapeutic benefit in comparison with currently used vehicles, which are inert and non-active.

Lower alcohols having up to 5 carbon atoms in their carbon chain skeleton, such as ethanol, propanol, isopropanol, butanol, iso-butanol, t-butanol and pentanol, are considered less desirable solvents or polar solvents due to their skin-irritating effect. Thus, the composition is substantially alcohol-free and should comprise less than about 5% final concentration of lower alcohols, preferably less than about 2%, more preferably less than about 1%.

The therapeutic foam of the present invention may further optionally include a variety of formulation excipients, which are added in order to fine-tune the consistency of the formulation, protect the formulation components from degradation and oxidation and modify their consistency. Such excipients may be selected, for example, from stabilizing agents, antioxidants, humectants, preservatives, colorant and odorant agents and other formulation components, used in the art of formulation.

Aerosol propellants are used to generate and administer the foamable composition as a foam. The total composition including propellant, foamable compositions and optional ingredients is referred to as the foamable carrier. The propellant makes up about 3% to about 25 wt % of the foamable carrier. Examples of suitable propellants include volatile hydrocarbons such as butane, propane, isobutane or mixtures thereof, and fluorocarbon gases.

Composition and Foam Physical Characteristics

The compositions described herein, including water, additional solvents, formulation excipients, active agents and propellant creates a stable emulsion that does not exhibit full phase separation at ambient temperature for at least a year.

Yet, another property of a composition is its level of flow, since a composition that is not free flowing cannot flow through the dip-tube of the aerosol container and create acceptable foam. It has been noted that in the context of the composition of the present invention, compositions including semi-solid hydrophobic organic carriers, e.g., white petrolatum, are excessively viscous and demonstrate poor flowability.

The combination of at least one surface active agent, at least one polymeric agent and optionally at least one foaming adjuvant, according to one or more embodiments of the invention provides a low specific gravity foam having superior expandability, flow properties and sheer breakability (among other attributes). According to one or more embodiments of the present invention, the total amount of at least one surface active agent, at least one polymeric agent and optionally at least one foaming adjuvant, in combination does not exceed 8% (w/w) of foamable composition. In one or more embodiments, the combined amounts of at least one surface active agent, at least one polymeric agent and optionally at least one foaming adjuvant is less than 5% (w/w) of foam composition. The low solid content improves the flow properties of the foam, reduces unpleasant skin residue and reduces the cost of manufacture. As is demonstrated herein, the foam stability and expandability are excellent, despite the low levels of these components in the foam.

Expandability is an important feature of a product that is intended to treat internal cavities of the body. Thus, in one or more embodiments of the present invention, the specific gravity of the foam, upon discharge from the foam dispenser is between about 0.02 gr/mL and 0.4 gr/mL, or between about 0.04 gr/mL and about 0.14 gr/mL.

The following scale for foam quality is used to evaluate foams.

E (excellent): very rich and creamy in appearance, does not show any bubble structure or shows a very fine (small) bubble structure.
G (good): rich and creamy in appearance, very small bubble size, "dulls" more rapidly than an excellent foam.
FG (fairly good): a moderate amount of creaminess noticeable, bubble structure is noticeable.
F (fair): very little creaminess noticeable, larger bubble structure than a "fairly good" foam.
P (poor): no creaminess noticeable, large bubble structure.
VP (very poor): dry foam, large very dull bubbles, difficult to spread on the skin.

Foams that are adequate for topical administration according to the present invention have to be of quality grade E or G, upon release from the foam dispenser. Smaller bubbles mean more stable foam, which does not collapse spontaneously immediately upon discharge from the container. The finer foam structure looks and feels smoother, thus increasing its usability and appeal.

In one or more embodiments, the foam compositions are stable for a prolonged period of time. Thus, the foam composition does not undergo phase separation following at least two freeze and thaw cycles.

Upon discharge from a foam dispenser, e.g., an aerosol can, onto a mucosal membrane at about 37° C., the foam expands to reach its designated volume and stays stable as a foam for at least 60 seconds, or 2 minutes, or even 3 minutes, following application.

Metered Dosing

In order to provide proper therapy, precise dosing is desired. According to one or more embodiments, the foam therapeutic product is adapted for storage in a foam dispenser having a metered dose valve for dispensing an accurate dose of drug in the form of a foam. The metered dose valve is selected to release a foam in a volume that is in the size of the target body cavity to allow effective spreading of the active agent throughout the body cavity with substantially minimal overflow.

In one or more embodiments, the meter dose valve provides a unit dose of between about 10 µL and about 1000 µL. Assuming a representative foam density (specific gravity) of 0.06 g/mL, a 10 µL valve provides a volume of about 0.17 mL of foam, and a 1000 µL metered dose valve provides about 17 mL of foam. Thus, by selecting a specific metered dosing valve and adjusting the foam density by fine tuning formulation parameters and adjusting the ration between the liquid components of the composition and the propellant, one can design an adequate dosage form according to the specific target organ cavity Administration One limitation of existing vaginal and rectal dosage form relates to the dimensions of the product applicator. In order to administer 5 mL of gel (which is required to attain effective coverage of the vaginal surface), an insert applicator, 10 cm long and about 1.5 cm thick is employed. It is to be understood that such a thick applicator is found repulsive by patients, which leads to poor patient compliance. Furthermore, the length of the applicator, which is beyond the natural depth of a relaxed vaginal cavity, makes it difficult for the patient to accurately administer the composition into the target organ.

By contrast, application of a foam composition according to the present invention is not limited by applicator dimensions. The insert is thin and thus, it is acceptable to the patient. The thickness of the aerosol insert can range between about 0.2 cm and about 1 cm. Likewise, the aerosol insert can be designed in any length, to fit the dimensions of the target organ. Thus, the length of a vaginal insert can range between about 2 cm and about 10 cm; the length of an insert for the nasal system or ear canal can be shorter and the insert for rectal administration can be adjusted according to the location of the disorder, between about 1 cm and about 20 cm. In one or more embodiments, the insert is designed to be flexible, to allow insertion into a body cavity that is difficult to access using a non-flexible insert.

Fields of Application

By including an appropriate active agent in the foamable composition, it is useful in the therapy and prevention of a variety of disorders of a body cavity or mucosal surfaces, including, but not limited to the cranial cavity, the thoracic cavity, the abdominal cavity, the ventral cavity, the vagina, the rectum and penile cavities, the urinary tract, bladder, the cavity between the uterus and the fallopian tubes, the ovaries, the nasal cavity, the mouth, the eye, the ear the peritoneum, the large and small bowel, the caecum, bladder, and stomach, and other body cavities or spaces, which may accept topically-applied products.

Exemplary treatable disorders are listed below.

Bacterial, Fungal and Viral Infections

Bacterial, fungal and viral infections: a variety of anti-infective, anti-bacterial, anti-fungal and anti-viral agents can be included in the foam of the present invention, to be used for the treatment and/or prevention of diseases, such as chlamydia, gonorrhea, hepatitis B, herpes, HIV/AIDS, human papallomavirus (HPV) & genital warts; syphilis; bacterial vaginosis, candidiasis, chancroid, granuloma inguinale, lymphogranloma venereum, mucopurulent cervicitis (MPC), molluscum contagiosum, nongonococcal urethritis (NGU), trichomoniasis, and vulvar disorders.

A variety of active agents, known in the art, can be included in the foam to be used for the treatment and/or prevention of diseases such as vulvodynia (vulvar pain), yeast infections, genital warts (condyloma) vulvar dystrophy, vulvar intraepithelial neoplasia (VIN), invasive cancer of the vulva, contact dermatitis, pelvic inflammation, pelvic inflammatory disease (PID), genital cancer and cancer of the cervix, vulva or vagina.

Vaginal Dryness

Vaginal dryness is caused by a number of conditions and can be either an occasional hassle or a chronic problem. A variety of anti-inflammatory active agents, hormones, moisturizing, refatting and lubricating agents and local anesthetic agents can be included in the foam of the present invention, to be used for the treatment and/or prevention of vaginal dryness.

Dyspareunia

Dysareunia is pain in the vagina or pelvis experienced during sexual intercourse. A variety of anti-inflammatory active agents, hormones, moisturizing, refatting and lubricating agents and local anesthetic agents can be included in the foam of the present invention, to be used for the treatment and/or prevention of vaginal pain. Anal and rectal disease, such as anal abscess/fistula, anal cancer, anal fissure, anal warts, Crohn's disease, hemorrhoids, anal itch, also called pruritus ani, fecal incontinence, and polyps of the colon and rectum all may be treated using the foamable composition according to one or more embodiments of the invention.

The foam composition of the present invention, comprising an active agent that is known to treat one of said anorectal disorders and administered rectally, expands effectively in the rectal cavity and provides optimal coverage of the cavity surface, for improved therapeutic results.

HIV and STD Treatment and Prevention

When comprising appropriate protective agents, the foam is active against HIV infection and other infections (bacterial and fungal), including sexually transmitted disease (STD) by creating a protective layer and/or decreasing the frequency of transmission. Non-binding examples of protective agents include:

Negatively charged sulfated polymers, which have been reported to have anti-HIV-1 activity and are being considered for development as topical microbicides.

Dextrin sulphate, a microbicide, which in various laboratory and pre-clinical studies, has been shown to block the transfer of HIV virus into mammalian cells while at the same time not causing injury to normal cell tissue.

Cellulose acetate phthalate, which inactivates HIV-1, herpesvirus types 1 (HSV-1) and 2 (HSV-2) and the major non-viral STD pathogens; and found effective in animal models for vaginal infection by HSV-2 and simian immunodeficiency virus.

Several polymers, such as hydroxypropyl methylcellulose phthalate, carrageenans, naphthalene sulfonate polymer, sodium alginate, and cationic polymer, such as chitosan, are insoluble in water and can be solubilized in water by adjusting the pH of the environment to about 6 or above, or by the use of appropriate organic solvents. Vaginal secretions from healthy, reproductive-age women are characteristically acidic (pH values of 3.4 to 6.0). Consequently, the topical application of a formulation in which such polymers would be soluble (i.e., pH≥6) would be expected to contribute to a vaginal environment which is physiologically undesirable.

Thus, in one embodiment of present invention, there is an advantage to an oily foamable carrier, comprising solvents that solubilize water-insoluble polymenrs such as mentioned above. By way of non-limiting example, such solvents include polyethylene glycol, propylene glycol, hexylene glycol, benzyl alcohol, DMSO, isosorbide derivatives, such as dimethyl isosorbide, glycofurol and ethoxydiglycol (transcutol).

In one or more embodiments of the present invention, the foam composition is useful in the therapy of disorders that respond to transmucosal delivery of an active agent. By way of example, such disorders include, which respond to hormone therapy, such as hormone replacement therapy, and other systemic disorders, known to be affected by drugs that are delivered transmucosally.

The goal of a mucosal vaccine is to induce antigen-specific immune responses (cellular and humoral) that are detectable at the mucosal surfaces of the host. Because many pathogens initiate infection at the mucosal surfaces, pathogen-specific mucosal immune responses may provide superior protection against infectious diseases than immune responses induced by parenteral vaccines because parenteral vaccines do not induce mucosal immunity.

In the context of the present invention, the term immunization or vaccination refers to administering a preparation that contains an infectious agent or its components, which is able to stimulate an immune response that will protect a person from illness due to that agent. Such vaccines are expected be capable of preventing the transmission or limiting the severity of sexually-transmitted infections, such as HIV and other infectious disease. Vaccines are usually administered in conjunction with an adjuvant—a substance that is used in a vaccine to improve the immune response so that less vaccine is needed to produce a non-specific stimulator of the immune response. There are several types of adjuvants, including, for example, minerals such as aluminum hydroxide, aluminum phosphate and calcium phosphate, oil emulsions, products from bacteria (their synthetic derivatives as well as liposomes) or gram-negative bacteria, endotoxins, cholesterol, fatty acids, aliphatic amines, paraffinic and vegetable oils.

The foam composition of the present invention, comprising an immunizing agent, and optionally an adjuvant and administered onto the mucosal tissue of a body cavity, expands effectively in said cavity and provides optimal coverage of the cavity surface, for improved therapeutic results.

Post-Surgical Adhesions Treatment and Prevention

Adhesions are scars that form abnormal connections between tissue surfaces. Post-surgical adhesion formation is a natural consequence of surgery, resulting when tissue repairs itself following incision, cauterization, suturing, or other means of trauma. When comprising appropriate protective agents, the foam is suitable for the treatment or prevention of post surgical adhesions. The use of foam is particularly advantageous because foam can expand in the body cavity and penetrate into hidden areas that cannot be reached by any other alternative means of administration.

Hormonal Therapy

The foamable composition of the present invention is suitable for administering a hormone to a mucosal membrane or a body cavity, in order to deliver the hormone into the tissue of the target organ, in any disorder that responds to treatment with a hormone. Topically applied hormones can also be useful in contraception, when administered in foam, using a metered dose unit.

Active Agents

The composition of the present invention comprises at least one active agent, also referred to as "drug(s)". The at least one active agent may consist of a single drug or a combination of drugs that can be dissolved in the water phase or the hydrophobic phase of the carrier composition. Examples of such drugs are antibiotic, antibacterial, antifungal, antiviral, antiinflammatory, anesthetic, analgesic, antiallergic, corticosteroid and antiproliferative medications and mixtures thereof at any proportion. The concentration of drugs may be adopted to exert a therapeutic effect on a disease when applied to an afflicted area.

One important class of drugs comprises antibacterial agents. It is well known that bacterial infections are involved in a variety of superficial disorders of mucosal membranes and body cavities.

In one or more embodiments, the antibiotic agent is selected from the classes consisting of beta-lactam antibiotics, aminoglycosides, ansa-type antibiotics, anthraquinones, azoles, glycopeptides, macrolides, nucleosides, antibiotic peptides, antibiotic polyenes, antibiotic polyethers, quinolones, antibiotic steroids, sulfonamides, tetracycline, antibiotic metals, including silver, copper, zinc, mercury, tin, lead, bismuth, cadmium, chromium and ions and complexes thereof, oxidizing agents and substances that release free radicals and/or active oxygen, cationic antimicrobial agents, quaternary ammonium compounds, biguanides, triguanides, bisbiguanides and analogs and polymers thereof and naturally occurring antibiotic compounds.

An antibacterial drug can be active against gram positive and gram-negative bacteria, protozoa, aerobic bacteria and anaerobic bacteria.

By way of example, the antibacterial drugs are selected from chloramphenicol, beta-lactam antibiotics, aminoglycosides, ansa-type antibiotics, anthraquinones, azoles, glycopeptides, macrolides, nucleosides, antibiotic peptides, antibiotic polyenes, antibiotic polyethers, quinolones, antibiotic steroids, sulfonamides, tetracycline, antibiotic metals, including silver, copper, zinc, mercury, tin, lead, bismuth, cadmium, chromium and ions and complexes thereof, oxidizing agents and substances that release free radicals and/or active oxygen, cationic antimicrobial agents, quaternary ammonium compounds, biguanides, triguanides, bisbiguanides and analogs and polymers thereof and naturally occurring antibiotic compounds, metronidazlole and its derivatives and analogs, dicarboxylic acids, such as azelaic acid, slicylates, cyclosporines and any combination thereof at a therapeutically effective concentration.

Another group of antibacterial agents which have broad spectrum activity comprises strong oxidants and free radical liberating compounds, such as oxygen, hydrogen peroxide, benzoyl peroxide, elemental halogen species, as well as oxygenated halogen species, bleaching agents (e.g., sodium, calcium or magnesium hypochloride and the like), perchlorite species, iodine, iodate, and benzoyl peroxide. Organic oxidizing agents are also included in the definition of "oxidizing agent" according to the present invention, such as quinones. Such agents possess a potent broad spectrum activity Antibacterial compositions according to the present invention are selected to treat infections of an afflicted organ. The composition of the present invention, comprising a hydrophobic component, would facilitate an enhanced rate of penetration. Furthermore, the intrinsic antibacterial and antiinflammatory effects of the foam adjuvant agents, i.e., fatty alcohols and acids, provides a combined effect for better therapeutic response to treatment.

Fungal infections are another object of treatment using the composition of the present invention. Fungal infection of the vaginal cavity is one of the most common disorders seen in gynecological practice. Candidiasis is an infection caused by the yeast like fungus *Candida albicans* or occasionally other species of *candida*. Clinical syndromes of candidiasis include: (a) oral candidiasis (oral thrush); (b) candidiasis of the skin and genital mucous membrane; and (c) *candida* paronychia, which inflicts the nail.

The therapeutic composition may comprise an antifungal drug, which is active against dermatophytes and candida, selected from the group of, but not limited to azoles, diazoles, triazoles, miconazole, fluconazole, ketoconazole, clotrimazole, itraconazole griseofulvin, ciclopirox, amorolfine, terbinafine, Amphotericin B, potassium iodide, flucytosine (5FC) and any combination thereof at a therapeutically effective concentration. According to one preferred embodiment the active agent is metronidazole.

The composition of the present invention is particularly beneficial in the case of viral infections including herpes simplex Type 1 virus. Mollusca are small viral growths that appear singly or in groups on the face, trunk, lower abdomen, pelvis, inner thighs, or penis. Warts are a common, benign skin tumor caused by viral infection. HPV (Human Papillomavirus) is a common genital disease.

Viral infections are currently treated with various antiviral agents, as summarized in the following table:

| Drug | Viruses | Chemical Type |
|---|---|---|
| Vidarabine | Herpesviruses | Nucleoside analogue |
| Acyclovir | Herpes simplex (HSV) | Nucleoside analogue |
| Gancyclovir | Cytomegalovirus (CMV) | Nucleoside analogue |
| Nucleoside-analog reverse transcriptase inhibitors (NRTI): AZT (Zidovudine), ddI (Didanosine), ddC (Zalcitabine), d4T (Stavudine), 3TC (Lamivudine) | Retroviruses (HIV) | Nucleoside analogue |
| Non-nucleoside reverse transcriptase inhibitors (NNRTI): Nevirapine, Delavirdine | Retroviruses (HIV) | Nucleoside analogue |
| Protease Inhibitors: Saquinavir, Ritonavir, Indinavir, Nelfinavir | HIV | Peptide analogue |
| Ribavirin | Broad spectrum: HCV, HSV, measles, mumps, Lassa fever | Triazole carboxamide |
| Amantadine/Rimantadine | Influenza A strains | Tricyclic amine |
| Interferons | Hepatitis B and C | Protein |

Any of the above antiviral agents, in a therapeutically effective concentration, can be incorporated in the foam composition of the present invention. The composition of the present invention, which comprises a hydrophobic organic carrier, would facilitate an enhanced rate of penetration and better topical distribution of any of the above listed antiviral drugs. Furthermore, the intrinsic antiviral effects of the foam adjuvant agents, i.e., fatty alcohols and acids, provides a combined effect that should result in a better therapeutic response to treatment.

In one or more embodiments, the active agent is a steroid, selected from the following groups.

i. a compound containing a cyclopenta[a]phenanthrene skeleton;
ii. a compound, containing a cyclopenta[a]phenanthrene skeleton carrying one or more functional groups selected from halogens, alkyl groups, aryl groups, benzyl groups, carboxy groups and alkoxy groups;
iii.

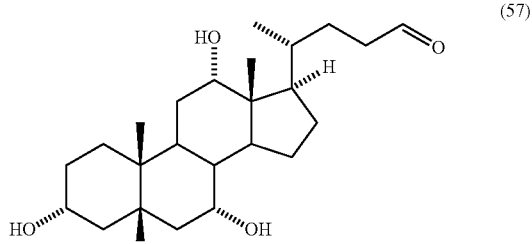

3α, 7α, 12α-Triydroxy-5β-cholestan-24-al
or cholaldehyde (from cholic acid)

iv. a steroid compound, selected from the families of (a) cardanolides, (b) bufanolides, (c) spirostans, (d) furostans, (e) steroid alkaloids, (f) a steroid lactone, (g) an oxo-steroid, (h) a steroid-alcohol and (i) a steroid-amine;
v. a steroid compound, where one or more of the cyclopenta[a]phenanthrene rings is contracted by loss of an unsubstituted methylene group;
vi. a steroid compound, where one or more of the cyclopenta[a]phenanthrene rings is expandeded by inclusion of a methylene group;
vii. a compound, containing a cyclopenta[a]phenanthrene skeleton and a carbocyclic or heterocyclic ring component fused to it;
viii. an anti-inflammatory steroid;
ix. a steroid possessing immunomodulating and/or anti-inflammatory properties;
x. a steroid, selected from the group of low-potency anti-inflammatory steroids, medium potency anti-inflammatory steroids and high potency anti-inflammatory steroids;
xi. an anti-inflammatory steroid, selected from the group consisting of hydrocortisone, hydrocortisone acetate, desonide, betamethasone valerate, clobetasone-17-butyrate, flucinonide, fluocinolone acetonide, alcometasone dipropionate, mometasone furoate, prednicarbate, triamcinolone acetonide, betamethasone-17-benzoate, methylprednisolone aceponate, betamethasone dipropionate, halcinonide, triamcinolone acetonide, halobetasol, clobetasol-17-propionate;
xii. a steroid hormone;
xiii. a steroid hormone, selected from the group consisting of an androgen, an estrogen and a progestogen
xiv. an androgen, selected from the group consisting of testosterone, testosterone cipionate, testosterone decanoate, testosterone enantate, testosterone isocaproate, testosterone phenylpropionate, testosterone propionate, testosterone undecylate, 5α-dihydrotestosterone, dehydroepiandrosterone (also termed prasterone and DHEA), androstenedione, androstanediol, androsterone, androstenolone, prasterone enantate, prasterone sodium sulfate, ormeloxifene, mesterolone, fluoxymesterone, methyltestosterone, gestrinone, delmadinone, delmadinone acetate, chlormadinone, chlormadinone acetate, danazol and testolactone;
xv. an estrogen selected from the group consisting of estradiol, estradiol benzoate, estradiol cipionate, estradiol dipropionate, estradiol enantate, estradiol hexahydrobenzoate, estradiol phenylpropionate, estradiol valerate, polyestradiol phosphate, estriol, estriol sodium succinate, estriol succinate, polyestriol phosphate, quinestradol, ethinylestradiol, estrapronicate, mestranol, estrapronicate and equilin;
xvi. a progestogen, selected from the group consisting of progesterone, norethisterone, norethisterone acetate, norethisterone enantate, medroxyprogesterone acetate, delmadinone acetate, flugestone acetate, dydrogesterone, desogestrel, norgestrel, levonorgestrel, dydrogesterone, gestodene, chlormadinone acetate, dienogest, drospirenone, lynestrenol, tybolone, cyproterone acetate, megestrol acetate, nomegestrol acetate;
xvii. an inhibitor of a steroid hormone;
xviii. an inhibitor of a steroid hormone, selected from the group consisting of inhibitors are finasteride, dutasteride and spironolactone;
xix. a vitamin D;
xx. a vitamin D, selected from the group consisting of cholecalciferol, 25-hydroxycholecalciferol, 1α,25-dihydroxycholecalciferol, ergocalciferol, 1α,25-dihydroxyergocalciferol, 22,23-dihydroergocalciferol, 1,24,25-trihydroxycholecalciferol, previtamin $D_3$, tachysterol$_3$ (also termed tacalciol), Isovitamin $D_3$, dihydrotachysterol$_3$, (1S)-hydroxycalciol, (24R)-hydroxycalcidiol, 25-fluorocalciol, ercalcidiol, ertacalciol, (5E)-Isocalciol, 22,23-Dihydroercalciol, (24S)-methylcalciol, (5E)-(10S)-

10,19-Dihydroercalciol, (24S)-Ethylcalciol and (22E)-(24R)-Ethyl-22,23-didehydrocalciol; and xxi. a phytosteroid or a phytosterol.

According to another embodiment according to the present invention the at least one active agent is an antiinflammatory or antiallergic agent. An antiinflammatory or antiallergic agent can be selected from the group of corticosteroids (as listed above), non-steroidal antiinflammatory drugs (NSAIDs), anti-histamines, immunosuppressants and any combination thereof at a therapeutically effective concentration.

Since corticosteroid drugs are typically hydrophobic, the carrier of the present invention, comprising a hydrophobic organic carrier, is most suitable as a vehicle to facilitate better topical distribution and an enhanced rate of penetration of any of the above listed drugs. Furthermore, the intrinsic antiviral, antibacterial and antiinflammatory effects of the foam adjuvant agents, i.e., fatty alcohols and acids, provides a combined effect that should result in a better therapeutic response to treatment.

Antihistaminic agents may comprise, among other options, diphenhydramine, doxepin, phrilamine maleate, chlorpheniramine, tripelennamine, phenothiazines, promethazine hydrochloride and dimethindene maleate. These drugs, as well as additional antihistamines can also be incorporated in the composition of the present invention.

A second class of anti-inflammatory agents, which is useful in the foam of the present invention, includes the nonsteroidal anti-inflammatory agents (NSAIDs). The variety of compounds encompassed by this group is well-known to those skilled in the art. Specific non-steroidal anti-inflammatory agents useful in the composition invention include, but are not limited to: oxicams, such as piroxicam, isoxicam, tenoxicam, sudoxicam; salicylates, such as salicylic acid, ethyl salicylate, methyl salycilate, aspirin, disalcid, benorylate, trilisate, safapryn, solprin, diflunisal, and fendosal; acetic acid derivatives, such as diclofenac, fenclofenac, indomethacin, sulindac, tolmetin, isoxepac, furofenac, tiopinac, zidometacin, acematacin, fentiazac, zomepirac, clindanac, oxepinac, felbinac, and ketorolac; fenamates, such as mefenamic, meclofenamic, flufenamic, niflumic, and tolfenamic acids; propionic acid derivatives, such as ibuprofen, naproxen, benoxaprofen, flurbiprofen, ketoprofen, fenoprofen, fenbufen, indopropfen, pirprofen, carprofen, oxaprozin, pranoprofen, miroprofen, tioxaprofen, suprofen, alminoprofen, and tiaprofenic; and pyrazoles, such as phenylbutazone, oxyphenbutazone, feprazone, azapropazone, and trimethazone.

Any further steroidal and nonsteroidal compounds, having the capacity to prevent, alleviate the symptoms of, treat or cure inflammation processes, are generally included, as possible anti-inflammatory agents, according to the present invention.

The therapeutic foam composition of the present invention may also comprise an antiinflammatory or antiallergic agent, wherein said agent reduces the occurrence of pro-inflammatory cytokines or inhibits the effect of pro-inflammatory cytokines.

Mixtures of such anti-inflammatory agents may also be employed, as well as the dermatologically acceptable salts, esters, amides, prodrugs and derivatives of these agents.

The compositions of the present invention may contain a safe and effective amount of a topical anesthetic. Examples of local anesthetic drugs include benzocaine, lidocaine, bupivacaine, chlorprocaine, dibucaine, etidocaine, mepivacaine, tetracaine, dyclonine, hexylcaine, procaine, cocaine, ketamine, pramoxine, phenol, and therapeutically acceptable salts thereof. Mixtures of such anesthetic agents may be synergistically beneficial.

Anti cancer agents can also be used according to the present invention as the drug of choice for treating for example vaginal, cervical and rectal malignancies. In certain cases, topical cytotoxic and antiproliferative drugs are used to treat or prevent such cancers, including 5-fluorouracil, also called 5-FU. 5-FU, as well as any other anti-cancer agents, know in the art of cancer medicine, can be incorporated in the foam at therapeutically effective levels.

A preferred family of anticancer drugs, suitable for usage in the foam of the present formulation comprises antiestrogens, such as tamoxifen. Tamoxifen blocks the effects of the hormone estrogen in the body.

A safe and effective amount of an anti-oxidant/radical scavenger may be added to the compositions of the present invention, preferably from about 0.1% to about 10% (w/w), more preferably from about 1% to about 5% (w/w), of the composition.

Anti-oxidants/radical scavengers such as ascorbic acid (vitamin C) and its salts, ascorbyl esters of fatty acids, ascorbic acid derivatives (e.g., magnesium ascorbyl phosphate, sodium ascorbyl phosphate, ascorbyl sorbate), tocopherol (vitamin E), tocopherol sorbate, tocopherol acetate, other esters of tocopherol, butylated hydroxy benzoic acids and their salts, 6-hydroxy-2,5,7,8-tetramethylchroman-2-carboxylic acid (commercially available under the tradename Trolox®), gallic acid and its alkyl esters, especially propyl gallate, uric acid and its salts and alkyl esters, sorbic acid and its salts, lipoic acid, amines (e.g., N,N-diethylhydroxylamine, amino-guanidine), sulfhydryl compounds (e.g., glutathione), dihydroxy fumaric acid and its salts, lycine pidolate, arginine pilolate, nordihydroguaiaretic acid, bioflavonoids, curcumin, lysine, methionine, proline, superoxide dismutase, silymarin, tea extracts, grape skin/seed extracts, melanin, and rosemary extracts may be used.

The foam of the present invention is suitable for delivering cell and tissue protecting and revitalizing anti-oxidants/radical scavengers. Polyunsaturated fatty acids, containing omega-3 and omega-6 fatty acids (e.g., linoleic and linolenic acid, gamma-linoleic acid (GLA), eicosapentaenoic acid (EPA) and docosahexaenoic acid (DHA) are beneficial in the treatment of inflammation conditions. Likewise, emollients and silicone oils exert moisture-retaining and protective effects on the target tissue. Thus, in a preferred embodiment, a tissue protective foam is provided, wherein the hydrophobic organic carrier comprises in full or in part, a solvent, selected from the group of emollients, silicone oil and oils, rich in unsaturated fatty acids, thus, affording a synergistic therapeutic effect of the anti-oxidants/radical scavenger agent and the vehicle components.

Active agents, which are known in the art of pharmacology to treat mucosal irritations and inhibit inflammation, can be beneficially incorporated in the foam of the present invention.

Examples of such active agents include chamomile extract (*matricaria recutitia*), cucumber distillate (*cucumis sativus*), lavender water (*lavendula angustifolia*), rose water (*rosa damascena*), witch hazel (*hamamelis virginiana*), allantoin, bisabolol, rosehip oil, calendula oil, azulaene, menthol and camphor.

There are several potential uses of the foam, particularly the silicone-oil based foam, as a lubricating foam. Typical examples are moisture protection foam and antifriction foam. For such purposes, the foam can be used in its basic composition (without additional formulation aids and active ingredients), or with the addition of such additives.

According to one embodiment, the at least one active agent is selected from the group of solvent, surface active agent, foam adjuvant and polymeric agent.

Penetration Enhancers

A penetration enhancer or permeation enhancer is an agent used to increase the permeability of tissue to a pharmacologically active agent to increase the rate at which the drug diffuses through the skin and enters the tissues and bloodstream. A chemical penetration enhancer increases skin permeability by reversibly altering the physiochemical nature of the tissue to reduce its diffusional resistance. According to one or more embodiments of the present invention a penetration enhancer is incorporated into the foam composition.

Examples of penetration enhancers, according to the present invention include: polyols, such as propylene glycol, hexylene glycol, diethylene glycol, propylene glycol n-alkanols, terpenes, di-terpenes, tri-terpenes, terpen-ols, limonene, terpene-ol, 1-menthol, dioxolane, ethylene glycol, other glycols, and glycerol; sulfoxides, such as dimethylsulfoxide (DMSO), dimethylformanide, methyl dodecyl sulfoxide, dimethylacetamide; monooleate of ethoxylated glycerides (with 8 to 10 ethylene oxide units); Azone (1-dodecylazacycloheptan-2-one), 2-(n-nonyl)-1,3-dioxolane; esters, such as isopropyl myristate/palmitate, ethyl acetate, butyl acetate, methyl proprionate, capric/caprylic triglycerides, octylmyristate, dodecyl-myristate; myristyl alcohol, lauryl alcohol, lauric acid, lauryl lactate ketones; amides, such as acetamide oleates such as triolein; various surfactants, such as sodium lauryl sulfate; various alkanoic acids such as caprylic acid; lactam compounds, such as azone; alkanols, such as oleyl alcohol; dialkylamino acetates, and admixtures thereof.

Lower alcohols, such as ethanol, propanol, isopropanol, butanol, iso-butanol, t-butanol and pentanol are less desirable penetration enhancers according to the present invention, due to their irritation properties.

Yet, another preferred class of penetration enhancers in the cyclodextrines and related compounds. Cyclodextrins are structurally related cyclic oligomaltoses which form a new group of therapeutic excipients.

The invention is described with reference to the following examples. This invention is not limited to these examples and experiments. Many variations will suggest themselves and are within the full intended scope of the appended claims.

Example 1

General Procedure for Preparing Foam Composition

Aqueous Phase: At least one polymeric agent and at least one surface-active agent are dissolved in water, with agitation. The solution is warmed to about 50° C. to about 70° C. Water soluble therapeutic active ingredients and optional water soluble ingredients are added with agitation to the Aqueous Phase mixture.

Oil Phase: At least one hydrophobic organic carrier is heated to same above temperature. Foam adjuvant agent is added to preheated hydrophobic organic carrier. Oil soluble therapeutic active agent or agents and optional oil soluble formulation ingredients are added with agitation to the Hydrophobic Phase mixture.

The warm Hydrophobic Phase is gradually poured into the warm Aqueous Phase, with agitation, followed by Ultraturax or Silverson homogenization. The mixture is allowed to cool down to ambient temperature. In case of heat sensitive active ingredients, the active ingredient is added with agitation to the mixture after cooling to ambient temperature. The mixture, at ambient temperature, is added to an aerosol container, the container is sealed and appropriate amount of propellant (about 3% to about 25 w % of the composition mass) is added under pressure into the container.

Example 2

Emulsion Foam Carrier Composition for Vaginal and Rectal Treatment

The ingredients listed in the table below are combined to form a foamable emulsion composition.

|  | Ingredient | Version No. 1 | Version No. 2 | Version No. 3 | Version No. 4 |
|---|---|---|---|---|---|
| Hydrophobic organic carrier | MCT oil | 30 | — | 15 | 12 |
|  | IPM | — | 30 | — | 12 |
| Foam adjuvant | Stearyl Alcohol | 1.0 | 1.0 | 1.0 | 1.0 |
| Surface-active agent | GMS | 1.0 | 1.0 | 1.0 | 1.0 |
|  | PEG S-40 | 3 | 3 | 3 | 3 |
|  | Polysorbate-60 | 1 | 1 | 1 | 1 |
| Polymeric agent | Xanthan Gum | 0.3 | 0.3 | — | — |
|  | Methocel ELV15 | 0.4 | 0.4 | — | — |
|  | Natrosol | — | — | 1.5 | 1.5 |
| Other Ingredients | Antioxidant | 0.2 | 0.2 | 0.2 | 0.2 |
|  | Preservatives | 1.0 | 1.0 | 1.0 | 1.0 |
| Propellant* | Propane/butane | 8.0 | 8.0 | 8.0 | 8.0 |
| Water | Water | To 100 | To 100 | To 100 | To 100 |
| Foam Specific gravity (gr/mL) |  | ND | ND | ND | 0.06 |

The liquefied or gas propellant can be added at a concentration of about 3% to about 25%. The compositions use only non-ionic surface active agents, and the total amount of surface active agent, foam adjuvants and polymeric agent ranged from 1.4 to 2.1% (w/w). The foam of this example is useful as a carrier of active agents, as exemplified in examples below. It is also useful as lubricating foam, for various purposes.

Example 3

Further Mixed Oil Foam Carrier Composition for Vaginal and Rectal Treatment

The ingredients listed in the table below are combined to form a foamable emulsion composition.

|  | Ingredient | Version No. 1 ~25% Oil | Version No. 2 ~12.5% Oil |
|---|---|---|---|
| Hydrophobic organic carrier | Mineral oil | 10.2 | 5.6 |
|  | Isopropyl myristate | 5.0 | 2.5 |
|  | MCT oil | 7.0 | 3.8 |
| Foam adjuvant agent | Stearyl Alcohol | 2.0 | 2.0 |
| Surface-active agent | Brij 72 | 2.5 | 2.5 |
|  | Brij 721 | 1.0 | 1.0 |
|  | Cocoa amido propyl betaine | 0.5 | 0.5 |
| Polymeric agent | Xanthan Gum | 0.3 | — |
|  | Natrosol | — | 0.3 |
|  | Methocel ELV15 | 0.5 | — |
| Propellant* | Propane/butane | 6.0 | 6.0 |
| Water | Water | To 100 | To 100 |

The liquefied or gas propellant can be added at a concentration of about 3% to about 25%. The foams of this example have a non-ionic surface active agent to ionic surface active agent ratio (w/w) of 20:1 and 14:1 for versions 1 and 2, respectively. Total amounts of surface active agent foam adjuvant and polymeric agent is in the range of about 1.75 to about 3.5% (w/w).

The compositions are useful as carriers of active therapeutic active ingredients, as exemplified in examples below. It is also useful as lubricating foam, for various purposes.

The following examples, representing optional drug-containing foams, are prototype formulations, which have not been optimized for stability and inter-component compatibility. Such optimization is a customary need, which can be done, using means, known to those skilled in the art of therapeutic formulation

Example 4

Antibacterial Foam Composition for Vaginal Vaginosis and Other Vaginal and Rectal Infections

|  | % w/w | % w/w | % w/w |
|---|---|---|---|
| Metronidazole | 1.00 | — | — |
| Clindamycin | — | 2.00 | 2.00 |
| Mineral oil | 6.00 | 6.00 | 6.00 |
| Mineral oil | 6.00 | 6.00 | 6.00 |
| Isopropyl myristate | 6.00 | 6.00 | 6.00 |
| Glyceryl monostearate | 1.00 | 1.00 | 1.00 |
| Stearyl alcohol | 1.00 | 1.00 | 1.00 |
| Xantan gum | 0.30 | 0.30 | 0.30 |
| Methocel K100M | 0.30 | 0.30 | 0.30 |
| Tween 60 | 1.00 | 1.00 | 1.00 |
| MYRJ 52 | 3.00 | 3.00 | 3.00 |
| Cocoamidopropylbetaine | 0.50 | 0.50 | — |
| Parabens (phenoxy ethanol and methyl, ethyl and propyl hydroxy benzoate mixture) | 0.80 | 0.80 | 0.80 |
| Propellant Propane/butane * | 10.00 | 10.00 | 10.00 |
| Water | to 100.0 | to 100.0 | to 100.0 |

The liquefied or gas propellant can be added at a concentration of about 3% to about 25%. The foams of this example have a non-ionic surface active agent to ionic surface active agent ratio ranging from about 20:1 to about 6:1. In one version, no ionic surface active agent was present.

Example 5

Antifungal Foam Composition

| Ingredient | Version 1 "Miconazole" % w/w | Version 2 "Clotrimazole" % w/w | Version 3 "Econazole" % w/w | Version 4 "Nystatin" % w/w |
|---|---|---|---|---|
| Carrier Ingredients | | | | |
| Mineral oil | 30 | — | — | 10 |
| Isopropyl myristate | — | 30 | — | 10 |
| MCT oil | — | — | 30 | 10 |
| Stearyl Alcohol | 2.0 | 2.0 | 2.0 | 2.0 |
| Myrj 40 | — | — | 0.8 | — |
| GMS | 2.0 | 2.0 | 2.0 | 2.0 |

-continued

| Ingredient | Version 1 "Miconazole" % w/w | Version 2 "Clotrimazole" % w/w | Version 3 "Econazole" % w/w | Version 4 "Nystatin" % w/w |
|---|---|---|---|---|
| Natrosol | 1.0 | 1.0 | 1.0 | 1.0 |
| Active Ingredients | | | | |
| Miconazole | 1 | — | — | — |
| Clotrimazole | — | 2 | — | — |
| Econazole | — | — | 1 | — |
| Nystatin | — | — | — | 100,000 Units/gr |
| Propellant* Propane/butane | 10.0 | 10.0 | 10.0 | 10.0 |
| Water | To 100 | To 100 | To 100 | To 100 |

The liquefied or gas propellant can be added at a concentration of about 3% to about 25%. The foams of this example have a non-ionic surface active agent to ionic surface active agent ratio ranging from about 16:1 to about 6:1. Total surface active agent, foam adjuvant and polymeric agent ranges from 2.05 to 3.5% (w/w). They are useful in the treatment of fungal and yeast infections.

Example 6

Corticosteroid Foam Composition

|  | % w/w | % w/w | % w/w | % w/w | % w/w |
|---|---|---|---|---|---|
| Mineral oil | 5.60 | 5.60 | 5.60 | 5.60 | 5.60 |
| Isopropyl myristate | 5.60 | 5.60 | 5.60 | 5.60 | 5.60 |
| Glyceryl monostearate | 0.45 | 0.45 | 1.00 | 1.00 | 1.00 |
| Stearyl alcohol | 0.85 | 0.85 | 0.85 | 0.85 | 0.85 |
| Myrj 52 | 2.60 | 2.60 | 2.60 | 2.60 | 2.60 |
| Xantan gum | 0.26 | — | — | — | — |
| Methocel K100M | 0.26 | — | — | — | — |
| Chitosan | — | — | 1.00 | — | — |
| Hyaluronic acid | — | — | — | 0.50 | 0.50 |
| Avicel CL611 | — | 2.00 | 2.00 | 2.00 | 2.00 |
| TWEEN 80 | 0.90 | 0.90 | 0.90 | 0.90 | 0.90 |
| Cocoamidopropyl betaine | 0.41 | 0.41 | 0.41 | 0.41 | 0.41 |
| Betametasone valerate | 0.12 | — | 0.12 | 0.12 | — |
| Hydrocortisone butyrate | — | 0.10 | — | — | 0.10 |
| Propylene glycol | 3.00 | 3.00 | 3.00 | 3.00 | 3.00 |
| Parabens (phenoxy ethanol and methyl, ethyl and propyl hydroxy benzoate mixture) | 0.8 | 0.8 | 0.8 | 0.8 | 0.8 |
| Propellant Propane/butane* | 12.00 | 12.00 | 12.00 | 12.00 | 12.00 |
| Water | To 100 | To 100 | To 100 | To 100 | To 100 |

The liquefied or gas propellant can be added at a concentration of about 3% to about 25%. The foams of this example have a non-ionic surfactant to ionic surfactant ratio ranging from about 20:1 to about 14:1. Total surface active agent, foam adjuvant and polymeric agent ranged from about 2% to about 3.5% (w/w).

Example 7

Antiviral Foam Composition

| Ingredient | Version 1 "Acyclovir" % w/w | Version 2 "Acyclovir" % w/w | Version 3 "α-Interferon" % w/w |
|---|---|---|---|
| Carrier Ingredients | | | |
| Mineral oil | 48.4 | 11.0 | 5.4 |
| Isopropyl myristate | — | 5.0 | 2.5 |
| MCT oil | — | 7.0 | 3.5 |
| Stearyl Alcohol | 0.7 | 0.4 | 0.2 |
| Water | To 100 | To 100 | To 100 |
| Sucrose ester SP70 | 0.8 | 0.8 | 0.8 |
| Distilled monoglyceride | | 1.2 | 0.6 |
| Sodium lauryl sulphate | 0.05 | 0.1 | 0.1 |
| Xanthan Gum | 0.2 | 0.3 | 0.3 |
| Methocel ELV15 | 0.2 | 0.6 | 0.6 |
| Active Ingredients | | | |
| Acyclovir | 5 | 5 | — |
| α-Interferon | — | — | 105 IU/g |
| Propellant* | 6.0 | 6.0 | 10.0 |
| Propane/butane | | | |

The liquid is added at a concentration of about 3% to about 25%. The foam of this example has a non-ionic surfactant to ionic surfactant ration ranging from 20:1 to 14:1. Total surface active agent, foaming adjuvant and polymeric agent ranged from about 2% to about 3.5% (w/w).

Example 8

Compositions Consisting of Corticosteroids, Antifungal and Antiviral Agents

| Ingredient | % w/w | % w/w | % w/w | % w/w |
|---|---|---|---|---|
| Betamethasone valerate | 0.1 | | | |
| Ketoconazole | | 2.0 | 2.0 | |
| Acyclovir | | | | 5.0 |
| Caprylic/Capric Triglycerides | 60.9 | 60.0 | 59.0 | 56.0 |
| Propylene glycol | 10.0 | 10.0 | | 5.0 |
| Hexylene glycol | | | 10.0 | |
| Potent solvent | — | — | — | 5.0 |
| Lecithin | 10.0 | 10.0 | 10.0 | 10.0 |
| Stearyl alcohol | 5.0 | 5.0 | 5.0 | 5.0 |
| Glyceryl monostearate | 2.0 | 2.0 | 2.0 | 2.0 |
| PVP K90 | 2.0 | 2.0 | 2.0 | 2.0 |
| Preservative | 0.3 | 0.3 | 0.3 | 0.3 |
| Propellant | 10.0 | 12.0 | 12.0 | 10.0 |
| Propane/butane * | | | | |
| Purified water** | TO 100 | TO 100 | TO 100 | TO 100 |

The liquefied or gas propellant can be added at a concentration of about 3% to about 25%. Water content in these compositions was about 10%

Example 9

Comparative Tolerability and Acceptability Study of a Placebo Foam Composition Vs. a Conventional Gel Four patients compared the use of the foam preparation of Example 4, Version 2, with a conventional intravaginal gel preparation (Metrogel Vaginal, 3M). They were asked to describe their feeling about the application of each of the products and to give their general rating for each of the products on a scale of 0-3 (0=poor; 1=barely acceptable; 2=acceptable and 3=excellent).

As demonstrated in the following table, the foam preparation obtained higher rates in all aspects of the test.

| Property | Foam Preparation Mean Rating | MetroGel Vaginal Mean Rating |
|---|---|---|
| Ease of preparation prior to administration | 2.8 | 0.6 |
| Ease of insertion | 2. | 1.2 |
| Comfort upon insertion | 2.0 | 1.2 |
| Ease of dosing | 2.0 | 1.5 |
| Lack of dripping | 2.0 | 1.3 |
| Ease of removal | 2.2 | 1.6 |
| Comfort upon removal | 1.9 | 1.3 |
| Overall rating | 2.2 | 1.3 |

Example 10

Animal Model for Drug Administration and Duration

The composition of Example 4, Version 2 was prepared, with the addition of 0.2% methylene blue as coloring agent. A female sheep was administered intra-vaginally one dose of the foam (metered dose, 50 μL). The vagina and cervix were observed by colposcopy and recorded photographically. The insertion was very easy. Foam expanded effectively and vaginal cavity and cervix area were fully covered. Fifteen minutes after treatment, the vagina was swabbed. Colposcopy revealed that the entire vaginal cavity and cervix area were still covered by the blue pigment. There was no overflow of the foam and no dripping after administration. No signs of irritation were observed.

Example 11

Very Low Surfactants Formulation

| | % w/w | % w/w | % w/w | % w/w |
|---|---|---|---|---|
| Mineral oil | 20.00 | 20.00 | 30.00 | |
| Isopropyl palmitate | | | | 15.00 |
| MCT oil | | | | 15.00 |
| Glyceryl monostearate | 1.00 | 1.00 | | |
| Sucrose ester and Sorbitan stearate (Arlatone 2121) | 0.20 | 0.20 | 0.20 | 0.20 |
| Pemulen TR1 | 00.20 | | | |
| Pemulen TR2 | | | 00.20 | 00.20 |
| Methocel K100 | 00.30 | 00.30 | 00.30 | 00.30 |
| Xantan Gum | | | | |
| TWEEN 80 | | 11.00 | | |
| TEA | 00.10 | | .0.10 | 00.10 |
| Propellant | 112.00 | 112.00 | 112.00 | 112.00 |
| Water | To 100 | To 100 | To 100 | To 100 |

The formulations of Example 11 are made stable with unexpectedly low surfactant concentration making them highly non irritating and of lower itching potential for conditions of damaged infected or diseased condition vaginal mucous.

Although various embodiments that incorporate the teachings of the present invention have been shown and in detail herein, those skilled in the art can readily devise many other varied embodiments that incorporate these teachings. All references mentioned herein are incorporated by reference.

What is claimed is:

1. A foamable composition comprising a carrier and a liquefied or a compressed gas propellant, the carrier comprising:
   i) about 0.1% to about 5% by weight of the carrier of a surface-active agent;
   ii) about 2% to about 75% by weight of the carrier of an organic solvent selected from the group consisting of an emollient, a polar solvent, an oil, and mixtures thereof;
   iii) about 0.01% to about 5% by weight of the carrier of at least one polymeric agent selected from the group consisting of a bioadhesive agent, a gelling agent, a film forming agent, and a phase change agent; and
   iv) water;
wherein upon release from a foam dispenser, a foam is produced; and
wherein the foam remains stable as a foam for at least 60 seconds at 37° C.

2. The foamable composition of claim 1, wherein the carrier further comprises an active agent.

3. The foamable composition of claim 1, wherein the liquefied or compressed gas propellant is present at about 3% to about 25% by weight of the carrier.

4. The foamable composition of claim 1, wherein the organic solvent is selected from the group consisting of an emollient, a polar solvent, an essential oil, and mixtures of any two or more thereof.

5. The foamable composition of claim 1, wherein the carrier comprises a micro-emulsion.

6. The foamable composition of claim 1, wherein the carrier comprises nanoparticles.

7. The foamable composition of claim 1, wherein the surface-active agent is present at less than about 2% by weight of the carrier.

8. The foamable composition of claim 1, wherein the polymeric agent is present at less than about 1% by weight of the carrier.

9. The foamable composition of claim 1, wherein the carrier does not include petrolatum.

10. The foamable composition of claim 2, wherein the active agent is selected from the group consisting of an antibacterial agent, an antibiotic, an anti-parasitic agent, an antifungal agent, an antiviral agent, a corticosteroid, a steroidal anti-inflammatory agent, a non-steroidal immunomodulating agent, an immunosuppressant, an anti-allergic agent, an antihistamine, an anticancer agent, a hormone, an androgen, an estrogen, a progesterone, a contraceptive agent, a retinoid, vitamin A, vitamin B, vitamin D, an anesthetic, a lubricating agent, an immunizing agent, a cytotoxic drug, an antiproliferative drug, an anti-oxidant, a radical scavenger, and mixtures of any two or more thereof.

11. The foamable composition of claim 1, wherein the carrier comprises less than about 2% by weight of the carrier of one or more lower alcohols having up to 5 carbon atoms in their carbon chain skeleton.

12. The foamable composition of claim 1, wherein the polymeric agent is selected from the group consisting of a locust bean gum, sodium alginate, sodium caseinate, egg albumin, a gelatin agar, a carrageenin gum, a xanthan gum, a quince seed extract, a tragacanth gum, a guar gum, a starch, a chemically modified starch, cellulose ethers, a hydroxyethyl cellulose, a methyl cellulose, a carboxymethyl cellulose, a hydroxy propylmethyl cellulose, a hydroxypropyl guar gum, a soluble starch, cationic celluloses, cationic guars, carboxyvinyl polymers, a polyvinylpyrrolidone, a polyvinyl alcohol, polyacrylic acid polymers, polymethacrylic acid polymers, polyvinyl acetate polymers, polyvinyl chloride polymers, polyvinylidene chloride polymers, acrylic acid/ethyl acrylate copolymers, crosslinked copolymers of acrylic acid and C10-C30 alkyl acrylate (pemulen), carboxyvinyl polymers, a carbopol, and mixtures of any two or more thereof.

13. The foamable composition of claim 1, wherein the foamable composition further comprises about 0.1% to about 5% by weight of the carrier of a foam adjuvant selected from the group consisting of a fatty alcohol having 15 or more carbons in its carbon chain; a fatty acid having 16 or more carbons in its carbon chain; fatty alcohols, derived from beeswax and including a mixture of alcohols, a majority of which has at least 20 carbon atoms in their carbon chain; a fatty alcohol having at least one double bond; a fatty acid having at least one double bond; a branched fatty alcohol; a branched fatty acid; a fatty acid substituted with a hydroxyl group; cetyl alcohol; stearyl alcohol; arachidyl alcohol; behenyl alcohol; 1-triacontanol; hexadecanoic acid; stearic acid; arachidic acid; behenic acid; octacosanoic acid; 12-hydroxy stearic acid; and mixtures of any two or more thereof.

14. The foamable composition of claim 1, wherein the surface-active agent is selected from the group consisting of a non ionic surface-active agent, a cationic surface-active agent, an amphoteric surface-active agent, an ionic surface-active agent, and mixtures of any two or more thereof.

15. The foamable composition of claim 1, wherein the surface-active agent is a non ionic surface-active agent.

16. The foamable composition of claim 13, wherein the combined amount of foam adjuvant, surface active agent, and gelling agent is less than about 8% by weight of the carrier.

17. The foamable composition of claim 14, wherein the surface-active agent is selected from the group consisting of a polysorbate, polyoxyethylene (20) sorbitan monostearate, polyoxyethylene (20) sorbitan monooleate, a polyoxyethylene fatty acid ester, polyoxyethylene (8) stearate, polyoxyethylene (20) stearate, polyoxyethylene (40) stearate, polyoxyethylene (100) stearate, a polyoxyethylene alkyl ether, polyoxyethylene cetyl ether, polyoxyethylene (23) cetyl ether, polyoxyethylene (2) cetyl ether, polyoxyethylene (10) cetyl ether, isoceteth-20, a sucrose ester, a partial ester of sorbitol, an anhydride of a partial ester of sorbitol, sorbitan monolaurate, sorbitan stearate, a monoglyceride, glyceryl monostearate, a diglyceride, lecithin, sodium methyl cocoyl taurate, sodium methyl oleoyl taurate, sodium lauryl sulfate, triethanolamine lauryl sulfate, a betaine, cocamidopropyl betaine, and mixtures of any two or more thereof.

18. The foamable composition of claim 1, wherein the carrier comprises more than about 50% by weight of the carrier of a potent solvent.

19. The foamable composition of claim 18, wherein the potent solvent is selected from the group consisting of polyethylene glycol, propylene glycol, hexylene glycol, butanediol and isomers thereof, glycerol, benzyl alcohol, dimethyl sulfoxide, ethyl oleate, ethyl caprylate, dimethylacetamide, N-methylpyrrolidone, N-hydroxyethylpyrrolidone, polyvinylpyrrolidone, isosorbide derivatives, dimethyl isosorbide, glycofurol, ethoxydiglycol, and mixtures of any two or more thereof.

20. The foamable composition of claim 10, wherein the active agent is suitable for the treatment of a disorder of a body cavity or a mucosal surface, wherein the disorder is selected from the group consisting of a bacterial infection, a fungal infection, a viral infection, vaginal dryness, dyspareunia, HIV, a sexually transmitted disease, post-surgical adhesions, a hormonal deficiency, and a combination of any two or more thereof.

21. A foamable composition comprising a carrier and a liquefied or a compressed gas propellant, the carrier comprising:
   i) about 0.1% to about 5% by weight of the carrier of a surface-active agent;
   ii) about 70% to about 99% by weight of the carrier of a hydrophobic organic solvent;
   iii) a stabilizer selected from the group consisting of about 0.01% to about 5% by weight of the carrier of a polymeric agent and about 0.1% to about 5% by weight of the carrier of foam adjuvant;
wherein upon release from a foam dispenser, a foam is produced; and
wherein the foam remains stable as a foam for at least 60 seconds at 37° C.

22. A foamable composition comprising a carrier and a liquefied or a compressed gas propellant, the carrier comprising:
   i) about 0.2% to about 15% by weight of the carrier of a surface-active agent;
   ii) about 70% to about 99% by weight of the carrier of a hydrophobic organic solvent;
   iii) a stabilizer selected from the group consisting of about 0.01% to about 5% by weight of the carrier of a polymeric agent and about 0.1% to about 5% by weight of the carrier of foam adjuvant;
wherein upon release from a foam dispenser, a foam is produced; and
wherein the foam remains stable as a foam for at least 60 seconds at 37° C.

23. The foamable composition of claim 1, wherein the foam remains stable as a foam for at least 2 or 3 minutes at 37° C.

24. The foamable composition of claim 22, wherein the foam remains stable as a foam for at least 2 or 3 minutes at 37° C.

25. The foamable composition of claim 2, wherein the active agent is an azole.

26. The foamable composition of claim 25, wherein the azole is selected from the group consisting of azoles, diazoles, triazoles, pyrazoles, and mixtures of any two or more thereof.

27. The foamable composition of claim 26, wherein the azole is selected from the group consisting of clotrimazole, econazole, fluconazole, ketoconazole, itraconazole, metronidazole, miconazole, phenylbutazone, oxyphenbutazone, feprazone, azapropazone, trimethazone, and mixtures of any two or more thereof.

* * * * *

UNITED STATES PATENT AND TRADEMARK OFFICE
CERTIFICATE OF CORRECTION

| | |
|---|---|
| PATENT NO. | : 8,722,021 B2 |
| APPLICATION NO. | : 13/786902 |
| DATED | : May 13, 2014 |
| INVENTOR(S) | : Doron Friedman et al. |

It is certified that error appears in the above-identified patent and that said Letters Patent is hereby corrected as shown below:

In the specification

Column 1, Line 18, please delete "60/429,385," and insert -- 60/492,385, --, therefor.

In the claims

Column 31, Line 34, In claim 6, delete "nanoparticles." and insert -- nano-particles. --, therefor.

Column 32, Line 42, In claim 17, delete "polyoxyethylene" and insert -- a polyoxyethylene --, therefor.

Column 32, Line 47, In claim 17, delete "lecithin," and insert -- a lecithin, --, therefor.

Signed and Sealed this
Tenth Day of November, 2015

Michelle K. Lee
*Director of the United States Patent and Trademark Office*